US010709791B2

(12) United States Patent
Stayton et al.

(10) Patent No.: US 10,709,791 B2
(45) Date of Patent: Jul. 14, 2020

(54) STABILIZED POLYMERIC CARRIERS FOR THERAPEUTIC AGENT DELIVERY

(71) Applicant: University of Washington, Seattle, WA (US)

(72) Inventors: Patrick S. Stayton, Seattle, WA (US); Anthony J. Convertine, Seattle, WA (US); Daniel M. Ratner, Seattle, WA (US); Debobrato Das, Santa Clara, CA (US); Selvi Srinivasan, Seattle, WA (US)

(73) Assignee: University of Washington, Seattle, WA (US)

( * ) Notice: Subject to any disclaimer, the term of this patent is extended or adjusted under 35 U.S.C. 154(b) by 0 days.

(21) Appl. No.: 15/526,274

(22) PCT Filed: Nov. 12, 2015

(86) PCT No.: PCT/US2015/060450
§ 371 (c)(1),
(2) Date: May 11, 2017

(87) PCT Pub. No.: WO2016/077625
PCT Pub. Date: May 19, 2016

(65) Prior Publication Data
US 2018/0043029 A1    Feb. 15, 2018

Related U.S. Application Data

(63) Continuation-in-part of application No. PCT/US2014/065292, filed on Nov. 12, 2014.

(60) Provisional application No. 62/252,079, filed on Nov. 6, 2015, provisional application No. 62/107,643, filed on Jan. 26, 2015, provisional application No. 62/078,901, filed on Nov. 12, 2014.

(51) Int. Cl.
| | |
|---|---|
| *A61K 47/58* | (2017.01) |
| *A61K 47/60* | (2017.01) |
| *A61K 47/65* | (2017.01) |
| *A61K 9/14* | (2006.01) |
| *C08K 5/19* | (2006.01) |
| *A61K 47/69* | (2017.01) |
| *C08K 5/36* | (2006.01) |
| *C08K 5/49* | (2006.01) |
| *A61K 31/47* | (2006.01) |
| *A61K 31/496* | (2006.01) |

(52) U.S. Cl.
CPC ............. *A61K 47/60* (2017.08); *A61K 9/146* (2013.01); *A61K 47/58* (2017.08); *A61K 47/65* (2017.08); *A61K 47/6907* (2017.08); *C08K 5/19* (2013.01); *C08K 5/36* (2013.01); *C08K 5/49* (2013.01); *A61K 31/47* (2013.01); *A61K 31/496* (2013.01); *A61K 2300/00* (2013.01)

(58) Field of Classification Search
CPC .. A61K 2300/00; A61K 31/47; A61K 31/496; A61K 31/58; A61K 31/60
See application file for complete search history.

(56) References Cited

U.S. PATENT DOCUMENTS

| | | | |
|---|---|---|---|
| 6,372,205 B1 * | 4/2002 | Duncan | |
| 7,737,108 B1 | 6/2010 | Hoffman et al. | |
| 8,318,816 B2 | 11/2012 | Hoffman et al. | |
| 2004/0010864 A1 | 1/2004 | Vic et al. | |
| 2010/0203149 A1 | 8/2010 | Radosz et al. | |
| 2011/0142951 A1 * | 6/2011 | Johnson | |
| 2012/0009145 A1 | 1/2012 | Slobodkin et al. | |
| 2012/0070383 A1 | 3/2012 | Almutairi et al. | |
| 2012/0093733 A1 | 4/2012 | Malecki et al. | |
| 2012/0321719 A1 | 12/2012 | McDonnell et al. | |
| 2013/0183379 A1 | 7/2013 | Devore et al. | |
| 2013/0259924 A1 | 10/2013 | Bancel et al. | |
| 2014/0161893 A1 | 6/2014 | Shen et al. | |
| 2014/0221577 A1 | 8/2014 | Jiang et al. | |
| 2014/0235790 A1 | 8/2014 | Stayton et al. | |

FOREIGN PATENT DOCUMENTS

| | | |
|---|---|---|
| WO | 2006/039659 A1 | 4/2006 |
| WO | 2010/053596 A1 | 5/2010 |
| WO | 2012/024634 A3 | 2/2012 |
| WO | 2013/110028 A1 | 7/2013 |

OTHER PUBLICATIONS

Stenzel et al. (Biomacromolecules, pp. 1738-1751, Published Jan. 27, 2011) (Year: 2011).*
Huynh (Macromolecules, pp. 7888-7900, Published Sep. 22, 2011) (Year: 2011).*
Allen, T.M., and P.R. Cullis, "Liposomal Drug Delivery Systems: From Concept to Clinical Applications," Advanced Drug Delivery Reviews 65(1)36-48, Jan. 2013.
Alley, S.C., et al., "Contribution of Linker Stability to the Activities of Anticancer Immunoconjugates," Bioconjugate Chemistry 19(3):759-765, Mar. 2008.
Armstrong, D.K., et al., "Intraperitoneal Cisplatin and Paclitaxel in Ovarian Cancer," New England Journal of Medicine 354(1):34-43, Jan. 2006.
Authier, F., et al., "Negative Regulation of Epidermal Growth Factor Signaling by Selective Proteolytic Mechanisms in the Endosome Mediated by Cathepsin B," Journal of Biological Chemistry 274(47):33723-33731, Nov. 1999.
Barenholz, Y.C., "Doxil® —The First FDA-Approved Nano-Drug: Lessons Learned," Journal of Controlled Release 160(2):117-134, Jun. 2012.

(Continued)

*Primary Examiner* — Alma Pipic
(74) *Attorney, Agent, or Firm* — Christensen O'Connor Johnson Kindness PLLC

(57) ABSTRACT

Polymeric carriers for the delivery of therapeutic agents and methods for making and using the same. The polymeric carriers include copolymers, diblock copolymers, polymeric architectures that include the copolymers and diblock copolymers, and particles assemblies comprising the copolymers, diblock copolymers, and polymeric architectures that include the copolymers.

19 Claims, 28 Drawing Sheets

(56) References Cited

OTHER PUBLICATIONS

Becattini, B., et al., "Rational Design and Real Time, In-Cell Detection of the Proapoptotic Activity of a Novel Compound Targeting Bcl-XL," Chemistry & Biology 11(3):389-395, Mar. 2004.
Beeching, N.J., et al., "Biological Warfare and Bioterrorism," BMJ 324(7333):336-339, Feb. 2002.
Bierguig, G.Y., et al., "Intracellular Delivery System for Antibody-Peptide Drug Conjugates," Molecular Therapy 23(5):907-917, May 2015.
Blum, J.S., et al., "Proteolytic Cleavage of Ricin A Chain in Endosomal Vesicles," Journal of Biological Chemistry 266(33):22091-22095, Nov. 1991.
Boyer, C., et al., "Building Nanostructures Using Raft Polymerization," Journal of Polymeric Science Part A: Polymeric Chemistry 49(3):551-595, Feb. 2011.
Browne, S.P., et al., "The Influence of Plasma Butyrylcholinesterase Concentration on the In Vitro Hydrolysis of Cocaine in Human Plasma," Biopharmaceutics & Drug Disposition 19(5):309-314, Jul. 1998.
Brunner, M., et al., "Distribution and Antimicrobial Activity of Ciprofloxacin in Human Soft Tissues," Antimicrobial Agents and Chemotherapy 43(5):1307-1309, May 1999.
Cezari, M.H.S., et al., "Cathepsin B Carboxydipeptidase Specificity Analysis Using Internally Quenched Fluorescent Peptides," Biochemistry Journal 368(Pt 1):365-369, Nov. 2002.
Chen, L., et al., "Differential Targeting of Prosurvival Bcl-2 Proteins by Their BH3-Only Ligands Allows Complementary Apoptotic Function," Molecular Cell 17(3):393-403, Feb. 2005.
Cheng, C. et al., "Multifunctional Triblock Copolymers for Intracellular Messenger RNA Delivery," Biomaterials 33(28):6868-6876, Oct. 2012.
Cheng, J., et al., "Synthesis of Linear, $\beta$-Cyclodextrin-Based Polymers and Their Camptothecin Conjugates," Bioconjugate Chemistry 14(5):1007-1017, Sep.-Oct. 2003.
Chu, D.S.H., et al., "Application of Controlled Radical Polymerization for Nucleic Acid Delivery," Accounts of Chemical Research 45(7):1089-1099, Jul. 2012. (Author Manuscript provided, PMCID: PMC3516364, available in PMC Jul. 17, 2013, 20 pages).
Chu, D.S.H., et al., "Cathepsin B-Sensitive Polymers for Compartment-Specific Degradation and Nucleic Acid Release," Journal of Controlled Release 157(3):445-454, Feb. 2012.
Cohen, N., et al., "pH and Salt Effects on Surface Activity and Self-Assembly of Copolymers Containing a Weak Polybase," Langmuir 32(36):9286-9292, Sep. 2016.
Conejos-Sánchez, I., et al., "Polymer-Doxycycline Conjugates as Fibril Disrupters: An Approach Towards the Treatment of a Rare Amyloidotic Disease," Journal of Controlled Release 198:80-90, Jan. 2015.
Convertine, A.J., et al., "Development of a Novel Endosomolytic Diblock Copolymer for siRNA Delivery," Journal of Controlled Release 133(3):221-229, Feb. 2009.
Convertine, A.J., et al., "Aqueous RAFT Polymerization of Acrylamide and N,N-Dimethylacrylamide at Room Temperature," Macromolecular Rapid Communications 26(10):791-795, May 2005.
Convertine, A.J., et al., "Direct Synthesis of Thermally Responsive DMA/NIPAM Diblock and DMA/NIPAM/DMA Triblock Copolymers via Aqueous, Room Temperature RAFT Polymerization," Macromolecules 39(5):1724-1730, Mar. 2006.
Convertine, A.J., et al., "pH-Responsive Polymeric Micelle Carriers for siRNA Drugs," Biomacromolecule 11(11):2904-2911, Nov. 2010.
Cosulich, S.C., et al., "Regulation of Apoptosis by BH3 Domains in a Cell-Free System," Current Biology 7(12):913-920, Dec. 1997.
Cotrin, S.S., et al., "Positional-Scanning Combinatorial Libraries of Fluorescence Resonance Energy Transfer Peptides to Define Substrate Specificity of Carboxydipeptidases: Assays With Human Cathepsin B," Analytical Biochemistry 335(12):244-252, Dec. 2004.

Crownover, E., et al., "RAFT-Synthesized Graft Copolymers That Enhance pH-Dependent Membrane Destabilization and Protein Circulation Times," Journal of Controlled Release 155(2):167-174, Oct. 2011.
Crownover, E.F., et al., "pH-Responsive Polymer—Antigen Vaccine Bioconjugates," Polymer Chemistry 2(7):1499-1504, 2011.
Currie, B.J., et al., "The Epidemiology and Clinical Spectrum of Melioidosis: 540 Cases From the 20 Year Darwin Prospective Study," PLOS Neglected Tropical Diseases 4(11):e900, Nov. 2010, 11 pages.
De, P., and B.S. Sumerlin, "Precision Control of Temperature Response by Copolymerization of Di(Ethylene Glycol) Acrylate and an Acrylamide Comonomer," Macromolecular Chemistry and Physics 214(2):272-279, Jan. 2013.
Delgado-Soler, L., et al., "Molecular Determinants of Bim(BH3) Peptide Binding to Pro-Survival Proteins," Journal of Chemical Information and Modeling 52(8):2107-1118, Aug. 2012.
Dennis, D.T., et al., "Tularemia as a Biological Weapon," Journal of the American Medical Association 285(21):2763-2773, Jun. 2001.
Dizman, B., et al., "Synthesis, Characterization, and Antibacterial Activities of a Novel Methacrylate Polymers Containing Norfloxacin," Biomacromolecules 6(1):514-520, Jan.-Feb. 2005.
Doronina, S.O., et al., "Development of Potent Monoclonal Antibody Auristatin Conjugates for Cancer Therapy," Nature Biotechnology 21(7):778-784, Jul. 2003; Erratum, Nature Biotechnology 21(8):941, Aug. 2003, 1 page.
Dubowchik, G.M., et al., "Cathepsin B-Labile Dipeptide Linkers for Lysosomal Release of Doxorubicin From Internalizing Immunoconjugates: Model Studies of Enzymatic Drug Release and Antigen-Specific in Vitro Anticancer Activity," Bioconjugate Chemistry 13(4):855-869, Jul.-Aug. 2002.
Dubowchik, G.M., and R.A. Firestone, "Cathepsin B-Sensitive Dipeptide Prodrugs. 1. A Model Study of Structural Requirements for Efficient Release of Doxorubicin," Bioorganic & Medicinal Chemistry Letters 8(23):3341-3346, Dec. 1998.
Ducry L., and B. Stump, "Antibody—Drug Conjugates: Linking Cytotoxic Payloads to Monoclonal Antibodies," Bioconjugate Chemistry 21(1):5-13, Jan. 2010.
Duncan, R., and J. Kopeček, "Soluble Synthetic Polymers as Potential Drug Carriers," Advances in Polymer Science 57:51-57, 1984.
Duvall, C.L., et al., "Intracellular Delivery of a Proapoptotic Peptide via Conjugation to a RAFT Synthesized Endosomolytic Polymer," Molecular Pharmaceutics 7(2):468-476, 2010. (Author Manuscript provided, PMCID: PMC2849913, available in PMC Apr. 5, 2011, 20 pages).
Edwards, D.A., et al., "Large Porous Particles for Pulmonary Drug Delivery," Science 276(5320):1868-1871, Jun. 1997.
Eliasof, S., et al., "Correlating Preclinical Animal Studies and Human Clinical Trials of a Multifunctional, Polymeric Nanoparticle," Proceedings of the National Academy of Sciences of the USA (PNAS) 110(37):15127-15132, Sep. 2013.
Filho, R.P., et al., "Design, Synthesis, and In Vivo Evaluation of Oxamniquine Methacrylate and Acrylamide Prodrugs," Biorganic & Medicinal Chemistry 15(3):1229-1236, Feb. 2007.
Garraffo, R., et al., "In Vitro and In Vivo Ciprofloxacin Pharmacokinetics in Human Neutrophils," Antimicrobial Agents and Chemotherapy 35(11):2215-2218, Nov. 1991.
Gascoyne, R.D., et al., "Prognostic Significance of Bcl-2 Protein Expression and Bcl-2 Gene Rearrangement in Diffuse Aggressive Non-Hodgkin's Lymphoma," Blood 90(1):244-251, Jul. 1997.
Gray, J.C., and J.A. Kohler, "Immunotherapy for Neuroblastoma: Turning Promise Into Reality," Pediatric Blood Cancer 53(6):931-940, Dec. 2009.
Greenwald, R.B., et al., "Drug Delivery Systems: Water Soluble Taxol 2-Poly(ethylene glycol) Ester Prodrugs—Design and In Vivo Effectiveness," Journal of Medicinal Chemistry 39(2):424-431, Jan. 1996.
Han, H., and M.E. Davis, "Single-Antibody, Targeted Nanoparticle Delivery of Camptothecin," Molecular Pharmaceutics 10(7):2558-2567, Jul. 2013.
Hanahan, D., and R.A. Weinberg, "Hallmarks of Cancer: The Next Generation," Cell 144(5):646-674, Mar. 2011.

(56) References Cited

OTHER PUBLICATIONS

Hao, X., et al., "Dendrimers as Scaffolds for Multifunctional Reversible Addition-Fragmentation Chain Transfer Agents: Syntheses and Polymerization," Journal of Polymer Science: Part A: Polymer Chemistry 42(23):5877-5890, Dec. 2004.
Haraga, A., et al., "Burkholderia thailandensis as a Model System for the Study of the Virulence-Associated Type III Secretion System of Burkholderia pseudomallei," Infection and Immunity 76(11):5402-5411, Nov. 2008.
Verhaegen, M., et al., "A Novel BH3 Mimetic Reveals a Mitogen-Activated Protein Kinase-Dependent Mechanism of Melanoma Cell Death Controlled by p53 and Reactive Oxygen Species," Cancer Research 66(23):11348-11359, Dec. 2006.
Vicent, M.J., and R. Duncan, "Polymer Conjugates: Nanosized Medicines for Treating Cancer," Trends in Biotechnology 24(1):39-47, Jan. 2006.
Wayakanon, K., et al., "Polymersome-Mediated Intracellular Delivery of Antibiotics to Treat Porphyromonas gingivalis-Infected Oral Epithelial Cells," FASEB Journal 27(11):4455-4465, Nov. 2013.
van de Wetering, P., et al., "A Mechanistic Study of the Hydrolytic Stability of Poly(2-(dimethylamino)ethyl methacrylate)," Macromolecules 31(23):8063-8068, Nov. 1998.
Wiersinga, W.J., et al., "Melioidosis," New England Journal of Medicine 367(11):1035-1044, Sep. 2012.
Wilson, J.T., et al., "pH-Responsive Nanoparticle Vaccines for Dual-Delivery of Antigens and Immunostimulatory Oligonucleotides," ACS Nano 7(5):3912-3925, May 2013.
Wong, J.P., et al., "Liposome Delivery of Ciprofloxacin Against Intracellular Francisella tularensis Infection," Journal of Controlled Release 92(3):265-273, Oct. 2003.
Woo, G.L.Y., et al., "Synthesis and Characterization of a Novel Biodegradable Antimicrobial Polymer," Biomaterials 21(12):1235-1246, Jun. 2000.
Wu, P., and D.W. Grainger, "Drug/Device Combinations for Local Drug Therapies and Infection Prophylaxis," Biomaterials 27(11):2450-2467, Apr. 2006.
Wu, S.-S., et al., "Analysis of Ciprofloxacin by a Simple High-Performance Liquid Chromatography Method," Journal of Chromatographic Science 46(6):490-495, Jul. 2008.
Xia, T., et al., "Cationic Polystyrene Nanosphere Toxicity Depends on Cell-Specific Endocytic and Mitochondrial Injury Pathways," ACS Nano 2(1):85-96, Jan. 2008.
Xie, H., et al., "Pharmacokinetics and Biodistribution of the Antitumor Immunoconjugate, Cantuzumab Mertansine (huC242-DM1), and Its Two Components in Mice," Journal of Pharmacology and Experimental Therapeutics 308(3):1073-1082, Mar. 2004.
Xiong, M.-H., et al., "Bacteria-Responsive Multifunctional Nanogel for Targeted Antibiotic Delivery," Advanced Materials 24(46):6175-6180, Dec. 2012.
Xu, J., et al., "Synthesis of Dendritic Carbohydrate End-Functional Polymers via RAFT: Versatile Multi-Functional Precursors for Bioconjugations," Journal of Polymer Science Part A: Polymer Chemistry 47(17):4302-4313, Sep. 2009.
Yu, S.S., et al., "Size- and Charge-Dependent Non-Specific Uptake of PEGylated Nanoparticles by Macrophages," International Journal of Nanomedicine 7:799-813, 2012.
Zhang, L., et al., "Acid-Degradable Core-Crosslinked Micelles Prepared from Thermosensitive Glycopolymers Synthesized via RAFT Polymerization," Macromolecular Rapid Communications 29(2):123-129, Jan. 2008.
Zhang, Y., et al., "Trigger-Responsive Chain-Shattering Polymers," Polymer Chemistry 4(2):224-228, Jan. 2013.
Zhang, L., and A. Eisenberg, "Thermodynamic vs Kinetic Aspects in the Formation and Morphological Transitions of Crew-Cut Aggregates Produced by Self-Assembly of Polystyrene-b-poly(acrylic acid) Block Copolymers in Dilute Solution," Macromolecules 32(7):2239-2249, Apr. 1999.
Zheng, G., and C. Pan, "Preparation of Star Polymers Based on Polystyrene or Poly(styrene-b-N-isopropyl acrylamide) and Divinylbenzene via Reversible Addition-Fragmentation Chain Transfer Polymerization," Polymer 46(8):2802-2810, Mar. 2005.
Hasnain, S., et al., "Characterization of Recombinant Rat Cathepsin B and Nonglycosylated Mutants Expressed in Yeast," Journal of Biological Chemistry 267(7):4713-4721, Mar. 1992.
Henry, S M., et al., "End-Functionalized Polymers and Junction-Functionalized Diblock Copolymers Via RAFT Chain Extension With Maleimido Monomers," Bioconjugate Chemistry 20(6):1122-1128, Jun. 2009.
Hong, C.-Y., et al., "Synthesis of Water-Soluble Multiwalled Carbon Nanotubes With Grafted Temperature-Responsive Shells by Surface RAFT Polymerization," Chemical Materials 17(9):2247-2254, May 2005.
Huang, C., et al., "Polymeric Nanoparticles With Encapsulated Superparamagnetic Iron Oxide and Conjugated Cisplatin for Potential Bladder Cancer Therapy," Biomacromolecules 13(8):2513-2520, Aug. 2012.
Joudeh, J., and D. Claxton, "Obatoclax Mesylate: Pharmacology and Potential for Therapy of Hematological Neoplasms," Expert Opinion on Investigational Drugs 21(3):363-373, Mar. 2012.
Kashiwagi, H., et al., "TAT-Bim Induces Extensive Apoptosis in Cancer Cells," Annals of Surgical Oncology 14(5):1763-1771, May 2007.
Keddie, D.J., "A Guide to the Synthesis of Block Copolymers Using Reversible-Addition Fragmentation Chain Transfer (RAFT) Polymerization," Chemical Society Reviews 43(2):496-505, Jan. 2014.
Keddie, D.J., et al., "Switchable Reversible Addition Fragmentation Chain Transfer (RAFT) Polymerization in Aqueous Solution, N,N-Dimethylacrylamide," Macromolecules 44(17):6738-6745, Sep. 2011.
Keller, S., et al., "Neutral Polymer Micelle Carriers With pH-Responsive, Endosome-Releasing Activity Modulate Antigen Trafficking to Enhance CD8 T-Cell Responses," Journal of Controlled Release 191:24-33, Oct. 2014. (Author Manuscript provided, PMCID: PMC4156909, available in PMC Oct. 10, 2015, 24 pages).
Kenawy, E.R., et al., "The Chemistry and Applications of Antimicrobial Polymers: A State-of-the-Art Review," Biomacromolecules 8(5):1359-1384, May 2007.
Kern, H.B., et al., "Enzyme-Cleavable Polymeric Micelles for the Intracellular Delivery of Proapoptotic Peptides," Molecular Pharmaceutics 14(5):1450-1459, May 2017.
Khandare, J., and T. Minko, "Polymer-Drug Conjugates: Progress in Polymeric Prodrugs," Progress in Polymer Science 31(4):359-397, Apr. 2006.
Kim, S., et al., "Overcoming the Barriers in Micellar Drug Delivery: Loading Efficiency, in Vivo Stability, and Micelle-Cell Interaction," Expert Opinion on Drug Delivery 7(1):49-62, Jan. 2010.
Kitada, S., et al., "Discovery, Characterization, and Structure-Activity Relationships Studies of Proapoptotic Polyphenols Targeting B-Cell Lymphocyte/Leukemia-2 Proteins," Journal of Medicinal Chemistry 46(20):4259-4264, Sep. 2003.
Konkolewicz, D., et al., "Dendritic and Hyperbranched Polymers From Macromolecular Units: Elegant Approaches to the Synthesis of Functional Polymers," Macromolecules 44(18):7067-7087, Sep. 2011.
Kost, J., and R. Langer, "Responsive Polymeric Delivery Systems," Advanced Drug Delivery Reviews 64(Suppl.):327-341, Dec. 2012.
Kranz, H., and R. Bodmeier, "A Novel in situ Forming Drug Delivery System for Controlled Parenteral Drug Delivery," International Journal of Pharmaceutics 332(1-2):107-114, Mar. 2007.
Kuchta, F.-D., et al., "Propagation Kinetics of Acrylic and Methacrylic Acid in Water and Organic Solvents Studied by Pulsed-Laser Polymerization," Macromolecules 33(10):3641-3649, May 2000.
LaBelle, J.L., et al., "A Stapled BIM Peptide Overcomes Apoptotic Resistance in Hematologic Cancers," Journal of Clinical Investigation 122(6):2018-2031, Jun. 2012.
Lacik, I., et al., "Propagation Rate Coefficient of Free-Radical Polymerization of Partially and Fully Ionized Methacrylic Acid in Aqueous Solution," Macromolecules 42(20):7753-7761, Oct. 2009.
Lane, D.D., et al., "Dynamic Intracellular Delivery of Antibiotics via pH-Responsive Polymersomes," Polymer Chemistry 6(8):1255-1266, Feb. 2015. (Author Manuscript provided, PMCID: PMC4470576, available in PMC Feb. 28, 2016, 26 pages).

(56) References Cited

OTHER PUBLICATIONS

Lane, D.D., et al., "Well-Defined Single Polymer Nanoparticles for the Antibody-Targeted Delivery of Chemotherapeutic Agents," Polymer Chemistry 6(8):1286-1299, Feb. 2015.

Langowska, K., et al., "Polymer Nanoreactors Shown to Produce and Release Antibiotics Locally," Chemical Communications 49(2):128-130, Jan. 2013.

Lautwein, A., et al., "Human B Lymphoblastoid Cells Contain Distinct Patterns of Cathepsin Activity in Endocytic Compartments and Regulate MHC Class II Transport in a Cathepsin S-Independent Manner," Journal of Leukocyte Biology 75(5):844-855, May 2004.

Lee, C.C., et al., "A Single Dose of Doxorubicin-Functionalized Bow-Tie Dendrimer Cures Mice Bearing C-26 Colon Carcinomas," Proceedings of the National Academy of Sciences of the USA (PNAS) 103(45):16649-16654, Nov. 2006.

Lessene, G., et al., "BCL-2 Family Antagonists for Cancer Therapy," Nature Reviews: Drug Discovery 7(12):989-1000, Dec. 2008.

Li, A., et al., "One-Pot, Facile Synthesis of Well-Defined Molecular Brush Copolymers by a Tandem RAFT and ROMP, 'Grafting-Through' Strategy," Journal of Polymer Science Part A: Polymer Chemistry 50(9):1681-1688, May 2012.

Liaw, D.-J., et al., "Macromolecular Microstructure, Reactivity Ratio and Viscometric Studies of Water-Soluble Cationic and/or Zwitterionic Copolymers," Polymer 41(16):6123-6131, Jul. 2000.

Liu, J., et al., "An Approach to Biodegradable Star Polymeric Architectures Using Disulfide Coupling," Chemical Communications 48:6582-6584, Dec. 2008.

Liu, J., et al., "RAFT Controlled Synthesis of Six-Armed Biodegradable Star Polymeric Architectures via a 'Core-First' Methodology," Polymer 50(19):4455-4463, Sep. 2009.

Lokitz, B.S., et al., "Responsive Nanoassemblies via Interpolyelectrolyte Complexation of Amphiphilic Block Copolymer Micelles," Macromolecules 39(25):8594-8602, Dec. 2006.

Lomonosova, E., and G. Chinnadurai, "BHC-Only Proteins in Apoptosis and Beyond: An Overview," Oncogene 27(Suppl. 1):S2-S19, Dec. 2009.

Lu, J., et al., "Stability of Self-Assembled Polymeric Micelles in Serum," Macromolecules 44(15):6002-6008, Aug. 2011.

Lundy, B.B., et al., "Neutral Polymeric Micelles for RNA Delivery," Bioconjugate Chemistry 24(3):398-407, Mar. 2013.

Lutz, J.-F., "Polymerization of Oligo(Ethylene Glycol) (Meth)Acrylates: Toward New Generations of Smart Biocompatible Materials," Journal of Polymer Science: Part A: Polymer Chemistry 46(11):3459-3470, Jun. 2008.

Manganiello, M.J., et al., "Diblock Copolymers With Tunable pH Transitions for Gene Delivery," Biomaterials 33(7):2301-2309, Mar. 2012.

Manoharan, I., et al., "A Medical Health Report on Individuals With Silent Butyrylcholinesterase in the Vysya Community of India," Clinica Chimica Acta 378(1-2):128-135, Mar. 2007.

Mayadunne, R.T.A., et al., "Living Radical Polymerization With Reversible Addition-Fragmentation Chain Transfer (RAFT Polymerization) Using Dithiocarbamates as Chain Transfer Agents," Macromolecules 32(21):6977-6980, Oct. 1999.

Meister, A., and M.E. Anderson, "Glutathione," Annual Review of Biochemistry 52:711-760, 1983.

Miller, T., et al., "Premature Drug Release of Polymeric Micelles and Its Effects on Tumor Targeting," International Journal of Pharmaceutics 445(1-2):117-124, Mar. 2013.

Moad, G., et al., "Advances in RAFT Polymerization: The Synthesis of Polymers With Defined End-Groups," Polymer 46(19):8458-8468, Sep. 2005.

Moad, G., et al., "Living Radical Polymerization by the RAFT Process—A Third Update," Australian Journal of Chemistry 65(8):985-1076, Sep. 2012.

Mohamed, M.M., and B.F. Sloane, "Cysteine Cathepsins: Multifunctional Enzymes in Cancer," Nature Reviews: Cancer 6(10):764-775, Oct. 2006.

Moreau, C., et al., "Minimal BH3 Peptides Promote Cell Death by Antagonizing Anti-Apoptotic Proteins," Journal of Biological Chemistry 278(21):19426-19435, May 2003.

Morgan, R.J., Jr., et al., "Ovarian Cancer, Version 2.2013: Featured Updates to the NCCN Guidelines," Journal of the National Comprehensive Cancer Network (JNCCN) 11(10):1199-1209, Oct. 2013.

Nese, A., et al., "Synthesis of Poly(vinyl acetate) Molecular Brushes by a Combination of Atom Transfer Radical Polymerization (ATRP) and Reversible Addition-Fragmentation Chain Transfer (RAFT) Polymerization," Macromolecules 43(9):4016-4019, May 2010.

Nguyen, M., et al., "Small Molecule Obatoclax (GX15-070) Antagonizes MCL-1 and Overcomes MCL-1-Mediated Resistance to Apoptosis," Proceedings of the National Academy of Sciences of the USA (PNAS) 104(49):19512-19517, Dec. 2007.

O'Brien, M.E.R., et al., "Reduced Cardiotoxicity and Comparable Efficacy in a Phase III Trial of Pegylated Liposomal Doxorubicin HCI (Caelyx™/Doxile®) Versus Conventional Doxorubicin for First-Line Treatment of Metastatic Breast Cancer," Annals of Oncology 15(3):440-449, Mar. 2004.

Oerlemans, C., et al., "Polymeric Micelles in Anticancer Therapy: Targeting, Imaging and Triggered Release," Pharmaceutical Research 27(12):2569-2589, Dec. 2010.

Oltersdorf, T., et al., "An Inhibitor of Bcl-2 Family Proteins Induces Regression of Solid Tumours," Nature Letters 435(7042):677-681, Jun. 2005.

Babazadeh, M., "Synthesis and Study of Controlled Release of Ibuprofen From the New Acrylic Type Polymers," International Journal of Pharmaceutics 316(1-2):68-73, Jun. 2006.

Bédouet, L., et al., "Synthesis of Hydrophilic Intra-Articular Microspheres Conjugated to Ibuprofen and Evaluation of Anti-Inflammatory Activity on Articular Explants," International Journal of Pharmaceutics 459(1-2):51-61, Jan. 2014.

Cai, X., et al., "Chemo-Enzymatic Synthesis of Optically Active Polymeric Prodrug of Naproxen, Ketoprofen and Ibuprofen," Polymer 47(19):6491-6495, Sep. 2006.

Cai, X.-Q., et al., "The Preparation of Polymerizable, Optically Active Non-Steroidal Anti-Inflammatory Drugs Derivatives by Irreversible Enzymatic Methods," Journal of Molecular Catalysis B. Enzymatic 40(1-2):51-57, May 2006.

Cao, Y., and W. He, "Water-Soluble Antioxidant Derivative Poly(triethylene glycol methyl acrylate-co-α-tocopheryl acrylate) as a Potential Prodrug to Enable Localized Neuroprotection," Acta Biomaterialia 9(1):4558-4568, Jan. 2013.

Cho, S.H., et al., "Antitumor Activities of Poly(methacryloyl-D-mlucosamine) Prodrugs," Korea Polymer Journal 6(2):188-192, Jun. 1998.

Das, D., et al., "RAFT Polymerization of Ciprofloxacin Prodrug Monomers for the Controlled Intracellular Delivery of Antibiotics," Polymer Chemistry 7(4):826-837, Jan. 2016.

Davaran, S., and A.A. Entezami, "Acrylic Type Polymers Containing Ibuprofen and Indomethacin With Difunctional Spacer Group: Synthesis and Hydrolysis," Journal of Controlled Release 47(1):41-49, Jul. 1997.

Davaran, S., et al., "Release of 5-Amino Salicylic Acid From Acrylic Type Polymeric Prodrugs Designed for Colon-Specific Drug Delivery," Journal of Controlled Release 58(3):279-287, Apr. 1999.

Haba, K., et al., "Single-Triggered Trimeric Prodrugs," Angewandte Chemie International Edition 117(5):726-730, Jan. 2005.

Hasegawa, U., et al., "Preparation of Well-Defined Ibuprofen Prodrug Micelles by RAFT Polymerization," Biomacromolecules 14(9):3314-3320, Sep. 2013.

Hu, X., et al., "Cell-Penetrating Hyperbranched Polyprodrug Amphiphiles for Synergistic Reductive Milieu-Triggered Drug Release and Enhanced Magnetic Resonance Signals," Journal of the American Chemical Society 137(1):362-368, Jan. 2015.

International Preliminary Report on Patentability dated May 16, 2017, issued in International Application No. PCT/US2015/060450, filed Nov. 12, 2015, 15 pages.

International Search Report and Written Opinion dated Jan. 21, 2016, issued in International Application No. PCT/US2015/060450, filed Nov. 12, 2015, 18 pages.

(56) References Cited

OTHER PUBLICATIONS

Kondo, S.-I., et al., "Mechanochemical Solid-State Polymerization (X): The Influence of Copolymer Structure in Copolymeric Prodrugs on the Nature of Drug Release," Chemical and Pharmaceutical Bulletin 48(12):1882-1885, Dec. 2000.

Kondo, S.I., et al., "Mechanochemical Solid-State Polymerization. VII. The Nature of Hydrolysis of Novel Polymeric Prodrugs Prepared by Mechanochemical Copolymerization," Chemical and Pharmaceutical Bulletin 42(12):2412-2417, 1994.

Kryger, M.B.L., et al., "Macromolecular Prodrugs for Controlled Delivery of Ribavirin," Macromolecular Bioscience 14(2):173-185, Feb. 2014.

Kryger, M.B.L., et al., "Macromolecular Prodrugs of Ribavirin Combat Side Effects and Toxicity With No Loss of Activity of the Drug," Chemical Communications 49(26):2643-2645, Apr. 2013.

Kuzuya, M., and S.-I. Kondo, "The Nature of Hydrolysis of Novel Methacryloyl Polymeric Prodrugs Prepared by Mechanochemical Solid State Polymerization," Chemical and Pharmaceutical Bulletin 39(11):3018-3022, 1991.

Kuzuya, M., et al., "A New Development of Mechanochemical Solid-State Polymerization of Vinyl Monomers: Prodrug Syntheses and Its Detailed Mechanistic Study," Macromolecules 24(14):4047-4053, Jul. 1991.

Leonard, J.K., et al., "Polyethylene Prodrugs Using Precisely Placed Pharmaceutical Agents," Macromolecular Chemistry and Physics, Macromolecular Chemistry Physics 211(2):154-165, Jan. 2010.

Li, X., et al., "Chemoenzymatic Synthesis, Characterization, and Controlled Release of Functional Polymeric Prodrugs With Acyclovir as Pendant," Journal of Applied Polymer Science 108(1):431-437, Apr. 2008.

Li, X., et al., "Controllable Synthesis of Polymerizable Ester and Amide Prodrugs of Acyclovir by Enzyme in Organic Solvent," Bioorganic & Medicinal Chemistry Letters 14(10):3377-3382, May 2006.

Liu, J., et al., "Ring-Opening Polymerization of Prodrugs: A Versatile Approach to Prepare Well-Defined Drug-Loaded Nanoparticles," Angewandte Communications International Edition 54(3):1002-1006, Jan. 2015.

Mandal, B., et al., "Core-Shell-Type Lipid-Polymer Hybrid Nanoparticles as a Drug Delivery Platform," Nanomedicine: Nanotechnology, Biology, and Medicine 9(4):474-491, May 2013.

Miyandoab, S.A., and M. Babazadeh, "Indomethacin Macromolecular Prodrugs: Synthesis, Characterization and in vitro Evaluation," Der Pharma Chemica 7(1):148-155, 2015.

París, R., et al., "Synthesis and Characterization of a New Acrylic Polymeric Ibuprofen Prodrug," Journal of Applied Polymer Science 117(6):3271-3276, Sep. 2010.

Parise Filho, R., et al., "Design, Synthesis, and In Vivo Evaluation of Oxamniquine Methacrylate and Acrylamide Prodrugs," Bioorganic & Medicinal Chemistry Letters 15(3):1229-1236, Feb. 2007.

Quan, J., et al., "Controllable Selective Enzymatic Synthesis of N-acyl and O-Acylpropranolol Vinyl Esters and Preparation of Polymeric Prodrug of Propranolol," Journal of Molecular Catalysis B: Enzymatic 44(1):1-7, Jan. 2007.

Quan, J., et al., "Synthesis and Characterization of Optically Active Macromolecular Prodrugs With Chemo-Enzymatic Protocol," Proceedings of the Third International Conference on Bioinformatics and Biomedical Engineering (ICBBE 2009), Beijing, Jun. 11-13, 2009, pp. 1-4.

Smith, A.A.A., et al., "Macromolecular Prodrugs of Ribavirin: Towards a Treatment for Co-Infection With HIV and HCV," Chemical Science 6(1):264-269, Jan. 2015.

Wang, L.F., et al., "Synthesis and Properites of a Naproxen Polymeric Prodrug," Journal of Pharmacy and Pharmacology 54(8):1129-1135, Aug. 2002.

Wang, N., et al., "Controllable Selective Synthesis of a Polymerizable Prodrug of Cytarabine by Enzymatic and Chemical Methods," Bioorganic and Medicinal Chemistry Letters 15(18):4064-4067, Sep. 2005.

Zuwala, K., et al., "Polymers Fight HIV: Potent (Pro)Drugs Identified Through Parallel Automated Synthesis," Advanced Healthcare Materials 4(1):46-50, Jan. 2015.

International Search Report and Written Opinion dated Apr. 29, 2015, issued in International Application No. PCT/US2014/065292, filed Nov. 12, 2014, 16 pages.

International Preliminary Report on Patentability dated Oct. 23, 2015, issued in International Application No. PCT/US2014/065292, filed Nov. 12, 2014, 8 pages.

Ong, H.X., et al., "In Vitro and Ex Vivo Methods Predict the Enhanced Lung Residence Time of Liposomal Ciprofloxacin Formulations for Nebulisation," European Journal of Pharmaceutics and Biopharmaceutics 86(1):83-89, Jan. 2014.

Palanca-Wessels, M.C., et al., "Anti-CD22 Antibody Targeting of pH-Responsive Micelles Enhances Small Interfering RNA Delivery and Gene Silencing in Lymphoma Cells," Molecular Therapy 19(8):1529-1537, Aug. 2011.

Pegoraro, C., et al., "Enhanced Drug Delivery to Melanoma Cells Using PMPC-PDPA Polymersomes," Cancer Letters 334(2):328-337, Jul. 2013.

Peirs, S., et al., "ABT-199 Mediated Inhibition of BCL-2 as a Novel Therapeutic Strategy in T-Cell Acute Lymphoblastic Leukemia," Blood 124(25):3738-3747, Dec. 2014.

Pohlit, H., et al., "Biodegradable pH-Sensitive Poly(ethylene glycol) Nanocarriers for Allergen Encapsulation and Controlled Release," Biomacromolecules 16(10):3103-3111, Oct. 2015.

Procko, E., et al., "A Computationally Designed Inhibitor of an Epstein-Barr Viral Bcl-2 Protein Induces Apoptosis in Infected Cells," Cell 157(7):1644-1656, Jun. 2014.

Quek, J.Y., et al., "RAFT Synthesis and Aqueous Solution Behavior of Novel pH- and Thermo-Responsive (Co) Polymers Derived From Reactive Poly(2-vinyl-4,4-dimethylazlactone) Scaffolds," Macromolecules 46(18):7290-7302, Sep. 2013.

Radovic-Moreno, A.F., et al., "Surface Charge-Switching Polymeric Nanoparticles for Bacterial Cell Wall-Targeted Delivery of Antibiotics," ACS Nano 6(5):4279-4287, May 2012. (Author Manuscript provided, PMCID: PMC3779925, available in PMC Sep. 23, 2013, 18 pages).

Reed, J.C., et al., "Regulation of Chemoresistance by the bcl-2 Oncoprotein in Non-Hodgkin's Lymphoma and Lymphocytic Leukemia Cell Lines," Annals of Oncology 5 (Suppl. 1):S61-S65, 1994.

Říhová, B., et al., "Doxorubicin Bound to a HPMA Copolymer Carrier Through Hydrazone Bond Is Effective Also in a Cancer Cell Line With a Limited Content of Lysosomes," Journal of Controlled Release 74(1-3):225-232, Jul. 2001.

Roberts, R., "Lysosomal Cysteine Proteases: Structure, Function and Inhibition of Cathepsins," Drug News & Perspectives 18(10):605-614, Dec. 2005.

Robertson, J.D., et al., "pH-Sensitive Tubular Polymersomes: Formation and Applications in Cellular Delivery," ACS Nano 8(5):4650-4661, May 2014.

Roth, P.J., et al., "RAFT Polymerization and Thiol Chemistry: A Complementary Pairing for Implementing Modern Macromolecular Design," Macromolecular Rapid Communications 32(15):1123-1143, Aug. 2011.

Roy, D., et al., "Graft Polymerization: Grafting Poly(styrene) from Cellulose via Reversible Addition-Fragmentation Chain Transfer (RAFT) Polymerization," Macromolecules 38(25):10363-10372, Dec. 2005.

Roy, D., et al., "Synthesis and Characterization of Transferrin-Targeted Chemotherapeutic Delivery Systems Prepared via RAFT Copolymerization of High Molecular Weight PEG Macromonomers," Polymer Chemistry 5(5):1791-1799, Mar. 2014.

Russell, P., et al., "Comparison of Efficacy of Ciprofloxacin and Doxycycline Against Experimental Melioidosis and Glanders," Journal of Antimicrobial Chemotherapy 45(6):813-818, Jun. 2000.

Satchi-Fainaro, R., et al., "Targeting Angiogenesis With a Conjugate of HPMA Copolymer and TNP-470," Nature Medicine 10(3):255-261, Mar. 2004.

Scales, C.W., et al., "Direct, Controlled Synthesis of the Nonimmunogenic, Hydrophilic Polymer, Poly(N-(2-hydroxypropyl)methacrylamide) via RAFT in Aqueous Media," Biomacromolecules 6(4):1846-1850, Jul.-Aug. 2005.

(56) References Cited

OTHER PUBLICATIONS

Schmitt, C.J., et al., "Replacement of Conventional Doxorubicin by Pegylated Liposomal Doxorubicin Is a Safe and Effective Alternative in the Treatment of Non-Hodgkin's Lymphoma Patients With Cardiac Risk Factors," Annals in Heatology 91(3):391-397, Mar. 2012.
Seabrook, S.A., and R.G. Gilbert, "Photo-Initiated Polymerization of Acrylamide in Water," Polymer 48(16):4733-4741, Jul. 2007.
Seabrook, S.A., et al., "Pulsed Laser Polymerization Study of the Propagation Kinetics of Acrylamide in Water," Journal of Polymer Science: Part A: Polymer Chemistry 43(7):1357-1368, Apr. 2005.
Seabrook, S.A., et al., "Termination Rate Coefficients for Acrylamide in the Aqueous Phase at Low Conversion," Polymer 46(23):9562-9573, Nov. 2005.
Senter, P.D., "Potent Antibody Drug Conjugates for Cancer Therapy," Current Opinion in Clinical Biology 13(3):235-244, Jun. 2009.
Shao, L.-H., et al., "Cathepsin B Cleavable Novel Prodrug Ac-Phe-Lys-PABC-ADM Enhances Efficacy at Reduced Toxicity in Treating Gastric Cancer Peritoneal Carcinomatosis," Cancer 118:2986-2896, Jun. 2012.
Siegel, R., et al., "Cancer Statistics, 2013," CA: A Cancer Journal for Clinicians 63(1):11-30, Jan. 2013.
Sobczak, M., "Synthesis and Characterization of Polyester Conjugates of Ciprofloxacin," European Journal of Medicinal Chemistry 45(9):3844-3849, Sep. 2010.
Souers, A.J., et al., "ABT-199, a Potent and Selective BCL-2 Inhibitor, Achieves Antitumor Activity While Sparing Platelets," Nature Medicine 19(2):202-208, Feb. 2013.
Sparano, J.A., et al., "Pegylated Liposomal Doxorubicin Plus Docetaxel Significantly Improves Time to Progression Without Additive Cardiotoxicity Compared With Docetaxel Monotherapy in Patients With Advanced Breast Cancer Previously Treated With Neoadjuvant-Adjuvant Anthracycline Therapy: Results From a Randomized Phase III Study," Journal of Clinical Oncology 27(27):4522-4529, Sep. 2009.
Stachowiak, K., et al., "Fluorogenic Peptide Substrates for Carboxydipeptidase Activity of Cathepsin B," Acta Biochimica Polonica 51(1):81-92, 2004.
Stebbins, N.D., et al., "Antibiotic-Containing Polymers for Localized, Sustained Drug Delivery," Advanced Drug Delivery Reviews 78:77-87, Nov. 2014.
Stenzel, M.H., and T.P. Davis, "Star Polymer Synthesis Using Trithiocarbonate Functional β-Cyclodextrin Cores (Reversible Addition-Fragmentation Chain-Transfer Polymerization)," Journal of Polymer Science Part A: Polymer Chemistry 40(24):4498-4512, Dec. 2002.
Stenzel-Rosenbaum, M.H., et al., "Porous Polymer Films and Honeycomb Structures Made by the Self-Organization of Well-Defined Macromolecular Structures Created by Living Radical Polymerization Techniques," Angewandte Chemie International Edition 40(18):3428-3432, Sep. 2001.
Stenzel-Rosenbaum, M., et al., "Star-Polymer Synthesis via Radical Reversible Addition-Fragmentation Chain-Transfer Polymerization," Journal of Polymer Science Part A: Polymer Chemistry 39(16):2777-2783, Aug. 2001.
Stirling, D., et al., "Screening for Familial Ovarian Cancer: Failure of Current Protocols to Detect Ovarian Cancer at an Early Stage According to the International Federation of Gynecology and Obstetrics System," Journal of Clinical Oncology 23(24):5588-5596, Aug. 2005.
Strasser, A., et al., "Deciphering the Rules of Programmed Cell Death to Improve Therapy of Cancer and Other Diseases," EMBO Journal 30(18):3667-3683, Sep. 2011.
Su, Z., et al., "Detection and Monitoring of Ovarian Cancer," Clinica Chimica Acta 415:341-345, Jan. 2013.
Taft, Jr., R.W., "Polar and Steric Substituent Constants for Aliphatic and o-Benzoate Groups From Rates of Esterification and Hydrolysis of Esters," Journal of the American Chemical Society 74(12):3120-3128, Jun. 1952.
Tehler, U., et al., "Optimizing Solubility and Permeability of a Biopharmaceutics Classification System (BCS) Class 4 Antibiotic Drug Using Lipophilic Fragments Disturbing the Crystal Lattice," Journal of Medicinal Chemistry 56(6):2690-2694, Mar. 2013.
Thibault, F.M., et al., "Antibiotic Susceptibility of 65 Isolates of Burkholderia pseudomallei and Burkholderia mallei to 35 Antimicrobial Agents," Journal of Antimicrobial Chemotherapy 54(6):1134-1138, Dec. 2004.
Thomas, D.B., et al., "Hydrolytic Susceptibility of Dithioester Chain Transfer Agents and Implications in Aqueous RAFT Polymerizations," Macromolecules 37(5):1735-1741, Mar. 2004.
Thorpe, P.E., et al., "Improved Antitumor Effects of Immunotoxins Prepared With Deglycosylated Ricin A-Chain and Hindered Bisulfide Linkages," Cancer Research 48:6396-6403, Nov. 1988.
Thorpe, P.E., et al., "New Coupling Agents for the Synthesis of Immunotoxins Containing a Hindered Disulfide Bond Nith Improved Stability in Vivo," Cancer Research 47:5924-5931, Nov. 1987.
Torchilin, V.P., "Recent Approaches to Intracellular Delivery of Drugs and DNA and Organelle Targeting," Annual Review of Biomedical Engineering 8:343-375, 2006.
Treat, N.J., et al., "Guanidine-Containing Methacrylamide (Co)polymers via aRAFT: Toward a Cell-Penetrating Peptide Mimic," ACS Macro Letters 1(1):100-104, Jan. 2012.
Tse, C., et al., "ABT-263: A Potent and Orally Bioavailable Bcl-2 Family Inhibitor," Cancer Research 68(9):3421-3428, May 2008.
Uhrich, K.E., et al., "Polymeric Systems for Controlled Drug Release," Chemical Review 99(11):3181-3198, Nov. 1999.
Ulbrich, K., et al., "HPMA Copolymers With pH-Controlled Release of Doxorubicin: In Vitro Cytotoxicity and in Vivo Antitumor Activity," Journal of Controlled Release 87(1-3):33-47, Feb. 2003.
Ulrich, R.L., et al., "Characterization of the Burkholderia thailandensis SOS Response by Using Whole-Transcriptome Shotgun Sequencing," Applied and Environmental Microbiology 79(19):5830-5843, Oct. 2013.
Vandenberg, C.J., and S. Cory, "ABT-199, a New Bcl-2-Specific BH3 Mimetic, Has In Vivo Efficacy Against Aggressive Myc-Driven Mouse Lymphomas Without Provoking Thrombocytopenia," Blood 121(12):2285-2288, Mar. 2013.
Vaux, D.L., et al., "Bcl-2 Gene Promotes Haemopoietic Cell Survival and Cooperates With c-myc to Immortalize pre-B Cells," Nature 335(6189):440-442, Sep. 1988.

* cited by examiner

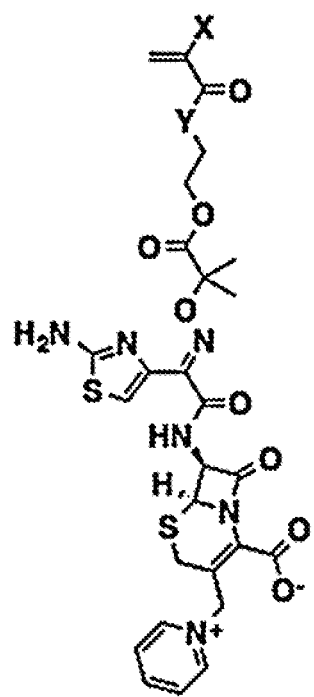
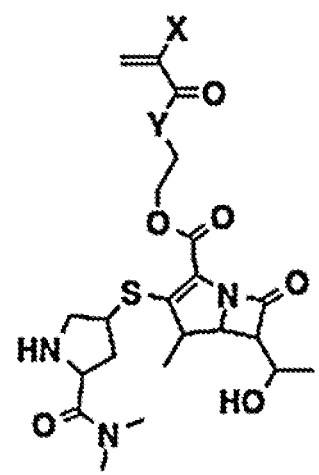
*FIG. 17A*  *FIG. 17B*
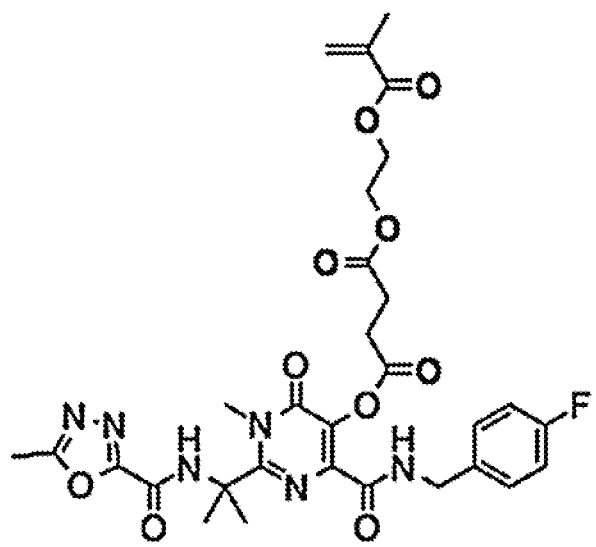
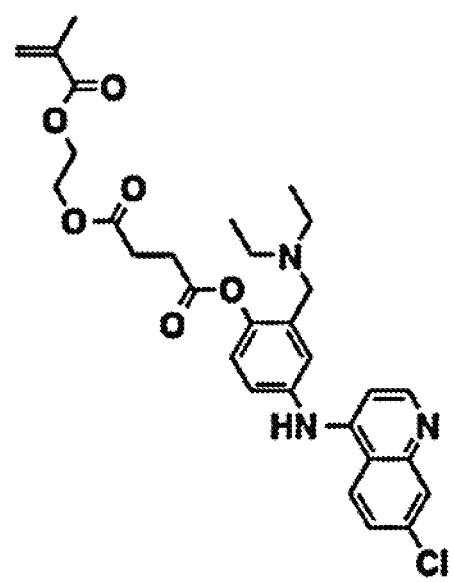
*FIG. 17C*  *FIG. 17D*

STABILIZED POLYMERIC CARRIERS FOR THERAPEUTIC AGENT DELIVERY

CROSS-REFERENCES TO RELATED APPLICATIONS

This application is the national stage of International Application No. PCT/US2015/060450, filed Nov. 12, 2015, which claims priority to U.S. Application No. 62/252,079, filed Nov. 6, 2015, U.S. Application No. 62/107,643, filed Jan. 26, 2015, U.S. Application No. 62/078,901, filed Nov. 12, 2014, and PCT/US2014/065292, filed Nov. 12, 2014, each expressly incorporated herein by reference in its entirety.

STATEMENT OF GOVERNMENT LICENSE RIGHTS

This invention was made with Government support under RO1EB002991 and 1R21EB014572-01A1 awarded by the National Institutes of Health, and under HDTRA1-13-1-0047, awarded by the Defense Threat Reduction Agency. The Government has certain rights in the invention.

BACKGROUND OF THE INVENTION

Advancements in the delivery of therapeutic agents is an ongoing endeavor. Polymeric carriers have been developed for the delivery of therapeutic agents with the goal of effective administration to treat diseases and conditions treatable by the therapeutic agents.

Many conventional polymeric carriers suffer from disadvantages associated with solubility and stability in the circulatory system as well as relative low therapeutic agent capacity. Further disadvantages of conventional polymeric carriers include uncontrollable release, including premature release, of their therapeutic agent cargo.

A need exists for improved polymeric carriers of therapeutic agents that are stable and soluble under physiological conditions such as the circulatory system, that offer high therapeutic agent densities, and that provide controllable release of their therapeutic agent cargo. The present invention seeks to fulfill these needs and provides further related advantages.

SUMMARY OF THE INVENTION

The present invention provides polymeric carriers that are useful for the delivery of therapeutic agents.

In one aspect, the polymeric copolymers of the invention are copolymers and related diblock copolymers having poly(ethylene) (PEG) and zwitterionic stabilizing groups.

In one embodiment, the invention provides a copolymer comprising:

(a) a first constitutional unit having a pendant group comprising a therapeutic agent covalently coupled to the copolymer by a cleavable linkage; and (b) a second constitutional unit having a copolymer-stabilizing pendant group selected from the group consisting of a poly(ethylene oxide) group and a zwitterionic group.

In another embodiment, the invention provides a diblock copolymer comprising:

(a) a first block comprising (i) a first constitutional unit having a pendant group comprising a therapeutic agent covalently coupled to the copolymer by a cleavable linkage;

(ii) a second constitutional unit having a copolymer-stabilizing pendant group selected from the group consisting of a poly(ethylene oxide) group and a zwitterionic group; and (b) a second block comprising a core-forming constitutional unit.

In another aspect, the polymeric copolymers of the invention are copolymers and related diblock copolymers having ampholyte stabilizing groups.

In one embodiment, the invention provides a copolymer comprising:

(a) a first constitutional unit having a pendant group comprising a therapeutic agent covalently coupled to the copolymer by a cleavable linkage;

(b) a second constitutional unit having a pendant anionic group; and (c) a third constitutional group having a pendant cationic group.

In another embodiment, the invention provides a diblock copolymer comprising:

(a) a first block comprising (i) a first constitutional unit having a pendant group comprising a therapeutic agent covalently coupled to the copolymer by a cleavable linkage;

(ii) a second constitutional unit having a pendant anionic group; and (iii) a third constitutional group having a pendant cationic group; and (b) a second block comprising a core-forming constitutional unit.

In one embodiment, the invention provides a copolymer having formula (I):

$$\left(\begin{array}{c}R_1\\ \\ \end{array}\right)_a \left(\begin{array}{c}R_2\\ \\ \end{array}\right)_b \quad (I)$$

with pendant groups: X, O, $L_1$, $C_1$, $[L_2\text{—}C_2]_n$, D; and S wherein $R_1$ and $R_2$ are independently selected from hydrogen and methyl, S is a stabilizing group, X is O or NH, D is a therapeutic agent, $C_1$ is a cleavable linkage, $L_1$ is a linker that covalently couples $C_1$ to X, $C_2$ at each occurrence is an independent cleavable linkage, $L_2$ is a linker that covalently couples $C_1$ to $C_2$, n is 0 or 1, a is an integer from about 5 to about 500, b is an integer from about 5 to about 500, and each * represents the copolymer terminus.

In another embodiment, the invention provides a diblock copolymer having formula (II):

(II)

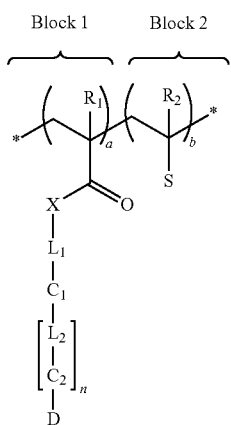

wherein
$R_1$ and $R_2$ are independently selected from hydrogen and methyl,
S is a stabilizing group,
X is O or NH,
D is a therapeutic agent,
$C_1$ is a cleavable linkage,
$L_1$ is a linker that covalently couples $C_1$ to X,
$C_2$ at each occurrence is an independent cleavable linkage,
$L_2$ is a linker that covalently couples $C_1$ to $C_2$,
n is 0 or 1,
a is an integer from about 5 to about 500,
b is an integer from about 5 to about 500, and
each * represents the copolymer terminus.

In a further embodiment, the invention provides a copolymer having formula (III):

(III)

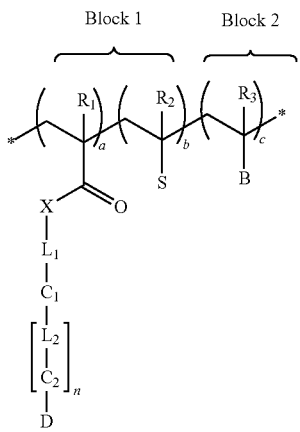

wherein
$R_1$, $R_2$, and $R_3$ are independently selected from hydrogen and methyl,
S is a copolymer-stabilizing group,
B is a core-forming group,
X is O or NH,
D is a therapeutic agent,
$C_1$ is a cleavable linkage,
$L_1$ is a linker that covalently couples $C_1$ to X,
$C_2$ at each occurrence is an independent cleavable linkage,
$L_2$ is a linker that covalently couples $C_1$ to $C_2$,
n is 0 or 1,
a is an integer from about 5 to about 500,
b is an integer from about 5 to about 500,
c is an integer from about 5 to about 500, and
each * represents the copolymer terminus.

In one embodiment, the invention provides a copolymer having formula (IV):

(IV)

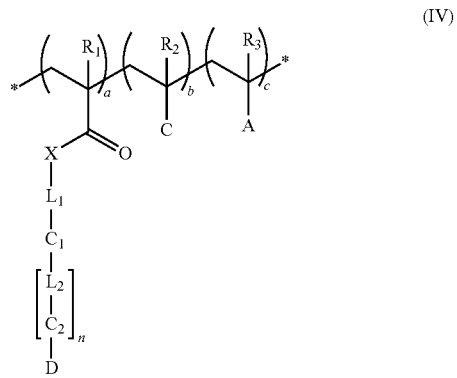

wherein
$R_1$, $R_2$, and $R_3$ are independently selected from hydrogen and methyl,
C is a cationic group,
A is an anionic group,
X is O or NH,
D is a therapeutic agent,
$C_1$ is a cleavable linkage,
$L_1$ is a linker that covalently couples $C_1$ to X,
$C_2$ at each occurrence is an independent cleavable linkage,
$L_2$ is a linker that covalently couples $C_1$ to $C_2$,
n is 0 or 1,
a is an integer from about 5 to about 5,000,
b is an integer from about 5 to about 5,000,
c is an integer from about 5 to about 5,000,
b and c are substantially the same, and
each * represents the copolymer terminus.

In another embodiment, the invention provides a copolymer having formula (V):

(V)

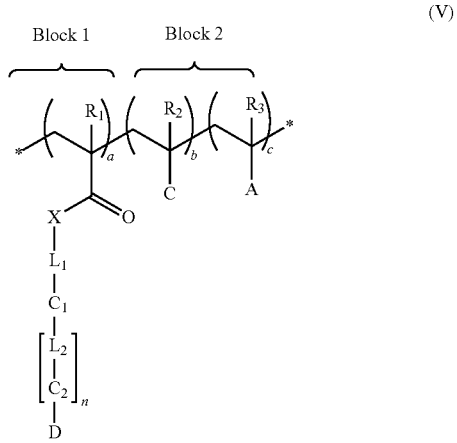

wherein $R_1$, $R_2$, and $R_3$ are independently selected from hydrogen and methyl, C is a cationic group, A is an anionic group, X is O or NH, D is a therapeutic agent, $C_1$ is a cleavable linkage, $L_1$ is a linker that covalently couples $C_1$ to X, $C_2$ at each occurrence is an independent cleavable linkage, $L_2$ is a linker that covalently couples $C_1$ to $C_2$, n is 0 or 1, a is an integer from about 5 to about 5,000, b is an integer from about 5 to about 5,000, c is an integer from about 5 to about 5,000, b and c are substantially the same, and each * represents the copolymer terminus.

In a further embodiment, the invention provides a diblock copolymer having formula (VI):

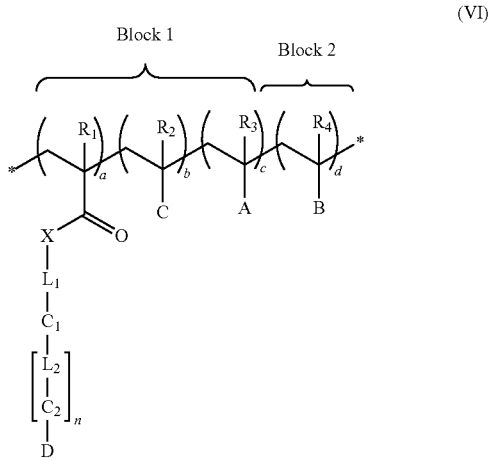

(VI)

wherein $R_1$, $R_2$, $R_3$, and $R_4$ are independently selected from hydrogen and methyl, C is a cationic group, A is an anionic group, B is a core-forming group X is O or NH, D is a therapeutic agent, $C_1$ is a cleavable linkage, $L_1$ is a linker that covalently couples $C_1$ to X, $C_2$ at each occurrence is an independent cleavable linkage, $L_2$ is a linker that covalently couples $C_1$ to $C_2$, n is 0 or 1, a is an integer from about 5 to about 5,000, b is an integer from about 5 to about 5,000, c is an integer from about 5 to about 5,000, d is an integer from about 5 to about 5,000, b and c are substantially the same, and each * represents the copolymer terminus.

In another aspect, the invention provides particles assemblies comprising the copolymers and diblock copolymers of the invention.

In further aspect of the invention, methods for making and using copolymers and diblock copolymers are provided.

DESCRIPTION OF THE DRAWINGS

The foregoing aspects and many of the attendant advantages of this invention will become more readily appreciated as the same become better understood by reference to the following detailed description, when taken in conjunction with the accompanying drawings.

FIGS. 17A-17G show representative polymerizable prodrug monomers useful for making the copolymers of the invention: ceftazidime (17A) (X is hydrogen or C1-C6 alkyl), meropenem (17B) (X is hydrogen or C1-C6 alkyl), raltegravir (17C), amodiaquin (17D), artesunaten (17E), quinine (17F), and lamivudine (17G).

DETAILED DESCRIPTION OF THE INVENTION

Figure 1A:
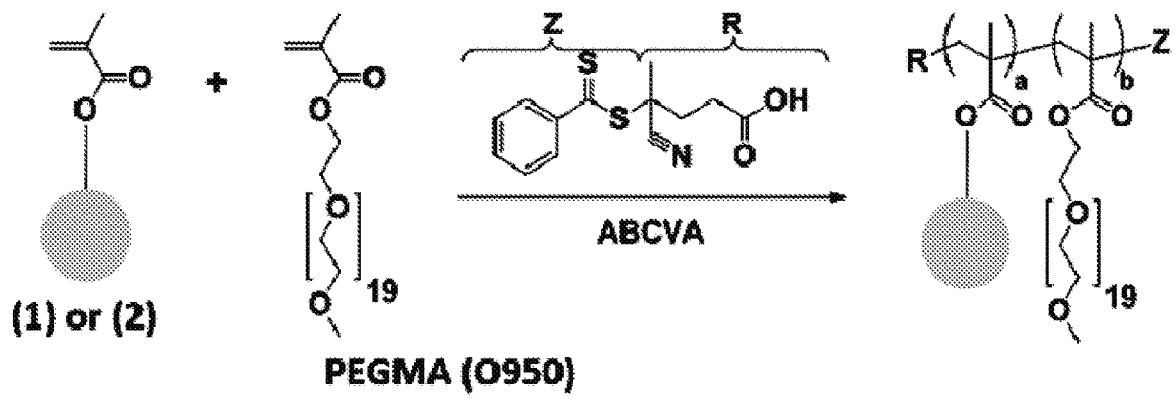
FIG. 1A is a schematic illustration of the preparation of representative ciprofloxacin prodrug copolymers of the invention, poly(O950-co-HBC) and poly(O950-co-CPM), by RAFT polymerization.
Figure 1A:
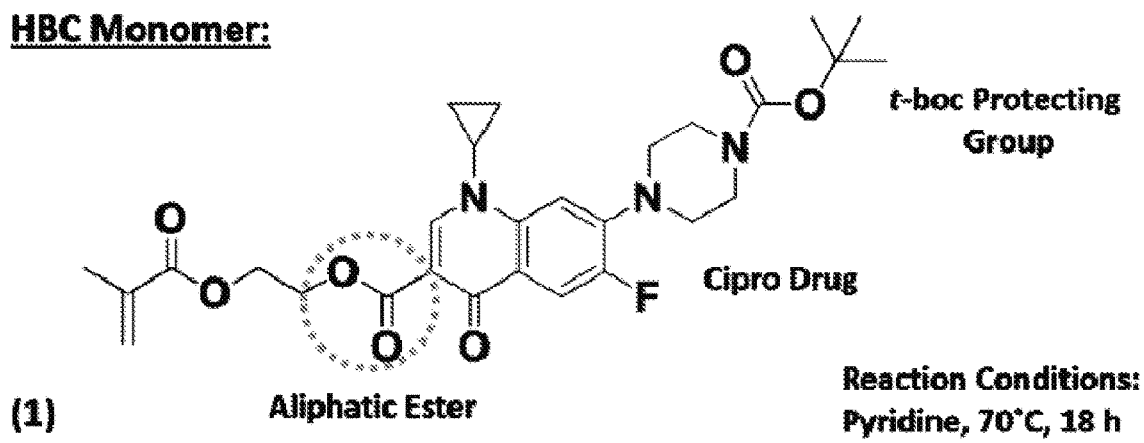
Figure 1A:
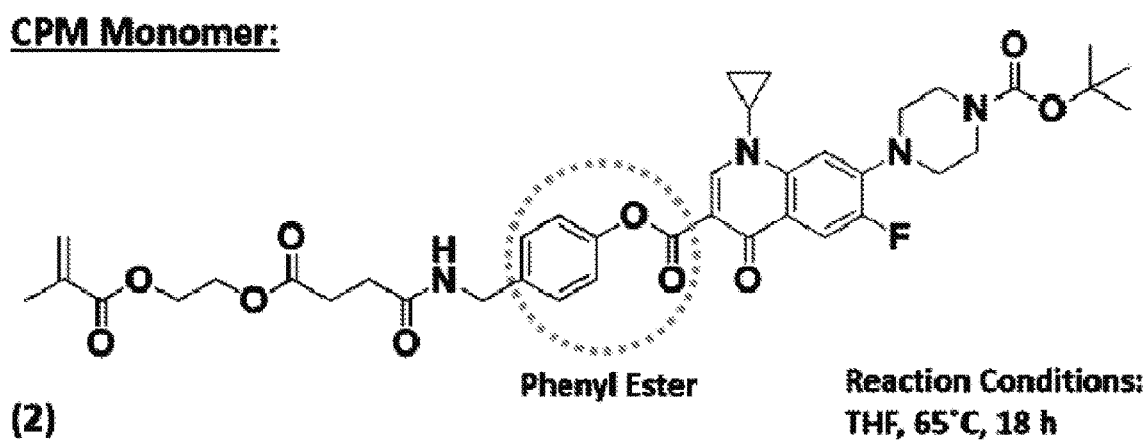

The present invention provides polymeric carriers that are useful for the delivery of therapeutic agents to treat diseases and conditions treatable by the administration of the therapeutic agents. The polymeric carriers of the invention are macromolecular prodrugs that effectively delivery their therapeutic agent cargo by timely release of the therapeutic agent.

The polymeric carriers of the invention advantageously have high therapeutic agent content and therefore are powerful as therapeutic agent-dense delivery systems. The polymeric carriers of the invention are also advantageously bioavailable, stable to physiological conditions encountered in the circulatory system, and deliver their cargo at effective release rates. The combination of high therapeutic agent density, effective therapeutic agent release rate, and bioavailability and stability in the circulatory system render the polymeric carriers of the invention unique and improved compared to conventional polymeric drug carriers known in the art.

The high therapeutic agent density of the polymeric carriers results from the methods used in preparing the carriers. The polymeric carriers are prepared by polymerization processes that include copolymerization of a polymerizable prodrug monomer with one or more other monomers. This is in direct contrast to conventional processes involving conjugation of a version of the therapeutic agent post-polymer formation. By virtue of introducing the therapeutic agent into the polymeric carrier by polymerization of a polymerizable prodrug monomer, the polymeric carriers of the invention offer significantly greater therapeutic agent density compared to conventional polymeric drug carriers.

The stability and effective therapeutic agent release afforded by the polymeric carriers of the invention are due to structural features of these unique carriers. In addition to constitutional units that include releasable therapeutic agents, the polymeric carriers of the invention also include constitutional units that include stabilizing groups. The stabilizing groups are hydrophilic groups that are readily hydrated under physiological conditions. The stabilizing groups include uncharged hydrophilic groups and substantially electronically neutral groups. As discussed in detail below, uncharged hydrophilic groups include polyether groups, such as poly(alkylene oxide)s and polyhydroxyl groups, such as saccharides (mono- and polysaccharides); and substantially electronically neutral groups include zwitterionic groups (carboxy-, sulfo- and phosphobetaines) and ampholyte groups (constitutional units that include positively charged groups or groups that become positively charged under physiological conditions, and constitutional units that include negatively charged groups or groups that become negatively charged under physiological conditions). Like the incorporation of the therapeutic agents, the stabilizing groups are introduced to the polymeric carriers of the invention by polymerization processes that involve copolymerization of a suitable stabilizing group monomer with a polymerizable prodrug monomer.

Copolymers and Diblock Copolymers

In one aspect, the polymeric copolymers of the invention are copolymers and related diblock copolymers having poly(ethylene) (PEG) and zwitterionic stabilizing groups.

In one embodiment, the invention provides a copolymer comprising:

(a) a first constitutional unit having a pendant group comprising a therapeutic agent covalently coupled to the copolymer by a cleavable linkage; and (b) a second constitutional unit having a copolymer-stabilizing pendant group selected from the group consisting of a poly(ethylene oxide) group and a zwitterionic group.

In another embodiment, the invention provides a diblock copolymer comprising:

(a) a first block comprising (i) a first constitutional unit having a pendant group comprising a therapeutic agent covalently coupled to the copolymer by a cleavable linkage; and (ii) a second constitutional unit having a copolymer-stabilizing pendant group selected from the group consisting of a poly(ethylene oxide) group and a zwitterionic group; and (b) a second block comprising a core-forming constitutional unit.

In another aspect, the polymeric copolymers of the invention are copolymers and related diblock copolymers having ampholyte stabilizing groups.

In one embodiment, the invention provides a copolymer comprising:

(a) a first constitutional unit having a pendant group comprising a therapeutic agent covalently coupled to the copolymer by a cleavable linkage;

(b) a second constitutional unit having a pendant anionic group; and (c) a third constitutional group having a pendant cationic group.

In another embodiment, the invention provides a diblock copolymer comprising:

(a) a first block comprising (i) a first constitutional unit having a pendant group comprising a therapeutic agent covalently coupled to the copolymer by a cleavable linkage;

(ii) a second constitutional unit having a pendant anionic group; and (iii) a third constitutional group having a pendant cationic group; and (b) a second block comprising a core-forming constitutional unit.

In the polymeric carriers of the invention, the cleavable linkage is cleavable by hydrolysis. Representative cleavable linkages include esters, acetals, hemiacetals, hemiacetal esters, and hydrazine. In certain embodiments, the cleavable linkage is an aliphatic ester (e.g., —$CH_2$—C(=O)—O—). In other embodiments, the cleavable linkage is a phenyl ester (e.g., —$C_6H_4$—C(=O)—O—).

In certain embodiments, the cleavable linkage is cleavable by enzymatic action. Representative cleavable linkages include amino acid sequences cleavable by enzymatic action.

The polymeric carriers of the invention release therapeutic agents. In certain embodiments, the therapeutic agent is a small molecule therapeutic agent (i.e., having a molecular weight less than about 800 g/mole). In other embodiments, the therapeutic agent is a peptide therapeutic agent. Representative therapeutic agents releasable by the polymeric carriers of the invention as described below.

The polymeric carriers of the invention have a high therapeutic agent density. For the poly(ethylene oxide) and zwitterionic containing copolymers and diblocks described above, the ratio of the number of first constitutional units to the number of second constitutional units is from about 2:1 to about 1:2. For the polyampholyte containing copolymers and diblocks described above, the ratio of the number of first constitutional units to the number of second and third constitutional units is from about 2:1 to about 1:2.

For the polymeric carriers that include poly(ethylene oxide) groups, the poly(ethylene oxide) group has at least five ethylene oxide repeating units (i.e., —($CH_2CH_2O)_n$—, where n≥5). In certain embodiments, the poly(ethylene oxide) group has from five (5) to thirty (30) ethylene oxide repeating units (i.e., —($CH_2CH_2O)_n$—, where n=5-30).

For the polymeric carriers that include zwitterionic groups, representative zwitterionic groups include carboxybetaine groups, sulfobetaine groups, and phosphobetaine groups.

For the polymeric carriers that include ampholyte groups, the carriers include anionic groups (negatively charged groups) that include an oxyanion or an oxygen-containing acid group that becomes deprotonated under physiological conditions, and include cationic groups (positively charge groups) that include a nitrogen-containing group that becomes protonated under physiological conditions or a nitrogen-containing group having a permanent positive charge. For the polymeric carriers that include ampholyte groups, number of second and third constitutional groups is substantially the same.

Certain of the polymeric carriers of the invention are diblock copolymers that include a core-forming block. The core-forming block provides block copolymers that self assemble under physiological conditions to provide copolymer particles. In certain embodiments described above, the core-forming constitutional unit comprises a therapeutic agent covalently coupled to the copolymer by a cleavable linkage. In other embodiments, the core-forming constitutional unit comprises an endosomalytic group. In further embodiments, the core-forming constitutional unit comprises a hydrophobic group.

For the copolymers described above, in certain embodiments the copolymer is a random copolymer and, in other embodiments the copolymer is a diblock copolymer. In certain embodiments, when the copolymer is a poly(ethylene oxide) or zwitterionic containing diblock copolymer, the diblock copolymer has a first block comprising the first constitutional unit comprising the therapeutic agent and a second block comprising the second constitutional unit comprising the copolymer-stabilizing pendant group. In other embodiments, when the copolymer is an ampholyte containing diblock copolymer, the diblock copolymer has a first block comprising the first constitutional unit comprising the therapeutic agent, and having a second block comprising the second and third constitutional units comprising the anionic and cationic groups, respectively.

The polymeric carriers of the invention described above include the following copolymers and diblock copolymers.

In one aspect of the invention, copolymers and diblock copolymers are provided that include a stabilizing group.

In one embodiment, the invention provides a copolymer having formula (I):

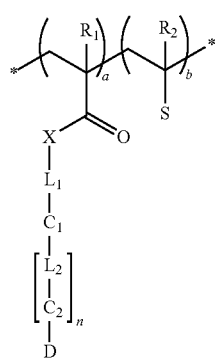

(I)

wherein $R_1$ and $R_2$ are independently selected from hydrogen and methyl,

S is a stabilizing group,

X is O or NH,

D is a therapeutic agent, $C_1$ is a cleavable linkage, $L_1$ is a linker that covalently couples $C_1$ to X, $C_2$ at each occurrence is an independent cleavable linkage, $L_2$ is a linker that covalently couples $C_1$ to $C_2$, n is 0 or 1, a is an integer from about 5 to about 500, b is an integer from about 5 to about 500, and each * represents the copolymer terminus.

In another embodiment, the invention provides a diblock copolymer having formula (II):

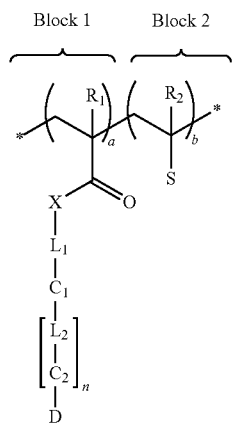

(II)

wherein $R_1$ and $R_2$ are independently selected from hydrogen and methyl,

S is a stabilizing group,

X is O or NH,

D is a therapeutic agent, $C_1$ is a cleavable linkage, $L_1$ is a linker that covalently couples $C_1$ to X, $C_2$ at each occurrence is an independent cleavable linkage, $L_2$ is a linker that covalently couples $C_1$ to $C_2$, n is 0 or 1, a is an integer from about 5 to about 500, b is an integer from about 5 to about 500, and each * represents the copolymer terminus.

In a further embodiment, the invention provides a copolymer having formula (III):

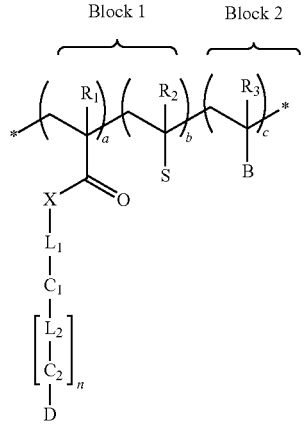

(III)

wherein $R_1$, $R_2$, and $R_3$ are independently selected from hydrogen and methyl, S is a copolymer-stabilizing group, B is a core-forming group, X is O or NH, D is a therapeutic agent, $C_1$ is a cleavable linkage, $L_1$ is a linker that covalently couples $C_1$ to X, $C_2$ at each occurrence is an independent cleavable linkage, $L_2$ is a linker that covalently couples $C_1$ to $C_2$,
n is 0 or 1,
a is an integer from about 5 to about 500,
b is an integer from about 5 to about 500,
c is an integer from about 5 to about 500, and
each * represents the copolymer terminus.

In one embodiment, the invention provides a copolymer having formula (IV):

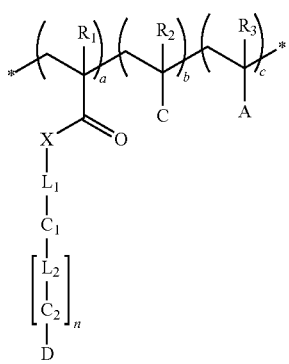

(IV)

wherein
$R_1$, $R_2$, and $R_3$ are independently selected from hydrogen and methyl,
C is a cationic group,
A is an anionic group,
X is O or NH,
D is a therapeutic agent,
$C_1$ is a cleavable linkage,
$L_1$ is a linker that covalently couples $C_1$ to X,
$C_2$ at each occurrence is an independent cleavable linkage,
$L_2$ is a linker that covalently couples $C_1$ to $C_2$,
n is 0 or 1,
a is an integer from about 5 to about 5,000,
b is an integer from about 5 to about 5,000,
c is an integer from about 5 to about 5,000,
b and c are substantially the same, and
each * represents the copolymer terminus.

In another embodiment, the invention provides a copolymer having formula (V):

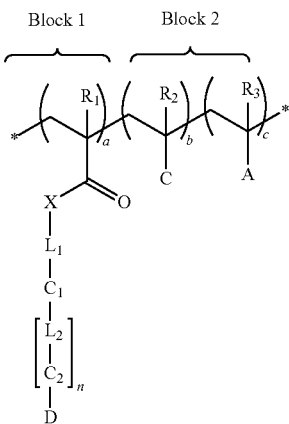

(V)

wherein
$R_1$, $R_2$, and $R_3$ are independently selected from hydrogen and methyl,
C is a cationic group,
A is an anionic group,
X is O or NH,
D is a therapeutic agent,
$C_1$ is a cleavable linkage,
$L_1$ is a linker that covalently couples $C_1$ to X,
$C_2$ at each occurrence is an independent cleavable linkage,
$L_2$ is a linker that covalently couples $C_1$ to $C_2$,
n is 0 or 1,
a is an integer from about 5 to about 5,000,
b is an integer from about 5 to about 5,000,
c is an integer from about 5 to about 5,000,
b and c are substantially the same, and
each * represents the copolymer terminus.

In a further embodiment, the invention provides a diblock copolymer having formula (VI):

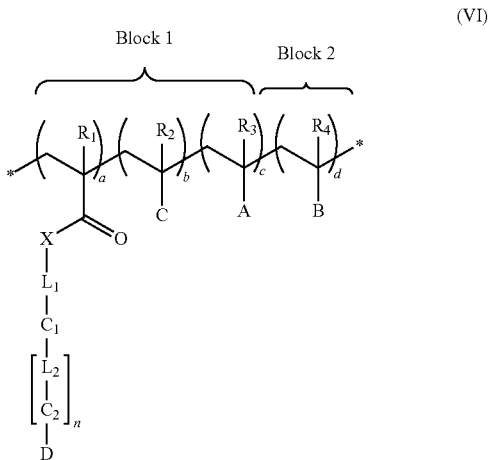

(VI)

wherein
$R_1$, $R_2$, $R_3$, and $R_4$ are independently selected from hydrogen and methyl,
C is a cationic group,
A is an anionic group,
B is a core-forming group
X is O or NH,
D is a therapeutic agent,
$C_1$ is a cleavable linkage,
$L_1$ is a linker that covalently couples $C_1$ to X,
$C_2$ at each occurrence is an independent cleavable linkage,
$L_2$ is a linker that covalently couples $C_1$ to $C_2$,
n is 0 or 1,
a is an integer from about 5 to about 5,000,
b is an integer from about 5 to about 5,000,
c is an integer from about 5 to about 5,000,
d is an integer from about 5 to about 5,000,
b and c are substantially the same, and
each * represents the copolymer terminus.

Representative embodiments of polymeric carriers of formulae (I)-(V) are described below.

In certain embodiments for polymeric carriers of formulae (IV)-(VI), a is an integer from about 5 to about 500, b is an integer from about 5 to about 500, c is an integer from about 5 to about 500, and d when present is an integer from about 5 to about 500.

In certain embodiments, X is O.

In certain embodiments, $L_1$ is a linker group comprising a carbon chain having from two to ten carbon atoms and optionally from two to four oxygen or nitrogen atoms. In certain embodiments, $L_1$ is —$(CH_2)_n$—, where n is 2-10. In other embodiments, $L_1$ is —$(CH_2CH_2O)_n$—, where n is 2-4.

In certain embodiments, $L_2$ is a linker group comprising a carbon chain having from two to ten carbon atoms and optionally from two to four oxygen or nitrogen atoms. In other embodiments, $L_2$ is —$(CH_2)_n$— where n is 2-10. In further embodiments, $L_2$ is —$(CH_2CH_2O)_n$— where n is 2-4.

$C_1$ and $C_2$ are cleavable by hydrolysis or enzymatic action. In certain embodiments, $C_1$ and $C_2$ are independently selected from esters, acetals, hemiacetals, hemiacetal esters, and hydrazines. In certain embodiments, $C_1$ and $C_2$ are independently selected from aliphatic esters (e.g., —$CH_2$—C(=O)—O—) and phenyl esters (e.g., —$C_6H_4$—C(=O)—O—). For phenyl ester linkages, it will be appreciated that the phenyl group can be substituted with one, two, three, or four groups to adjust the rate of phenyl ester cleavage. In general, the electron withdrawing groups increase the rate of cleavage and electron donating groups decrease the rate of cleavage. Representative phenyl group substituents include C1-C6 alkyl groups (e.g., methyl, ethyl), C1-C6 alkoxy groups (e.g., methoxy, ethoxy), halo groups (e.g., fluoro, chloro, bromo), carbonyl containing groups (e.g., —C(=O)—$CH_3$, —C(=O)—$OCH_3$, —C(=O)—$NH_2$). In certain embodiments, the cleavable linkage is an amino acid sequence cleavable by enzymatic action.

As noted above, the polymeric carriers of the invention release therapeutic agents. In certain embodiments, the therapeutic agent is a small molecule therapeutic agent (i.e., having a molecular weight less than about 800 g/mole). In other embodiments, the therapeutic agent is a peptide therapeutic agent. Representative therapeutic agents releasable by the polymeric carriers of the invention as described below.

The polymeric carriers of the invention release therapeutic agents. In certain embodiments, the therapeutic agent is a small molecule therapeutic agent (i.e., having a molecular weight less than about 800 g/mole). In other embodiments, the therapeutic agent is a peptide therapeutic agent. Representative therapeutic agents releasable by the polymeric carriers of the invention as described below.

The polymeric carriers of the invention have a high therapeutic agent density. For the polymeric carriers of formulae (I)-(III), in certain embodiments, a:b is from about 2:1 to about 1:2. In certain embodiments, a:b is from about 2:1 to about 1:1. In other embodiments, a:b is about 1:1.

For certain embodiments of the polymeric carriers of formulae (I)-(III) where S is a poly(ethylene oxide), the drug monomer and hydrophilic monomer is less than about 200 units total (a+b≤200) and in other embodiments about 15-30 units total (a+b=15-30). For certain embodiments of the polymeric carriers of formulae (I)-(III) where S is a zwitterionic group, the drug monomer and hydrophilic monomer is less than about 400 units total (a+b≤400) and in other embodiments about 25-50 units total (a+b=25-50). Optimum control over the polymerization is observed in these ranges.

For these embodiments, the specific ratio of the monomers will be dependent on the overall polymer architecture. If the drug-containing segment (i.e., drug-containing block) is desired to be molecularly soluble in aqueous solutions, then lower amounts of the drug monomer can be used (e.g., a≤b). For certain of these embodiments, this is about 20-40 wt % drug monomer based on the total weight of the polymer (e.g., 10-30 mol % relative to the total monomer feed). In certain embodiments, this is about 20-30 wt % drug monomer based on the total weight of the polymer (e.g., 15-25 mol % relative to the total monomer feed).

Alternatively, as described herein, the drug-containing segment may be incorporated into a block copolymer with an additional stabilizing polymer segment for stabilization in aqueous solution. In this embodiment, the drug-containing segment can include higher relative amounts of the drug (e.g., from about 50 to approaching 100 mole or weight %). As described herein, the drug-containing segment can include additional constitutional units to impart desirable properties (e.g., to facilitate polymeric carriers acting as depots). In certain embodiments, the drug-containing segment includes 100 mole or weight % drug-containing constitutional unit.

When it is desirable for the polymeric carrier of the invention to serve as a therapeutic agent depot (e.g., formulae (III) or (VI)), the drug-containing segment can include significantly greater amounts of the drug (e.g., from about 50 to approaching 100 mole or weight %). In certain embodiments, these segments can include from 50-99, 50-95, 50-90, 50-80, 50-70 mole or weight percent such polymeric carriers include drug-containing constitutional unit.

In certain embodiments, for the polymeric carriers of formulae (I)-(III), S comprises a poly(ethylene oxide) group. In certain embodiments, S comprises a poly(ethylene oxide) group having at least five ethylene oxide repeating units (i.e., —$(CH_2CH_2O)_n$—, where n≥5). In certain embodiments, S comprises a poly(ethylene oxide) group having from five (5) to thirty (30) ethylene oxide repeating units (i.e., —$(CH_2CH_2O)_n$—, where n=5-30). In certain embodiments, S is

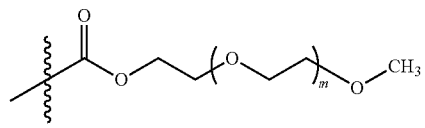

wherein m is an integer from 5 to 30.

In some embodiments, S comprises a poly(ethylene oxide) group having a molecular weight of 1000 Daltons or more (e.g., 2000 Da or more, 3000 Da or more, 4000 or more, 5000 or more, or 7000 or more) and/or 10 kDa or less (e.g., 7000 Da or less, 5000 Da or less, 4000 Da or less, 3000 Da or less, or 2000 Da or less).

In certain embodiments, for the polymeric carriers of formulae (I)-(III), S comprises a zwitterionic group. In certain embodiments, S comprises a zwitterionic group selected from the group consisting of a carboxybetaine group, a sulfobetaine group, and a phosphobetaine group. In certain embodiments, S is selected from

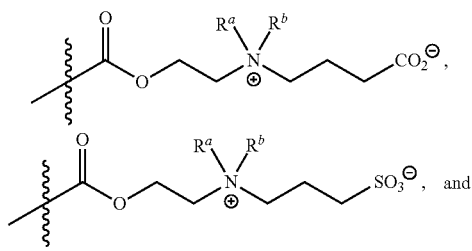

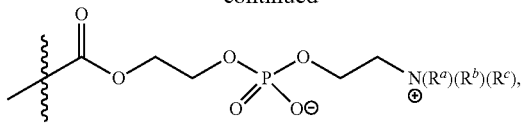

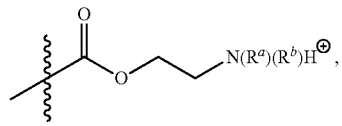

wherein $R^a$, $R^b$, and $R^c$ are independently selected from hydrogen and C1-C6 alkyl.

In certain embodiments, for the polymeric carriers of formulae (IV)-(VI), the ratio a:b+c is from about 2:1 to about 1:2. In certain embodiments, a:b+c is from about 2:1 to about 1:1. In other embodiments, a:b+c is about 1:1.

For certain embodiments of the polymeric carriers of formulae (IV)-(VI) where the stabilizing groups are a combination of anionic and cationic groups as described herein, or neutral (nonionic) monomers, such as hydroxyethyl acrylamide, hydroxylethyl acrylate, and dimethylacrylamide, the drug monomer and hydrophilic monomer can total about 15,000 units (a+b+c=15,000). In other embodiments, from about 10,000-12,000 units (a+b+c=10,000-12,000), and in further embodiments, from about 5,000-10,000 units.

For these embodiments, the specific ratio of the monomers will be dependent on the overall polymer architecture. If the drug-containing segment (i.e., drug-containing block) is desired to be molecularly soluble in aqueous solutions, then lower amounts of the drug monomer can be used (e.g., a≤b). For certain of these embodiments, this is about 20-40 wt % drug monomer based on the total weight of the polymer (e.g., 10-30 mol % relative to the total monomer feed). In certain embodiments, this is about 20-30 wt % drug monomer based on the total weight of the polymer (e.g., 15-25 mol % relative to the total monomer feed). Alternatively, as described herein, the drug-containing segment may be incorporated into a block copolymer with an additional stabilizing polymer segment for stabilization in aqueous solution. In this embodiment, the drug-containing segment can include higher relative amounts of the drug (e.g., from about 50 to approaching 100 mole or weight %). As described herein, the drug-containing segment can include additional constitutional units to impart desirable properties (e.g., to facilitate polymeric carriers acting as depots). In certain embodiments, the drug-containing segment includes 100 mole or weight % drug-containing constitutional unit. When it is desirable for the polymeric carrier of the invention to serve as a therapeutic agent depot (e.g., formulae (III) or (VI)), the drug-containing segment can include significantly greater amounts of the drug (e.g., from about 50 to approaching 100 mole or weight %). In certain embodiments, these segments can include from 50-99, 50-95, 50-90, 50-80, 50-70 mole or weight percent such polymeric carriers include drug-containing constitutional unit.

In certain embodiments, for the polymeric carriers of formulae (IV)-(VI), the anionic group is selected from an oxyanion or an oxygen-containing acid group that becomes deprotonated under physiological conditions. Representative anionic groups include carboxylic acid groups and carboxylate groups.

In certain embodiments, for the polymeric carriers of formulae (IV)-(VI), the cationic group is selected from a nitrogen-containing group that becomes protonated under physiological conditions or a nitrogen-containing group having a permanent positive charge. Representative cationic groups include amino groups, secondary amine groups, tertiary amine groups, and quaternary amine groups. In one embodiment, the cationic group is wherein $R^a$ and $R^b$ are independently selected from hydrogen and C1-C6 alkyl.

In certain embodiments, the polymeric carriers of the invention include core-forming constitutional units, which include core-forming groups (see B in formulae (III) and (VI)). In certain embodiments, the core-forming constitutional unit is a constitutional unit that comprises a therapeutic agent cleavable from the carrier. In other embodiments, the core-forming constitutional unit is an endosomalytic constitutional unit, or a hydrophobic constitutional unit, as described below.

When the polymeric carriers of the invention includes core-forming constitutional units that comprise a therapeutic agent cleavable from the carrier, these polymeric carriers can ideally serve as therapeutic agent depots and have advantageous therapeutic agent release profiles. See, for example, FIG. 9A.

In certain embodiments, the polymeric carriers of the invention that include core-forming constitutional units, self assemble to provide particles in aqueous environments. The particles can be advantageously administered and therefore deliver polymeric carriers having high therapeutic agent content.

In a further aspect, the invention provides particles that self assemble to provide polymer particles. In this aspect, in certain embodiments, the particles comprise the polymeric carriers of formulae (III) or (VI).

In certain embodiments, the polymeric carriers of the invention comprise the polymers of formulae (I)-(VI). In other embodiments, the polymeric carriers of the invention (e.g., copolymers and diblock copolymers of the invention) consist essentially of the copolymers and block copolymers of the invention of formulae (I)-(VI) and do not include other components that materially alter the properties of the polymers (e.g., do not include constitutional units that adversely affect the advantageous therapeutic agent loading, therapeutic agent release, bioavailability and/or stability of the polymeric carrier). In further embodiments, the polymeric carriers of the invention (e.g., copolymers and diblock copolymers of the invention) consist of the copolymers and block copolymers of the invention of formulae (I)-(VI) and do not include any other components.

The polymer carriers of the invention are described as copolymers and diblock copolymers (see, for example, formulae (I)-(VI)). It will be appreciated that the polymers of the invention include higher order polymers (e.g., triblock copolymers) and polymer architectures that include the copolymers and diblock copolymers of the invention (e.g., copolymers and diblock copolymers of formulae (I)-(VI)).

In other aspects, the invention provides methods for making the polymeric carriers of the invention. As noted above and described herein, the polymeric carriers of the invention are prepared by copolymerization of a polymerizable prodrug monomers and monomers that include stabilizing groups containing monomer (e.g., RAFT polymerization). The polymerization process can be one that provides a random copolymer or a diblock copolymer. The copolymer of diblock copolymer can be further subject to chain extension to provide diblock copolymer (from the random copolymer) or a higher order block copolymer (from the diblock copolymer). Chain extension can be carried out to with suitable monomers or comonomers to provide blocks that include the therapeutic agent to be released, endosomolytic blocks, or hydrophobic blocks.

In further aspects of the invention, methods for using the polymeric carriers of the invention are provided. As noted above, the polymeric carriers are useful to delivery therapeutic agents. In one embodiment, the invention provides a method for administering a therapeutic agent to a subject. In the method, a therapeutically effective amount of a polymeric carrier of the invention is administered to a subject in need thereof. In another embodiment, the invention provides a method for treating a disease of condition treatable by a therapeutic agent. In the method, a therapeutically effective amount of a polymeric carrier of the invention is administered to a subject in need thereof, wherein the therapeutic agent released from the carrier is effective to treat the disease or condition.

Endosomolytic Constitutional Units and Blocks

In some embodiments, the core-forming block includes pH-responsive, endosomal releasing blocks. As used herein, the terms "pH-responsive, endosomal releasing polymer" or "pH-responsive, endosomal releasing block" refers to a polymer or polymer block, respectively, that, at about physiologic pH (7.4), undergoes a transition at the lower pH environment of the endosome and becomes endosomal membrane destabilizing thereby releasing cargo (e.g., therapeutic agent) transported by the polymer to the surrounding cytosol. Such pH-responsive, endosomal releasing polymers, polymer blocks, and other stimuli-responsive polymers have been described previously. See, for example, PCT applications PCT/US96/13874, PCT/US99/00122, PCT/US01/00356, PCT/US04/03845, PCT/US2007/064238, PCT/US2009/043847, PCT/US2009/043852, PCT/US2009/043839, PCT/US2009/067193, PCT/US2009/043849, PCT/US2009/043837, PCT/US2009/043859, PCT/US2009/043860, PCT/US2009/043853, and PCT/US2009/063648, each expressly incorporated herein by reference in its entirety.

In certain embodiments, the pH-responsive endosomal, releasing block has constitutional units derived from one or more of an alkyl acrylate (e.g., a C1-C6 alkyl methacrylate such as BMA), an aminoalkyl acrylate (e.g., a di-C1-C6 alkylamino acrylate such as DEAEMA), and an acrylic acid (e.g., propylacrylic acid). Representative C1-C6 alkyl acrylates (e.g., C1-C6 alkyl C1-C6 alkylacrylates) include methyl acrylates such as methyl acrylate, methyl methacrylate, and methyl ethacrylate, and ethyl acrylates such as ethyl acrylate, ethyl methacrylate, and ethyl ethacrylate; and representative C1-C6 alkyl acrylic acids include methacrylic acid, ethacrylic acid, propylacrylic acid, and butylacrylic acid.

In certain preferred embodiments of the present disclosure, the pH-responsive, endosomal releasing block comprises constitutional units derived from dimethylaminoethyl methacrylate (DMAEMA), diethylaminoethyl methacrylate (DEAEMA), butylmethacrylate (BMA), propylacrylic acid (PAA), and lauryl methacrylate.

Hydrophobic Constitutional Units and Blocks

In some embodiments, the core-forming block includes hydrophobic uncharged constitutional units. The hydrophobic uncharged constitutional units can each include a $C_8$-$C_{26}$ fatty acid side chain. For example, the fatty acid side chain can include unsaturated fatty acid side chains, such as myristoleic acid, palmitoleic acid, sapienic acid, oleic acid, elaidic acid, vaccenic acid, linoleic acid, linoelaidic acid, α-linoelaidic acid, α-linolenic acid, arachidonic acid, eicosapentaenoic acid, erucic acid, or docosahexaenoic acid side chains. As another example, the fatty acid side chain can include saturated fatty acid side chains, such as caprylic acid, capric acid, lauric acid, myristic acid, palmitic acid, stearic acid, arachidic acid, behenic acid, lignoceric acid, or cerotic acid. The fatty acid side chain is covalently bound to the constitutional unit via, for example, an ester linkage or an amide linkage.

Therapeutic Agents

The polymeric carrier of the invention is a macromolecular prodrug that releases a therapeutic agent. As described above, the therapeutic agent (e.g., an antibiotic agent, an antimalarial agent, an antiHIV agent, a chemotherapeutic agent, a kinase inhibitor) can be released from the polymeric carrier. In some embodiments, the therapeutic agent is modified in such a way that hydrolysis or enzymatic cleavage provides the parent therapeutic agent. In some embodiments, cleavage from the polymer does not provide the original therapeutic agent, but rather releases a modified therapeutic agent that can undergo further modification in a physiological environment such that the modified therapeutic agent can then release the therapeutic agent in an active form at a different rate than the initial cleavage rate. In some embodiments, even though a native therapeutic agent has been modified to provide a polymerizable prodrug monomer, release of the modified therapeutic agent can still provide a therapeutically active molecule.

In some embodiments, the therapeutic agent is an antibiotic agent or a kinase inhibitor. Examples of antibiotic agents include amikacin, gentamicin, neomycin, netilmicin, tobramycin, paromomycin, streptomycin, spectinomycin, geldanamycin, herbimycin, rifaximin, loracarbef,m ertapenem, doripenem, imipenem, meropenem, cefadroxil, cefazolin, cefalotin, cephalexin, cefaclor, cefamandole, cefoxitin, cefprozil, cefuroxime, cefixime, cefdinir, cefditoren, cefoperazone, cefotaxime, cefpodoxime, ceftazidime, ceftibuten, ceftizoxime, ceftriaxzone, cefepime, ceftaroline fosamil, ceftobiprole, teicoplanin, vancomycin, telavancin, dalbavancin, oritavancin, clindamycin, lincomycin, daptomycin, azithromycin, clarithromycin, dirithromycin, erythromycin, roxithromycin, troleandomycin, telithromycin, spiramycin, aztreonam, furazolidone, nitrofurantoin, linezolid, posizolid, radezolid, torezolid, amoxicillin, ampicillin, azlocillin, carbenicillin, cloxacillin, dicloxacillin, flucloxacillin, mezlocillin methicillin, nafcillin, oxicillin, penicillin, piperacillin, temocillin, ticarcillin, piperacillin, ticarcillin, bacitracin, colistin, polymyxin B, xacin, enoxacin, gatifloxacin, gemifloxacin, levofloxacin, lomefloxacin, moxifloxacin, nalidixic acid, norfloxacin, ofloxacin, trovafloxacin, grepafloxacin, sparfloxacin, temafloxacin, mafenide, sulfacetamide, sulfadiazine, silver sulfadiazine, sulfadimethoxine, sulfamethizole, sulfamethoxazole, sulfanilamide, sulfasalazine, sulfisoxazole, trimethoprim-sulfamethoxazole, sulfonamidochrysoidine, demeclocycline, doxycycline, minocycline, oxytetracycline, tetracycline, clofazimine, dapsone, capreomycin, cycloserine, ethambutol, ethionamide, isoniazid, pyrazinamide, rifampin, rifabutin, rifapentine, streptomycin, arsphenamine, chloramphenicol, fosfomycin, fusidic acid, metronidazole, mupirocin, platensimycin, quinupristin, thiamphenicol, tigecycline, tinidazole, and trimethoprim. In some embodiments, the antibiotic agent is ciprofloxacin, meropenem, doxycycline, and/or ceftazidime.

Examples of kinase inhibitors include, for example, afatinib, axitinib, bevacizumab, bosutinib, cetuximab, crizotinib, dasatinib, erlotinib, fostamatinib, gefitinib, ibrutinib, imatinib, lapatinib, lenvatinib, nilotinib, panitumumab, pazopanib, pegaptanib, ranibizumab, roxolitinib, sorafenib, sunitinib, SU6656, trastuzumab, tofacitinib, and vemurafenib. In some embodiments, the kinase inhibitor is dasatinib. In some embodiments, the therapeutic agent is a chemotherapeutic agent, such as a vinca alkaloid or a taxane. Examples of chemotherapeutic agents include illudin, aminitin, gemcitabine, etoposide, docetaxel, camptothecin, and paclitaxel.

Representative polymerizable prodrug monomers are illustrated in FIGS. 17A-17G.

Polymer Definitions

The following definitions relate polymers in general and are useful in understanding the nonlinear copolymers of the invention.

The term "constitutional unit" of a polymer refers to an atom or group of atoms in a polymer, comprising a part of the chain together with its pendant atoms or groups of atoms, if any. The constitutional unit can refer to a repeat unit. The constitutional unit can also refer to an end group on a polymer chain. For example, the constitutional unit of polyethylene glycol can be —CH$_2$CH$_2$O— corresponding to a repeat unit, or —CH$_2$CH$_2$OH corresponding to an end group.

The term "repeat unit" corresponds to the smallest constitutional unit, the repetition of which constitutes a regular macromolecule (or oligomer molecule or block).

The term "end group" (in certain embodiments, * in formulae (I)-(VI)) refers to a constitutional unit with only one attachment to a polymer chain, located at the end of a polymer. For example, the end group can be derived from a monomer unit at the end of the polymer, once the monomer unit has been polymerized. As another example, the end group can be a part of a chain transfer agent or initiating agent that was used to synthesize the polymer.

The term "monomer" is a polymerizable compound that, on polymerization, contributes one or more constitutional units in the structure of the polymer.

The term "polymer" refers to the product that is the result of polymerization of a single monomer.

The term "copolymer" refers to a polymer that is the result of polymerization of two or more different monomers. The number and the nature of each constitutional unit can be separately controlled in a copolymer. The constitutional units can be disposed in a purely random, an alternating random, a regular alternating, a regular block, or a random block configuration unless expressly stated to be otherwise. A purely random configuration can, for example, be: x-x-y-z-x-y-y-z-y-z-z . . . or y-z-x-y-z-y-z-x-x . . . . An alternating random configuration can be: x-y-x-z-y-x-y-z-y-x-z . . . , and a regular alternating configuration can be: x-y-z-x-y-z-x-y-z . . . .

The term "block copolymer" refers to a polymer formed of two or more covalently joined segments of polymers. A regular block configuration has the following general configuration: . . . x-x-x-y-y-y-z-z-z-x-x-x . . . , A random block configuration has the general configuration: . . . x-x-x-z-z-x-x-y-y-y-z-z-z-x-x-z-z-z- . . . .

The following is a description of representative embodiments of the invention describing prodrug monomers and related copolymers prepared from the monomers.

Prodrug Monomers and Related Copolymers

In representative embodiments, the present invention provides prodrug monomers and related copolymers.

Prodrug Copolymers Having Poly(ethylene glycol) Constitutional Units

In certain embodiments, the copolymers of the invention include poly(ethylene glycol) constitutional units. The preparation and properties of representative ciprofloxacin prodrug monomers and related copolymers having poly(ethylene glycol) constitutional units are described in Examples 1 and 2. The representative ciprofloxacin prodrug monomers and related copolymers have cleavable linkers (aliphatic ester and phenolic ester groups) that efficiently release ciprofloxacin at therapeutically effective rates.

Prodrug monomers derived from the antibiotic ciprofloxacin were synthesized with phenolic or aliphatic esters linking the drug to a polymerizable methacrylate group. RAFT polymerization of these monomers exhibited linear pseudo-first-order kinetics and $M_n$ vs. conversion plots, and low Ð values throughout the polymerization. Prodrug monomers were then copolymerized with polyethylene glycol methacrylate to yield hydrophilic copolymers with narrow Ð values. A poly(O950) macroCTA was also synthesized and chain extended with the antibiotic monomers to form diblock copolymers. The resultant copolymers and diblock copolymers were characterized with $^1$H and $^{19}$F NMR and found to contain 16.5 and 30-35 wt. % ciprofloxacin, respectively.

Figure 1B:
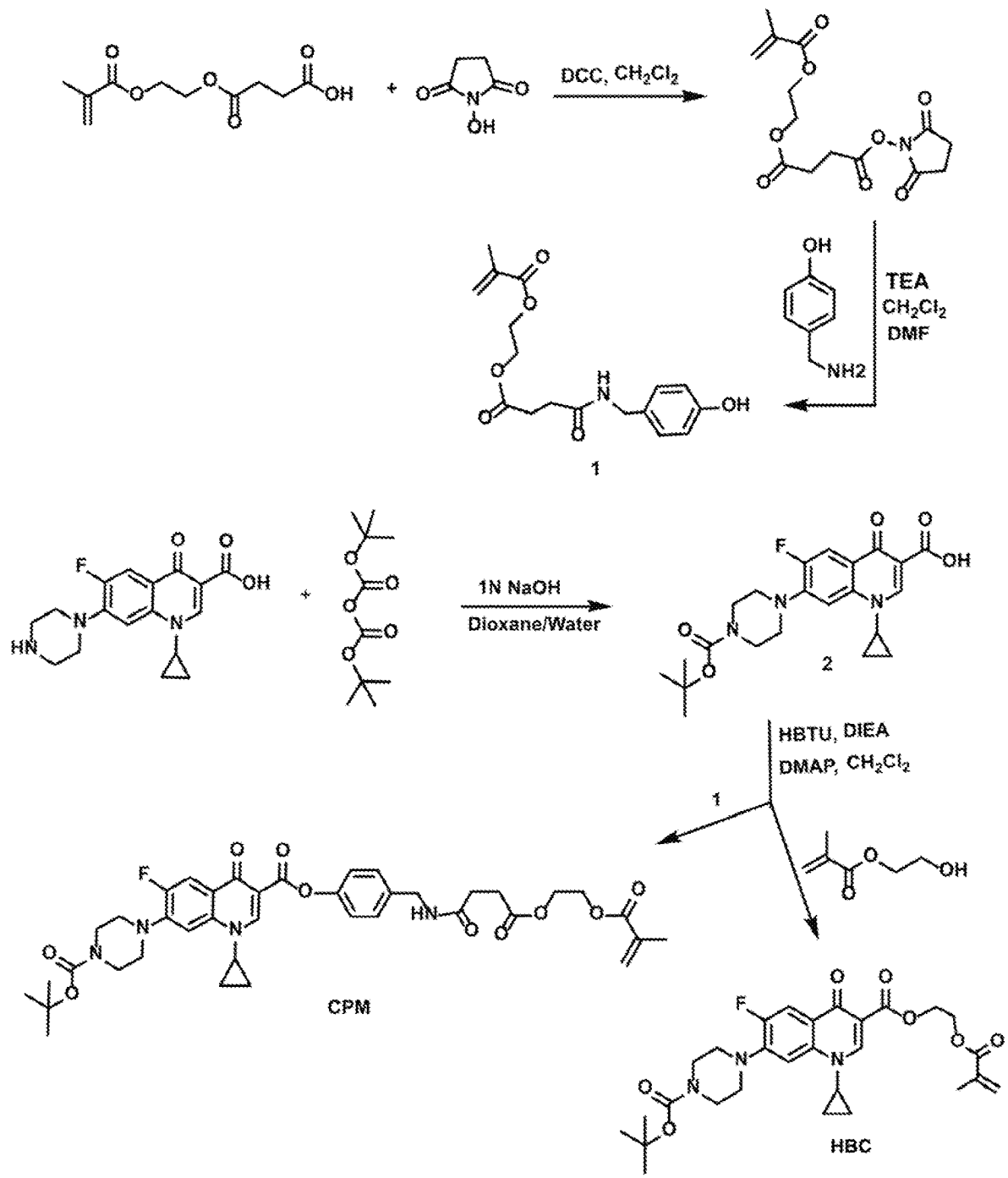
FIG. 1B is a schematic illustration of the preparation of representative polymerizable prodrug ciprofloxacin monomers, HBC (aliphatic ester) and CPM (phenyl ester).

FIG. 1A is a schematic illustration of the preparation of representative ciprofloxacin prodrug copolymers of the invention, poly(O950-co-HBC) and poly(O950-co-CPM), by RAFT polymerization. FIG. 1B is a schematic illustration of the preparation of representative polymerizable prodrug ciprofloxacin monomers, HBC (aliphatic ester) and CPM (phenyl ester).

Figure 2A:
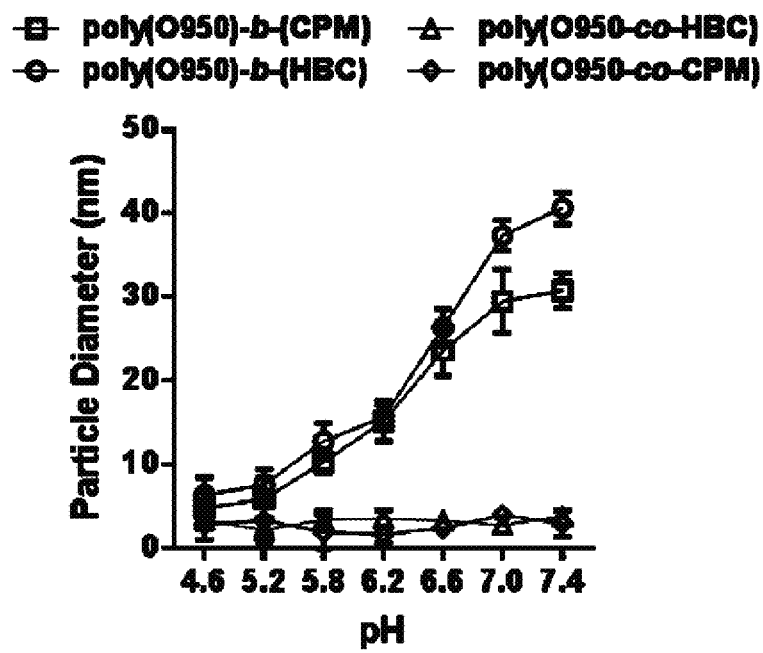
FIGS. 2A and 2B illustrate aqueous size and charge measurements for representative statistical copolymers and diblock copolymers of the invention containing ciprofloxacin (cipro) prodrug residues: hydrodynamic diameter (2A) and zeta potential (2B) as a function of pH. Buffers were prepared using 100 mM sodium phosphate or acetate with 150 mM NaCl for particle size measurements and 10 mM sodium phosphate for zeta potential measurements. All buffers were titrated to the appropriate pH. Polymer concentrations were made at 0.5 mg/mL and 1 mg/mL for dynamic light scattering (DLS) and zeta potential, respectively, and filtered using 0.22 μm filter before running experiments.
Figure 2B:
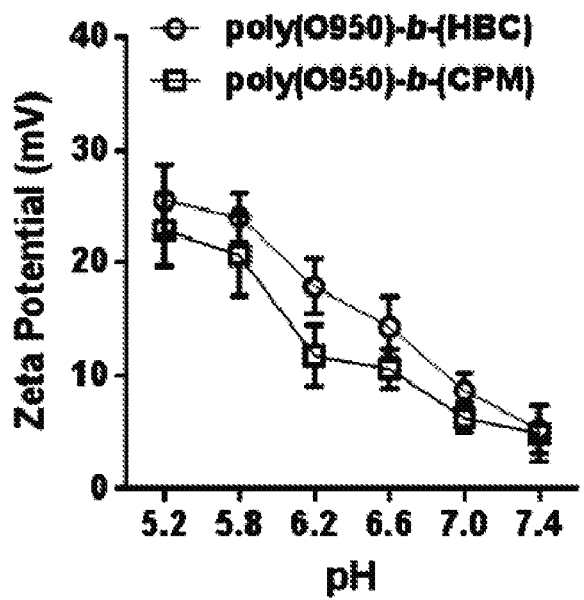

DLS measurements demonstrated that the copolymers remained unimeric between pH 5.6-7.4, while the diblock copolymers formed nanoparticles with diameters between 30-40 nm at physiological pH. FIGS. 2A and 2B illustrate aqueous size and charge measurements for representative statistical copolymers and diblock copolymers of the invention containing ciprofloxacin (cipro) prodrug residues: hydrodynamic diameter (2A) and zeta potential (2B) as a function of pH.

Drug release kinetics were measured in human serum via HPLC analysis. Copolymers containing ciprofloxacin linked via phenolic esters showed faster hydrolysis rates with 50% drug released at 120h, whereas copolymers with the corresponding aliphatic ester linkages showed the same drug release over 22 d. Diblock copolymers with a discrete ciprofloxacin block and a poly(O950) stabilizing block self-assembled into micelles, and exhibited reduced hydrolysis rates for both ester linked drugs.

FIGS. 3A-3E compare drug release kinetics for representative copolymers of the invention measured by high-performance liquid chromatography (HPLC) as a function of time of HBC monomer in the presence of varying amounts of butyrylcholinesterase (BChE) and 100% human serum (3A), CPM monomer in the presence of BChE and serum (3B), poly(O950-co-HBC) in serum, pH 7.4 buffer, and human serum albumin (3C), poly(O950-co-CPM) in serum and in the presence of BChE (3D), and cipro containing statistical copolymers and block copolymers in 100% serum [poly(O950-co-CPM), poly(O950-co-HBC), poly(O950-b-(CPM), and poly(O950-b-(HBC)] (3E).

In vitro toxicity measurements in RAW 264.7 cells showed the copolymers to be nontoxic up to 20 mg/mL following a 24 h incubation period. The polymer drugs were shown to be active against *Burkholderia thailandensis* in a bacteria-macrophage co-culture model of melioidosis with MIC values of 6.0 and 0.6 mM for the aliphatic and phenyl ester linked copolymeric prodrugs, respectively.

Figure 4A:
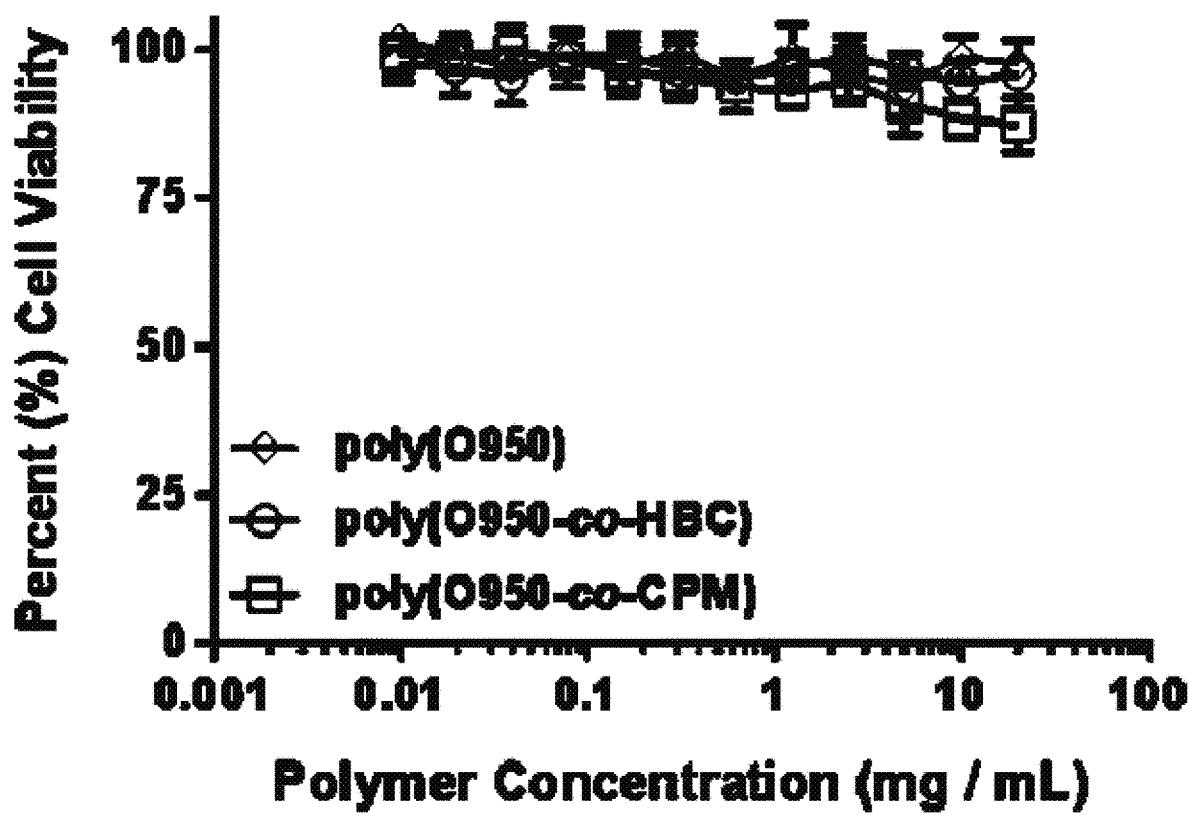
FIGS. 4A and 4B illustrate in vitro toxicity and efficacy using RAW 264.7 cells: MTS results for varying concentrations of poly(O950-co-HBC) and poly(O950-co-CPM) compared to poly(O950) mCTA (negative control) (4A), and co-culture assay with cells treated with varying concentrations of both copolymers and free ciprofloxacin (positive control) following infection with B. thailandensis to determine antibacterial efficacy (4B). Polymer concentrations ranged from 20 mg/mL to 3.7 μg/mL, and toxicity was evaluated with the CellTiter 96AQueous One Solution Cell Proliferation Assay.
Figure 4B:
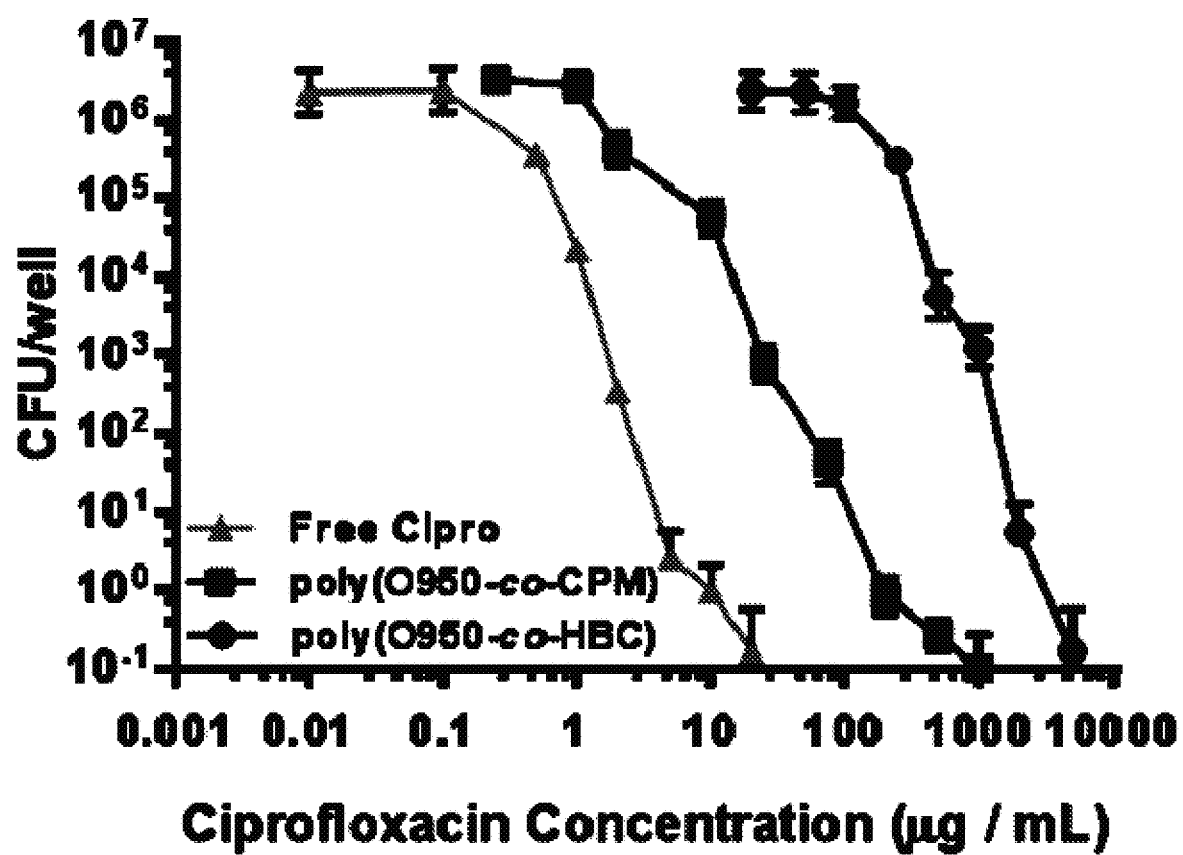

FIGS. 4A and 4B illustrate in vitro toxicity and efficacy using RAW 264.7 cells: MTS results for varying concentrations of poly(O950-co-HBC) and poly(O950-co-CPM) compared to poly(O950) mCTA (negative control) (4A), and co-culture assay with cells treated with varying concentrations of both copolymers and free ciprofloxacin (positive control) following infection with *B. thailandensis* to determine antibacterial efficacy (4B). FIG. 4C compares RAW 264.7 cell viability in the presence of both diblock copolymers was quantified using a MTS assay over a wide polymer dose range (mg/mL). After 24 h, both polymer constructs exhibit a dose dependent toxicity with cell viability measured below 80% with polymer concentrations greater than about 1 mg/mL.

Kinetic Evaluation of (Hydroxyethyl)Methacrylate-Boc-Ciprofloxacin (HBC).

Kinetic studies were conducted with HBC to characterize the polymerization behavior of bulky methacrylate-based prodrug monomers. In these studies, HBC was polymerized at 70° C. in acetic acid using the dithiobenzoate-based RAFT agent, 4-cyano-4-(phenylcarbonothioylthio)pentanoic acid (CTP), and 4,4'-azobis(4-cyanovaleric acid) (ABCVA) as the initiator. Following a short induction period (about 20 min) polymerization proceeds with linear pseudo-first order kinetics suggesting that radical termination reactions remain low throughout the course of the polymerization. Evaluation of the $M_w/M_n$ and $M_n$ vs. conversion plots illustrates the controlled nature of HBC polymerizations under these conditions. $M_n$ versus conversion plot remains linear up to relatively high monomer conversion (about 80%) with low molar mass dispersities and in good agreement with the theoretical molecular weights. For instance, polymerization of HBC for 40 min results in 23% monomer conversion with experimental and theoretical molecular weights of 4.5 and 3.2 kDa, respectively, and a D of 1.12, while at 3 hours 85% conversion is reached with a $M_n$ of 13.3 kDa ($M_{n\ theory}$ of 12.2 kDa) with a Đ of 1.06. Given the close agreement between the theoretical and experimental molecular weights under these conditions, it is likely that degradative chain transfer reactions are not occurring to a significant extent. Analysis of the MWDs shows that the peaks are unimodal and symmetric with a clear shift to lower elution volumes as a function of reaction time. Narrow and symmetric MWDs were also observed for the polymerization of HBC targeting a range of DPs between 12.5 and 100 with a slight increase in the molar mass dispersity (Đ about 1.15 at 64% conversion) for polymerizations targeting a DP of 100. The lack of significant low molecular weight tailing in the MWDs coupled with low Đ values and subsequent blocking experiments provide strong evidence supporting the controlled nature of these polymerizations despite the steric bulkiness of the Cipro monomer.

RAFT Copolymerization of HBC and Ciprofloxacin-(Phenol)Methacrylate (CPM).

Shown in FIG. 1, is the synthetic strategy for the preparation of hydrophilic polyethylene glycol methacrylate (950 Da) (PEGMA O950)-based copolymers with Cipro linked to the polymer backbone via aliphatic (HBC) and phenyl ester (CPM) groups. Based on the favorable kinetic profile for HBC the RAFT copolymerization of this monomer with O950 was conducted in pyridine at the same target $[M]_o/[CTA]_o$ and $[CTA]_o/[I]_o$ ratios (i.e. 25:1 and 5:1). A molar feed ratio of O950 to HBC of 74:26 (mol:mol) was selected to prevent the hydrophobic HBC residues from inducing self-assembly of the copolymers into nanoparticles at physiological pH values. After isolation of the polymer via precipitation in ether, the $M_n$ and Đ were determined by GPC to be 13.1 kDa and 1.08, respectively. Copolymer composition was determined by both $^1H$ NMR and $^{19}F$ NMR with the latter technique yielding a molar composition of 72% O950 and 28% HBC (16 wt. % Cipro).

To produce the therapeutically active form of the polymeric prodrug, the Boc protecting groups were removed using neat TFA at 25° C. for 2 h. Quantitative Boc removal was confirmed by $^1H$ NMR by following the disappearance of the sharp (9H) resonance at δ=1.52 ppm. The synthesis of poly(O950-co-CPM) was conducted under conditions similar to those employed for HBC except that the temperature was reduced to 65° C. to minimize the potential for cleavage of the more labile phenyl ester linkages. Because of the greater solubility of the CPM monomer in organic solvents it was possible to conduct polymerizations in THF. Similar to the polymerization of poly(O950-co-HBC), a feed ratio of 80:20 (mol:mol) O950:CPM was selected to prevent association of the hydrophobic CPM residues and subsequent formation of self-assembled nanoparticles. Copolymer composition (via $^{19}F$ NMR) was determined to be 64 mol % O950 and 36 mol % CPM (80 mol % O950 and 20 mol % CPM feed) with $M_n$ and Đ values, as measured by GPC, of 11.8 kDa and 1.09, respectively.

Synthesis of Poly(O950)-b-(HBC) and Poly(O950)-b-(CPM).

Diblock copolymers were designed with the hydrophobic prodrug monomer residues localized in a discrete block and stabilized in solution by a hydrophilic poly(O950) segment. These diblock copolymers were prepared in order to establish the effect of this morphology on the resultant drug release profiles. This architecture could be advantageous in drug delivery applications because it potentially allows polymers with prodrug contents greater than 50 wt % to be synthesized, and provides a further tuning point for drug release kinetics. The diblock copolymers were synthesized by first preparing a poly(O950) macroCTA ($M_n$=17.5 kDa, Đ=1.12) from which HBC and CPM were polymerized targeting a DP of 25. The formation of the desired poly (O950)-b-(HBC) and poly(O950)-b-(CPM) diblock copolymers was confirmed by the clear shift in the MWDs to shorter elution volumes and lack of significant homopolymer impurity. Based on $^{19}F$ NMR, the block ratios for poly(O950)-b-(HBC) and poly(O950)-b-(CPM) were determined to be 18:56 (34 wt. % Cipro) and 18:32 (30 wt. % drug), respectively.

Aqueous Solution Studies for Cipro Containing Copolymers and Diblock Copolymers.

The aqueous morphologies of both the copolymer and diblock copolymer architectures were evaluated under physiologically relevant conditions. At a pH of 7.4 and 7.0, where the deprotected Cipro residues should be predominately deprotonated and therefore hydrophobic in nature, hydrodynamic diameters of 40.7±2.01 and 37.4±1.85 nm are observed for poly(O950)-b-(HBC), respectively. Similar particle sizes were observed for poly(O950)-b-(CPM) (30.8±2.14 at pH 7.4 and 29.5±3.83 at pH 7.0) at these pH values. The apparent particle sizes are consistent with the formation of spherical core-shell nanoparticles where poly (O950) segments forming a hydrophilic corona around a dehydrated polymeric prodrug core. In addition, the observed differences in size between the two diblocks at higher pH values (FIG. 2A) may be attributed to slightly longer HBC block relative to CPM (i.e. DP of HBC block of 56 vs. 32 for CPM). Reduction of the solution pH to 5.2 results in a significant decrease in hydrodynamic diameter to around 5-8 nm for both diblock copolymers (FIG. 2A). This behavior is likely caused by an increase in the protonation state of the secondary amines present on Cipro residues in the polymer core. The resultant increase in positive charge along the polymer backbone destabilizes the micellar core via charge-charge repulsion while increasing the hydrophilicity of the core-forming segment. These sizes are consistent with molecularly dissolved unimers and do not change significantly upon further reduction of the solution pH (FIG. 2A). Zeta potential measurements for these materials at pH 7.4 were determined to be slightly positive with values of 5.24±2.1 mV and 4.85±2.5 mV observed for poly(O950)-b-(HBC) and poly(O950)-b-(CPM), respectively (FIG. 2B). Decreasing the pH to 5.2 increases the zeta potential to 26.56±3.14 mV for poly(O950)-b-(HBC) and 22.96±3.21 for poly(O950)-b-(CPM) (FIG. 2B) supporting an increase in the protonation state of the polymer at lower pH values.

Release Kinetics of Cipro from Copolymers and Diblock Copolymers Quantified by HPLC.

Figure 3A:
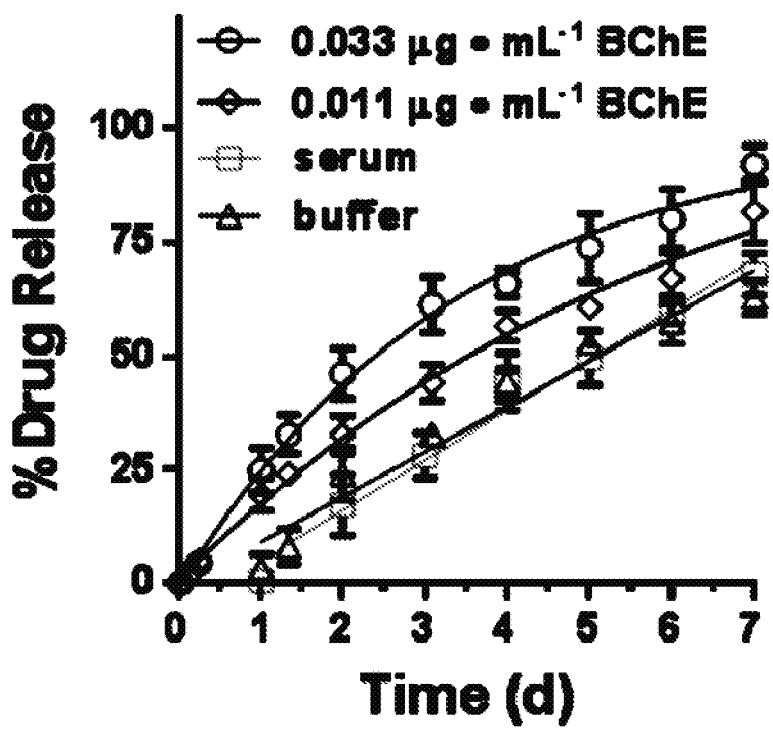
FIGS. 3A-3E compare drug release kinetics for representative copolymers of the invention measured by high-performance liquid chromatography (HPLC) as a function of time of HBC monomer in the presence of varying amounts of butyrylcholinesterase (BChE) and 100% human serum (3A), CPM monomer in the presence of BChE and serum (3B), poly(O950-co-HBC) in serum, pH 7.4 buffer, and human serum albumin (3C), poly(O950-co-CPM) in serum and in the presence of BChE (3D), and cipro containing statistical copolymers and block copolymers in 100% serum [poly(O950-co-CPM), poly(O950-co-HBC), poly(O950-b-(CPM), and poly(O950-b-(HBC)] (3E). The drug release studies were conducted at 37° C. and free drug detection was quantified using an elution gradient profile at 277 nm. The studies were conducted with deprotected monomers and polymers. Free ciprofloxacin was extracted from serum samples using acetonitrile as an organic phase precipitation technique to remove proteins, and HPLC analysis was conducted using a mobile phase consisting of 2% aq. acetic acid:acetonitrile (84:16 v/v/).

HPLC was used to quantify drug release by detecting free drug as a function of time normalized to amount of drug present during initial incubation. This in turn was standardized to the total available drug in the system as quantified by dissolving a known amount of polymer in 10% aq. $H_2SO_4$ for 48 h at 25° C. Using a Cipro standard curve, the total amount of drug in the polymers was validated against compositional values obtained from $^{19}F$ NMR. In these studies, it was observed that free Cipro elutes at approximately 1.59±0.04 min, as supported by representative tandem mass spectrometry. Hydrolysis rates in human serum were determined for both of the deprotected monomers (i.e., HBC and CPM) prior to their incorporation into copolymers as shown in FIGS. 3A-3D. These studies suggest that the respective rates of hydrolysis for the aliphatic (HBC) and phenyl (CPM) ester linked drugs are not significantly affected by the presence of serum proteins. A significant difference in the relative hydrolysis rates for these monomers was observed with CPM showing nearly 50% drug release at 24 h while HBC required 120 h to reach a similar percent release (FIG. 3A). This apparent difference likely arises from the improved hydrolytic susceptibility of CPM's phenyl ester functionality, which forms a resonance-stabilized phenoxide as a leaving group.

Figure 3B:
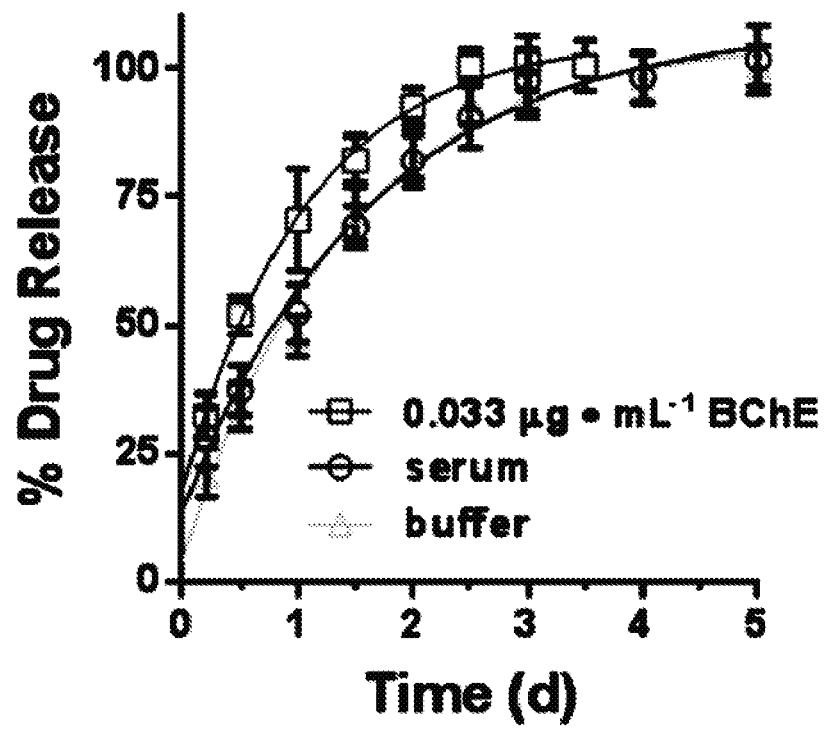
Figure 3C:
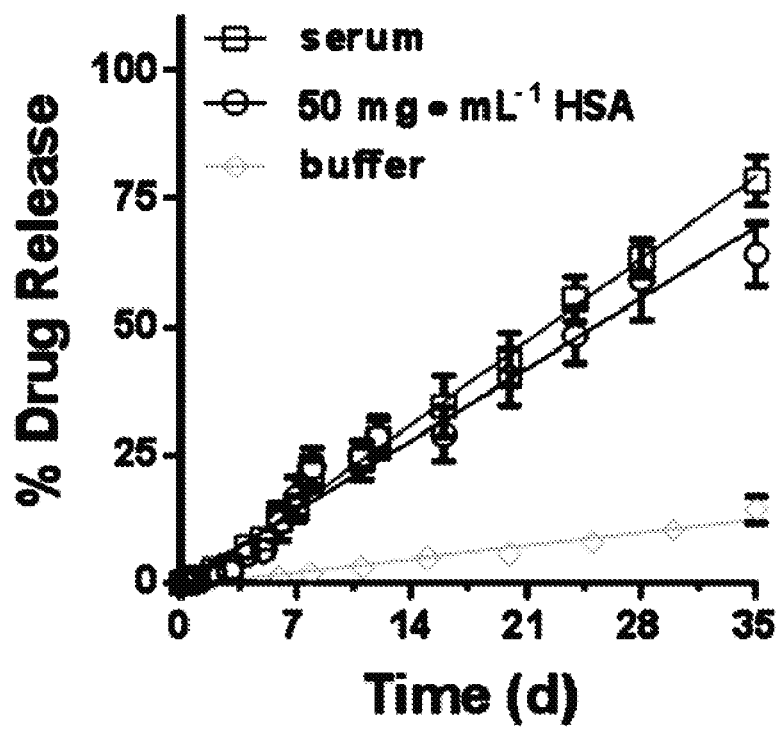

Butyrylcholinesterase (BChE) is a human enzyme generated by the liver that freely circulates in the blood to facilitate the breakdown of many drugs. The addition of increasing concentrations of BChE to solutions of the prodrug monomer in buffer increases hydrolysis of both types of ester bonds as noted by the enhanced pseudo-first order release profiles for deprotected HBC and CPM monomers (FIGS. 3A and 3B). Without the added enzyme present, the release kinetics transition from an apparent first order kinetics to near zero-order for the deprotected HBC monomer suggesting that this particular monomer is more responsive to a natural esterase than the more labile phenolic ester monomer (CPM) (FIGS. 3A and 3B). Although the release profiles of poly(O950-co-HBC) in serum and buffer are near zero-order, the kinetics of hydrolysis and subsequent release of free drug were observed to be faster in serum than buffer (FIG. 3C). In efforts to probe this observation, the copolymers were incubated in buffer with the addition of 50 mg/mL human serum albumin (HSA) and assayed for free drug as a function of time. In these studies, the inclusion of HSA was shown to increase release kinetics to rates similar to those observed in serum (FIG. 3C). This observation is hypothesized to arise from the association of the unimeric copolymer with proteins found in serum (e.g. human serum albumin) to produce polymer conformations with improved solvation of the pendent ester bonds. Slow release kinetics for end-linked Cipro-polymer conjugates have been observed. For example, approximately 20-25% Cipro release was observed over 35 days from multi-armed and star shaped homopolymers of poly(c-caprolactone) and polylactide that were end-functionalized with 3-8 mol % of drug.

Figure 3D:
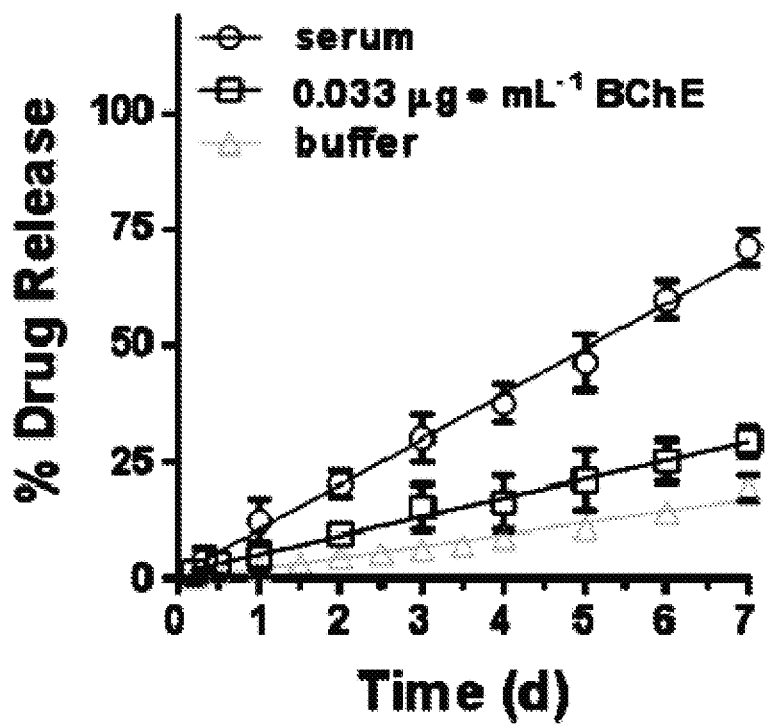

The addition of BChE to poly(O950-co-CPM), in buffer resulted in a slight increase in the hydrolysis rate relative to buffer alone (FIG. 3D). This increase was, however, not as large as samples incubated in serum suggesting the importance of serum proteins in facilitating ester hydrolysis for polymer backbone-linked drugs. These findings suggest that the presence of enzyme alone may not be sufficient to significantly improve hydrolysis rates for esters found within low dielectric environments, such as the case with many polymer backbones. In contrast, the large increase in drug release observed for monomers incubated with the enzyme (FIGS. 3A and 3B) can be attributed to the lack of a polymerized chemical backbone, which may allow BChE to access the ester groups promoting faster cleavage rates than those observed in serum. Comparison of copolymers containing phenyl-(CPM) and aliphatic-(HBC) esters shows that poly(O950-co-CPM) hydrolyzed more rapidly than poly(O950-co-HBC) with approximately 50% drug release observed at 120 h and 21 days respectively. In both cases however incorporation of the ester-linked drug into copolymers resulted in a substantial decrease in hydrolysis rates relative to the parent monomers (FIGS. 3C and 3D).

Figure 3E:
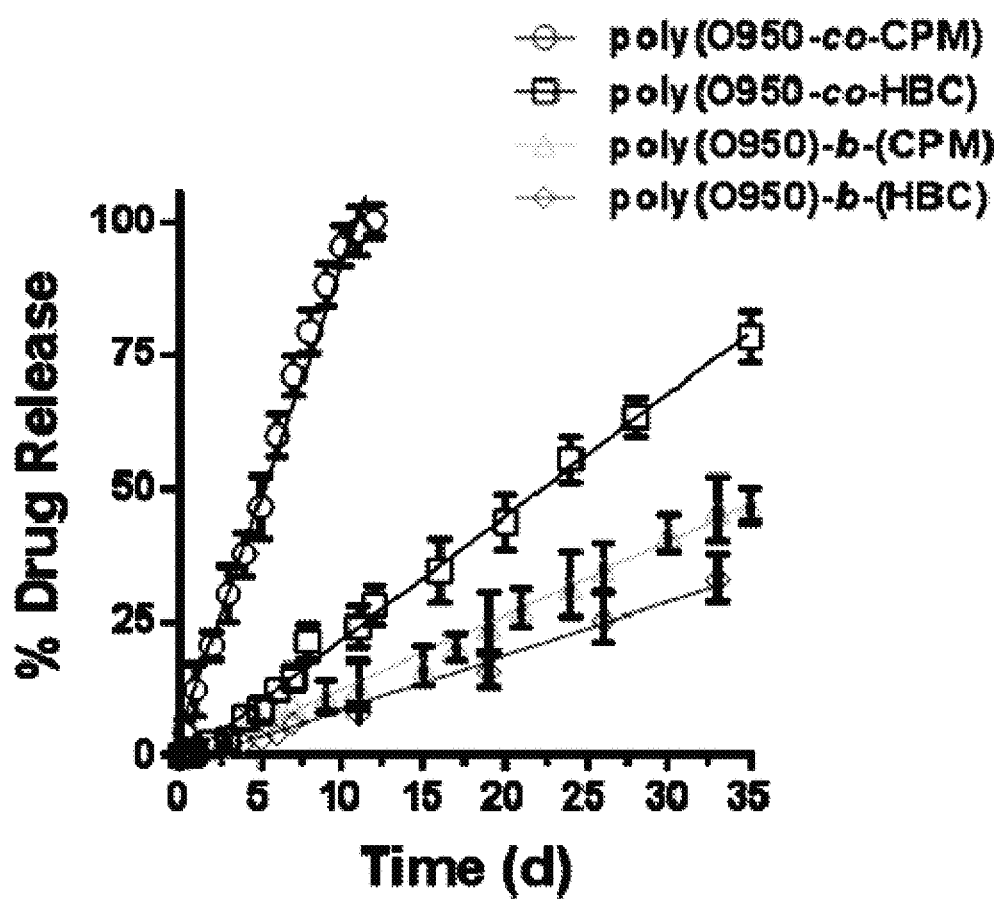

The effect of polymer architecture on drug release behavior was also evaluated by synthesizing diblock copolymers consisting of a hydrophilic poly(O950) corona forming segment and a hydrophobic poly(HBC) or poly(CPM) core forming segment, as described above. As shown in FIG. 3E, sequestration of the prodrug residues to a hydrophobic core results in a significant decrease in ester hydrolysis rates relative to the molecularly soluble constructs. It is important to note that although the rate of drug release from the diblocks are slower than the copolymers, the total drug content for diblocks are greater (30 wt. % drug for poly(O950)-b-(HBC) and 34 wt. % drug for poly(O950)-b-(CPM) vs. 16 wt. % drug for poly(O950-co-HBC) and 16.7 wt. % drug for poly(O950-co-CPM)). Consequently, there is a larger quantity of drug released from the diblock copolymers over a longer period of time as compared to the copolymers.

In Vitro Polymer Toxicity and Efficacy.

Figure 4C:
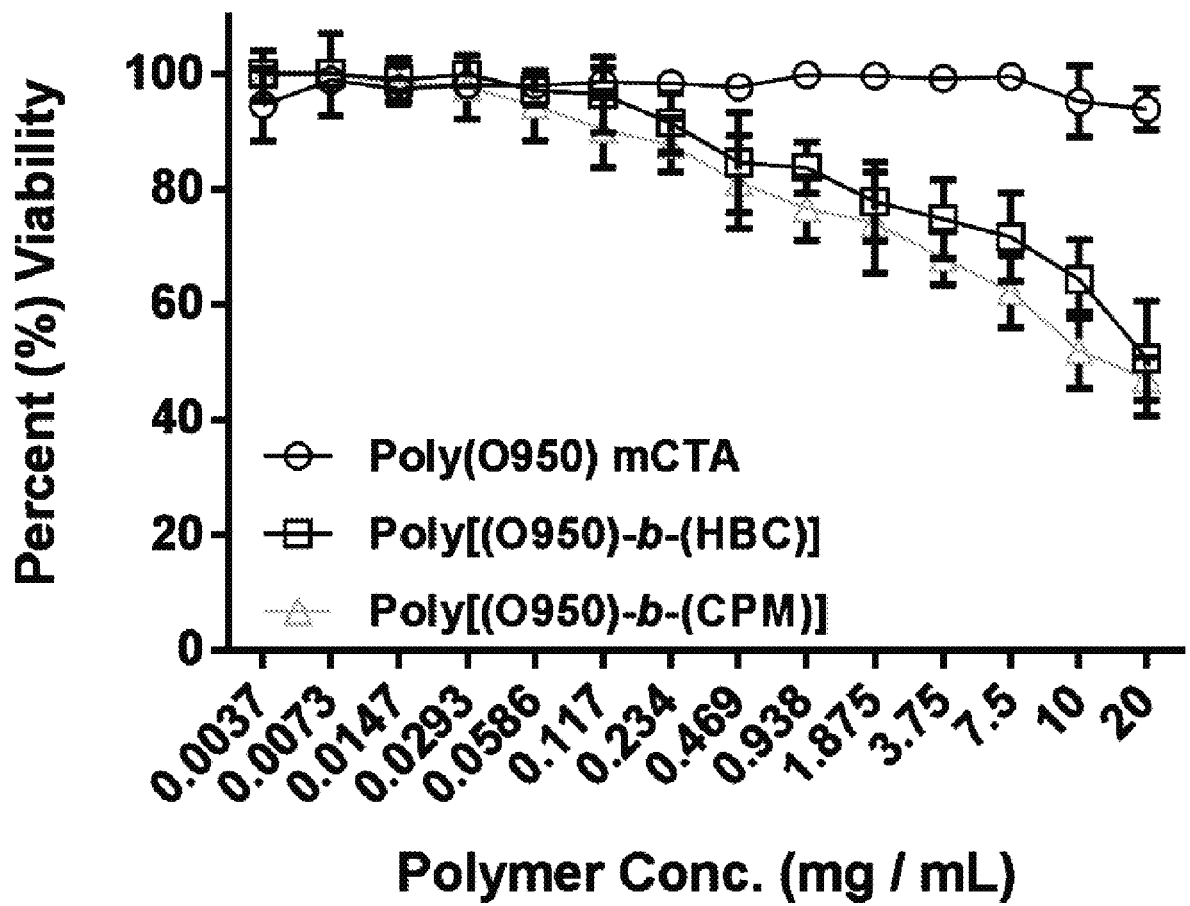
FIG. 4C compares RAW 264.7 cell viability in the presence of both diblock copolymers was quantified using an MTS assay over a wide polymer dose range (mg/mL). After 24 h, both polymer constructs exhibit a dose dependent toxicity with cell viability measured below 80% with polymer concentrations greater than about 1 mg/mL.
Figure 5A:
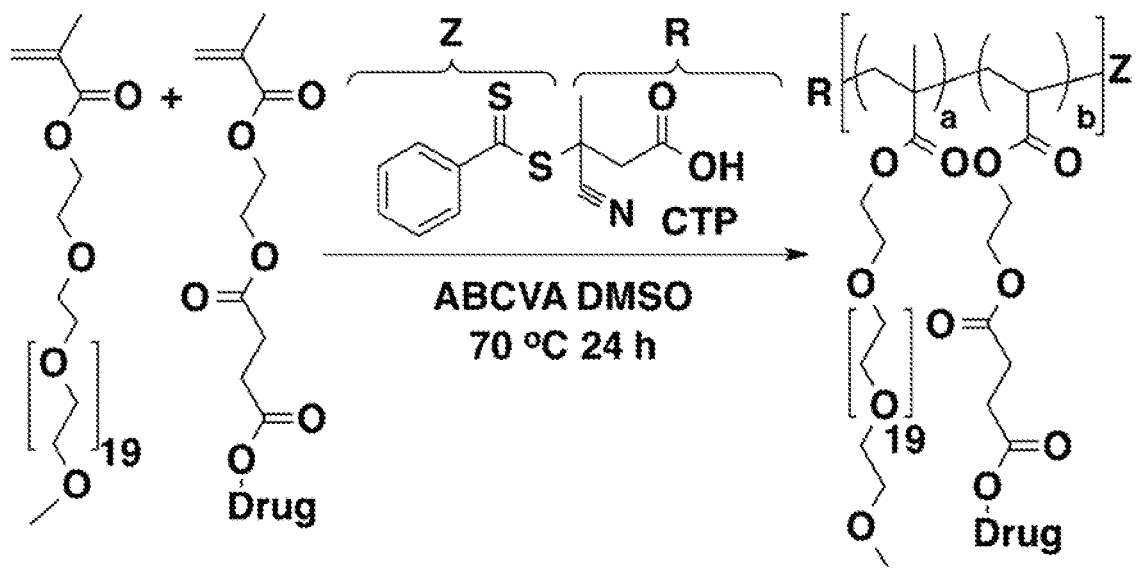
FIG. 5A is a schematic illustration of the preparation of representative prodrug copolymers of the invention, poly(O950-co-DtSMA) and poly(O950-co-CamSMA), by RAFT polymerization.
Figure 5A:
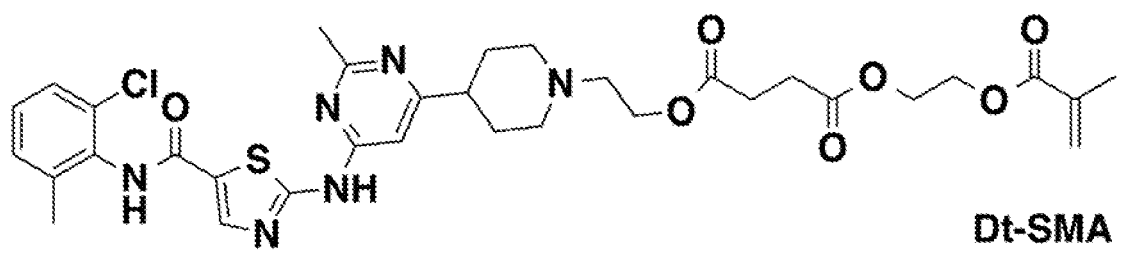
Figure 5A:
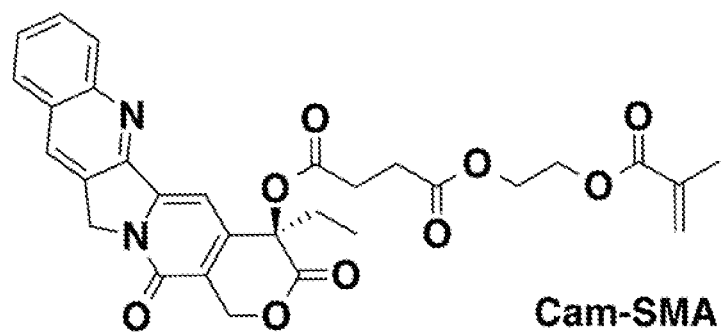
Figure 5B:
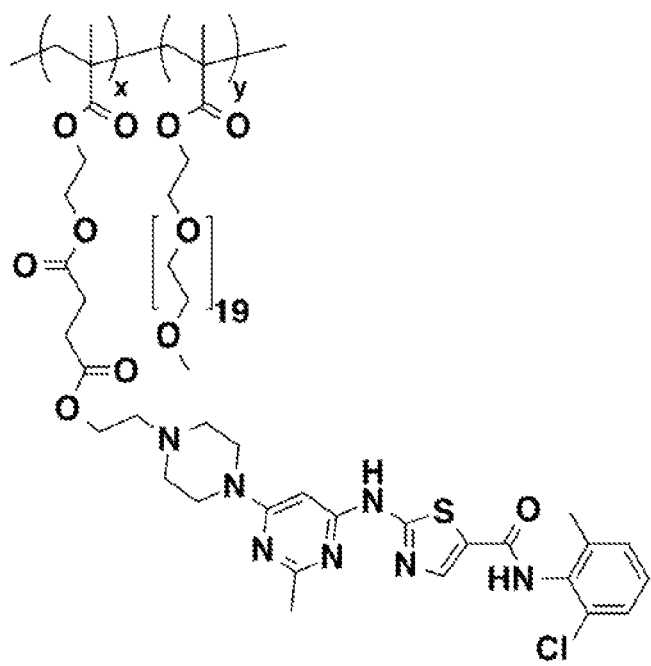
FIG. 5B is a schematic illustration of a representative dasatinib prodrug copolymer of the invention, poly(O950-co-DtSMA).
Figure 5C:
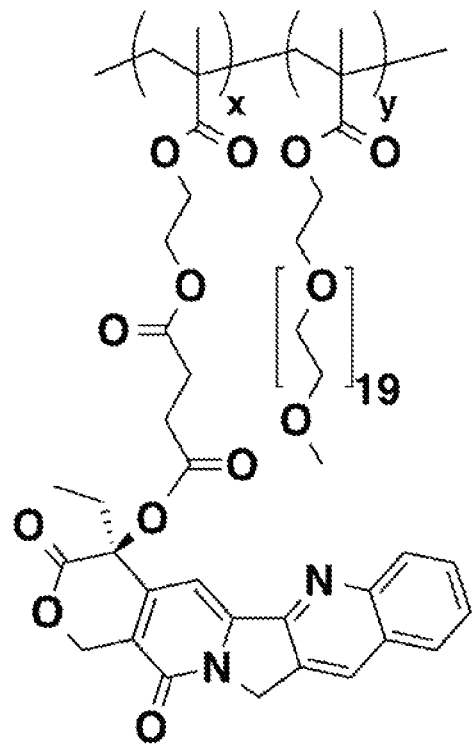
FIG. 5C is a schematic illustration of a representative camptothecin prodrug copolymer of the invention, poly(O950-co-CamSMA).
Figure 6:
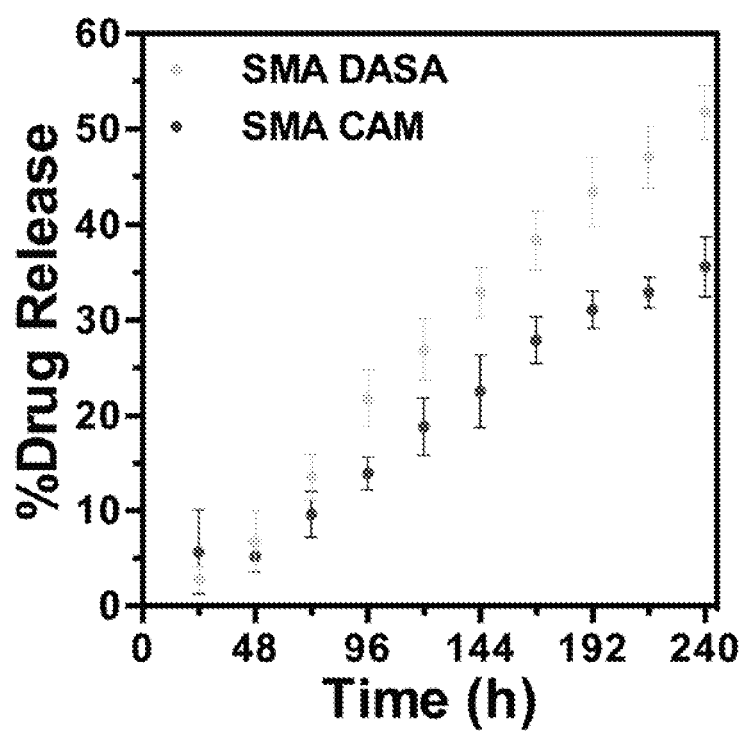
FIG. 6 compares drug release in 100% human serum for representative copolymers of the invention, poly(O950-co-DtSMA) and poly(O950-co-DtSMA), SMA DASA and SMA CAM, respectively, in the figure.

The cultured cell biocompatibility of the polymeric prodrugs was characterized in RAW 264.7 cells. Cells were incubated with varying concentrations of the copolymer and diblock copolymer prodrugs for 24 h. No notable (<80% cell viability) toxicity was observed for both the poly(O950-co-HBC) and poly(O950-co-CPM) even at polymer concentrations of 20 mg/mL (FIG. 4A). In contrast, the diblock copolymer constructs demonstrated dose dependent toxicity with RAW cell viability falling below 80% at polymer concentrations exceeding approximately 1 mg/mL (FIG. 4C). This toxicity is likely a result of interactions of the lightly charged polyCipro segments with cell membranes upon internalization and subsequent acidification in endosomal compartments. This phenomenon has been previously reported for other positively charged systems such as cationic polystyrene nanospheres (~40-50 nm) in RAW 264.7 cells.

Based on the copolymer's lack of toxicity in RAW cells at elevated concentrations (FIG. 4A), poly(O950-co-HBC)

and poly(O950-co-CPM) were selected for further studies to evaluate efficacy using a co-culture challenge assay with *Burkholderia thailandensis* infected RAW 264.7 cells (FIG. 4B). Here *B. thailandensis* was used as a surrogate model for the evaluation of *B. pseudomallei* infectivity. The dose response curve of free Cipro was, consistent with literature minimum inhibitory concentrations (MIC) of 10 μg/mL or 0.03 mM. Evaluation of poly(O950-co-HBC) in this assay yielded an MIC of 2000 μg/mL (6 mM) polymerized prodrug, which is consistent with hydrolysis studies where approximately 1-2% drug release is observed at 24 h in 100% serum (FIG. 3C). In contrast, co-culture studies conducted with poly(O950-co-CPM) resulted in a 10-fold reduction in the MIC to 200 μg/mL (0.6 mM) polymerized prodrug (FIG. 4B). These results are consistent with trends observed in the drug release studies and show that the phenyl ester linked Cipro releases more active drug over the timescale of this in vitro co-culture model as a result of higher drug cleavage rates (FIG. 3D).

Additional representative examples of prodrug copolymers of the invention and their related diblock copolymers include dasatinib (Dt or DASA) and camptothecin (Cam or CAM) prodrug copolymers and related diblock copolymers. The preparation and characterization of these representative copolymers and diblock copolymers is described in Example 2. As described in Example 2, in certain embodiments, these copolymers include poly(ethylene glycol) constitutional units (i.e., poly(Cam-SMA-co-O950) and poly(Dt-SMA-coO950)), and in other embodiments, these diblock copolymers include ampholyte constitutional units (poly[(MA-co-DMAEMA)-b-(Dt-SMA)]).

Reversible addition-fragmentation chain transfer (RAFT) polymerization was employed to prepare dense polyethylene glycol methacrylate brushes containing the chemotherapeutic agents dasatinib and camptothecin. These agents were covalently linked to the macromolecular scaffold via direct copolymerization of prodrug monomers with polyethylene glycol methacrylate (O950). Hydrolysis studies of the hydrophilic copolymers conducted in human serum showed 33±1.7 and 22±2.4% drug release for the ester linked dasatinib and camptothecin respectively. Polymer morphology was also shown to play a key role in drug release rates with copolymers distributed within a hydrophilic copolymer segment showing higher rates than materials where the hydrophobic drug molecules were localized in discreet hydrophobic blocks. The latter materials were shown to self assemble into nanoparticles where the drug block was separated from the aqueous phase. Live animal imaging in PC-3 (human prostate cancer cell line) tumor xenographs showed that the fluorescently labeled copolymer brushes were trafficked to the tumor 24 hours post injection. Ex vivo analysis of the harvested tissues showed that polymer accumulated preferentially in the tumor and kidneys. In vitro cytotoxicity measurements conducted in K562-S and K562-R cells demonstrated ability of the macromolecular conjugates to release the covalently linked drugs in an active form.

FIG. 5A is a schematic illustration of the preparation of representative prodrug copolymers of the invention, poly (O950-co-DtSMA) and poly(O950-co-CamSMA), by RAFT polymerization. FIG. 5B is a schematic illustration of a representative dasatinib prodrug copolymer of the invention, poly(O950-co-DtSMA). FIG. 5C is a schematic illustration of a representative camptothecin prodrug copolymer of the invention, poly(O950-co-CamSMA). FIG. 6 compares drug release in 100% human serum for representative copolymers of the invention, poly(O950-co-DtSMA) and poly(O950-co-DtSMA), SMA DASA and SMA CAM, respectively, in the figure. FIG. 7 is a schematic illustration of a representative combined dasatinib/camptothecin prodrug diblock copolymer of the invention, poly(O950-co-CamSMA)-b-(DtSMA). The preparation and properties of these polymers is described in Example 2.

Prodrug Copolymers Having Zwitterionic Constitutional Units

In certain embodiments, the copolymers of the invention include zwitterionic constitutional units. The preparation and properties of representative ciprofloxacin prodrug monomers and related copolymers having zwitterionic constitutional units are described in Example 3. In addition to having zwitterionic constitutional units, these representative ciprofloxacin prodrug monomers and related copolymers have cleavable linkers (e.g., phenolic ester groups) that efficiently release ciprofloxacin at therapeutically effective rates.

In the following representative embodiments, the zwitterionic group of the constitutional units is a carboxybetaine (CBM).

FIG. 8 presents schematic illustrations of the preparations of a representative copolymer of the invention [poly(CBM-co-CTM)] and a representative diblock copolymer of the invention [poly(CBM-co-CTM)-b-(CTM)].

FIG. 9A compares drug release from a representative copolymer of the invention [poly(CBM-co-CTM)] and a representative diblock copolymer of the invention [poly (CBM-co-CTM)-b-(CTM)]. The diblock copolymer shows binary release profiles presumably as a result of fast hydrolysis of the first segment with concurrent slow release form the second hydrophobic block.

FIG. 9B compares co-culture data for a representative copolymer of the invention [poly(CBM-co-CTM)] and a representative diblock copolymer of the invention [poly (CBM-co-CTM)-b-(CTM)]. Both the copolymer and diblock copolymer show similar antibiotic activity at comparable ciprofloxacin prodrug concentrations despite that a significant portion of the diblock copolymer bound ciprofloxacin release quite slowly relative to the timescale of the experiment. This phenomenon could be a result of higher intracellular accumulation of the diblock.

FIG. 9C shows that pre-incubation of a representative copolymer of the invention [poly(CBM-co-CTM)] in serum for 24 hours increases the antibiotic activity of the copolymer in planktonic cultures because it allows some of the ciprofloxacin to be released prior to infection.

FIGS. 10A-10D illustrate in vivo biocompatibility for a representative copolymer of the invention [poly(CBM-co-CTM)] compared to phosphate buffered saline control (PBS): LTH TNF-alpha (10A); BALF TNF-alpha (10B); % Neutrophil (10C); and % Weight Change (10D).

Prodrug Copolymers Having Ampholyte Constitutional Units

In certain embodiments, the copolymers of the invention include ampholyte constitutional units. In addition to having ampholyte constitutional units, these representative dasatinib prodrug monomers and related copolymers have cleavable linkers that efficiently release dasatinib at therapeutically effective rates.

The preparation and characterization of these representative copolymers and diblock copolymers is described in Example 2. As described in Example 2, in certain embodiments, these diblock copolymers include ampholyte constitutional units (poly[(MA-co-DMAEMA)-b-(Dt-SMA)]).

FIG. 11 is a schematic illustration of a representative diblock copolymer of the invention, poly(methacrylic acidco-dimethylaminoethyl methacrylate)-b-(DtSMA) [poly (MA-co-DMAEMA)-b-(DtSMA)], useful for the delivery of dasatinib.

Figure 12:
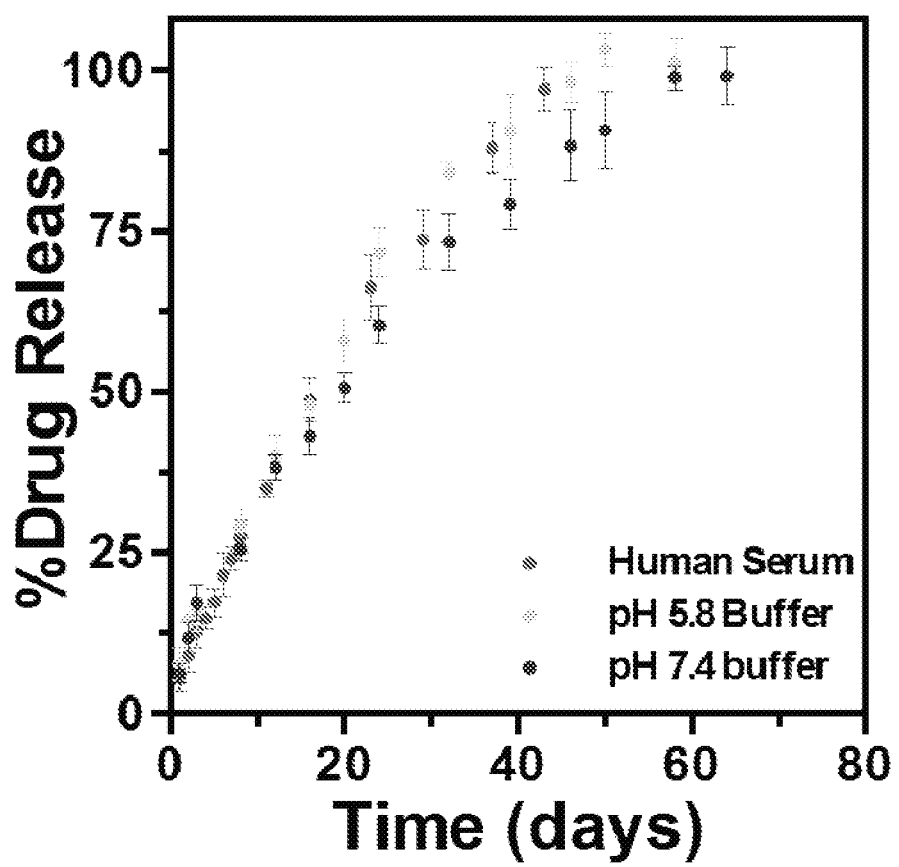
FIG. 12 compares drug release (dasatinib) for a representative diblock copolymer of the invention [poly(MAA-co-DMAEMA)-b-(DtSMA)] in human serum, pH 5.8 buffer, and pH 7.4 buffer.

FIG. 12 compares drug release (dasatinib) for a representative diblock copolymer of the invention [poly(MA-co-DMAEMA)-b-(DtSMA)] in human serum, pH 5.8 buffer, and pH 7.4 buffer. In this architecture, the dasatinib makes up a discrete hydrophobic block stabilized by an ampholyte block. The diblock copolymer self assembles at pH 7.4 to form micelles at reasonable block ratios. The self assembly significantly reduces the ester hydrolysis rate.

Pro-Apoptotic Peptide BIM Prodrug Monomers and Related Copolymers

In representative embodiments, the present invention provides pro-apoptotic peptide BIM prodrug monomers and related copolymers. The preparation and properties of representative ciprofloxacin prodrug monomers and related copolymers are described in Example 4. The representative pro-apoptotic peptide BIM prodrug monomers and related copolymers have enzymatically cleavable linkers (amino acid sequence FKFL cleavable by cathepsin B) that efficiently release ciprofloxacin at therapeutically effective rates.

Peptides derived from the third Bcl-2 homology domain (BH3) renormalize apoptotic signaling by antagonizing pro-survival Bcl-2 family members. They serve as a model for potential peptide and peptide-like drugs that possess potential therapeutic activities but are limited by delivery barriers including short circulation half-lives and poor penetration into cells. A diblock polymeric micelle carrier for the BIM BH3 peptide has been recently described that demonstrated anti-tumor activity in a xenograft model. However, the disulfide linkage used to conjugate the BIM peptide was shown to have non-optimal blood stability, and here we describe an enzyme-labile BIM monomer that increases blood stability but is cleaved to release the drug inside of human ovarian cancer cells. Employing RAFT polymerization, a multifunctional diblock copolymer was synthesized with the peptide macromonomer composed of the pro-apoptotic peptide BIM capped with a four amino acid substrate (FKFL) for the endo/lysosomal enzyme cathepsin B. The first block was made as a macro-chain transfer agent (CTA) composed of copolymers of the peptide with poly-ethylene glycol methacrylate (PEGMA) of two segment lengths. The other polymer block was pH-responsive. High performance liquid chromatography and coupled mass spectrometry showed that incubation with cathepsin B specifically cleaved the FKFL linker and released active BIM peptide with PEGMA300 but not with PEGMA950. The polymer was found to protect the FKFL linker from degradation in human serum. Dynamic light scattering (DLS) demonstrated pH-dependent micelle disassembly (25 nm polymer micelles at pH 7.4 versus 6 nm unimers at pH 6.6), and a red blood cell lysis assay showed a corresponding increase in membrane destabilizing activity (<1% lysis at pH 7.4 versus 95% lysis at pH 6.6). The full carrier-drug system successfully induced apoptosis in SKOV3 ovarian cancer cells in a dose-dependent manner, in comparison to a control polymer containing a scrambled BIM peptide sequence. Mechanistic analysis verified target-dependent activation of caspase 3/7 activity (8.1-fold increase), and positive annexin V staining (72% increase). The increased blood stability of this enzyme-cleavable peptide polymer design, together with the direct polymerization approach that eliminated post-synthetic conjugation steps.

Synthesis and Characterization of a Cathepsin B-Cleavable Diblock Copolymer for Intracellular BIM Delivery.

A cathepsin B-cleavable BIM peptide macromonomer was synthesized containing BIM capped with the FKFL cathepsin B substrate, flanked on either side by a six-carbon spacer (Ahx), and functionalized on its N-terminus with meth acrylamide (MaAhxFKFLAhxBIM). A cathepsin B-cleavable peptide macromonomer containing a scrambled BIM sequence (MaAhxFKFLAhxScrBIM) was synthesized as a control. The molecular weights of the peptide macromonomers (3437 Da) were confirmed by mass spectrometry.

Figure 13:
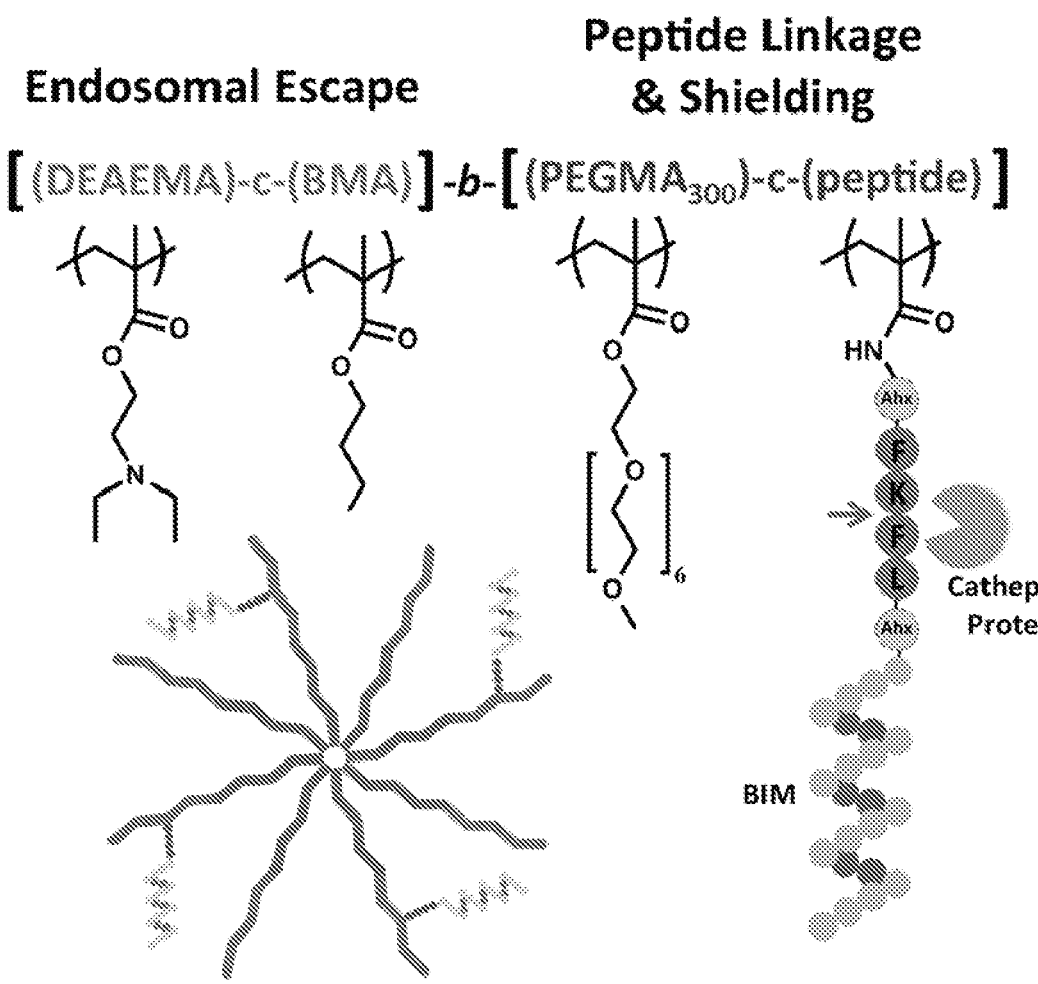
FIG. 13 is a schematic illustration of a representative diblock copolymer of the invention useful for the delivery of a peptide therapeutic: a cathepsin-B cleavable diblock copolymer for the intracellular delivery and release of the pro-apoptotic peptide BIM (PolBIM). The first block drives micelle formation at physiological pH (7.4) and destabilizes membranes and facilitates endosomal escape at acidic pH values (5.8-6.6). The second block contains PEG units for biocompatibility and stability and a methacrylamido-peptide macromonomer consisting of BIM capped with a four amino acid (FKFL) cathepsin B substrate flanked on either side by a six carbon spacer (aminohexanoic acid (Ahx)). Cleavage at the FKFL linker by cathepsin B specifically releases BIM inside the endosomes of target cells.

Using RAFT polymerization, the peptide macromonomers were directly integrated into corresponding diblock copolymers (FIG. 13) (PolBIM and PolScrBIM). Each polymer contained a pH-responsive endolytic block for cytosolic delivery and a hydrophilic block for solubility, biocompatibility, and peptide stability. For the first block of each polymer, a poly[(DEAEMA)-co(BMA)] macroCTA was synthesized with a molecular weight ($M_n$) of 16,600 g/mol and a narrow polydispersity (PDI) of 1.07. A polymer formulation of 60% DEAEMA and 40% BMA was targeted, as this composition has been shown to possess optimal pH-responsive membrane destabilizing activity and trigger the endosomal release of biologic drugs. For the second polymer block, PEGMA$_{300}$ (96 mol %) and peptide macromonomer (4 mol %) were copolymerized. PEGMA$_{300}$ was chosen for its solubility, safety and favorable pharmacokinetic properties in vivo. The molecular weights and PDIs of PolBIM and PolScrBIM were determined to be 28,700 Da and 29,300 Da, and 1.12 and 1.07, respectively. RP-HPLC analysis of aliquots collected at reaction start at end times was used to determine the peptide content of the polymers. PolBIM and PolScrBIM were found to contain 0.9 and 0.8 peptide units per polymer chain, respectively.

Cathepsin B-Mediated Release of the Pro-Apoptotic Peptide BIM.

Cathepsin B is known to cleave the FKFL substrate between the lysine and C-terminal phenylalanine residues. Consequently, cathepsin B cleavage of the peptide macromonomers (MW 3437 Da) at the FKFL linker should yield a 2980 Da product consisting of BIM or scrambled BIM modified on the N-terminus with FLAhx. To ensure the FLAhx modification did not impact BIM's pro-apoptotic activity, the ability of FLAhxBIM to induce cytochrome C release from the mitochondria of granta-519 tumor cells was measured and compared to unmodified BIM. At a concentration of 10 µM, both FLAhxBIM and BIM induced >90% cytochrome c release in comparison to a positive 1% Triton-X100 control. A negative control protein did not induce any measurable release of cytochrome c.

Figure 14A:
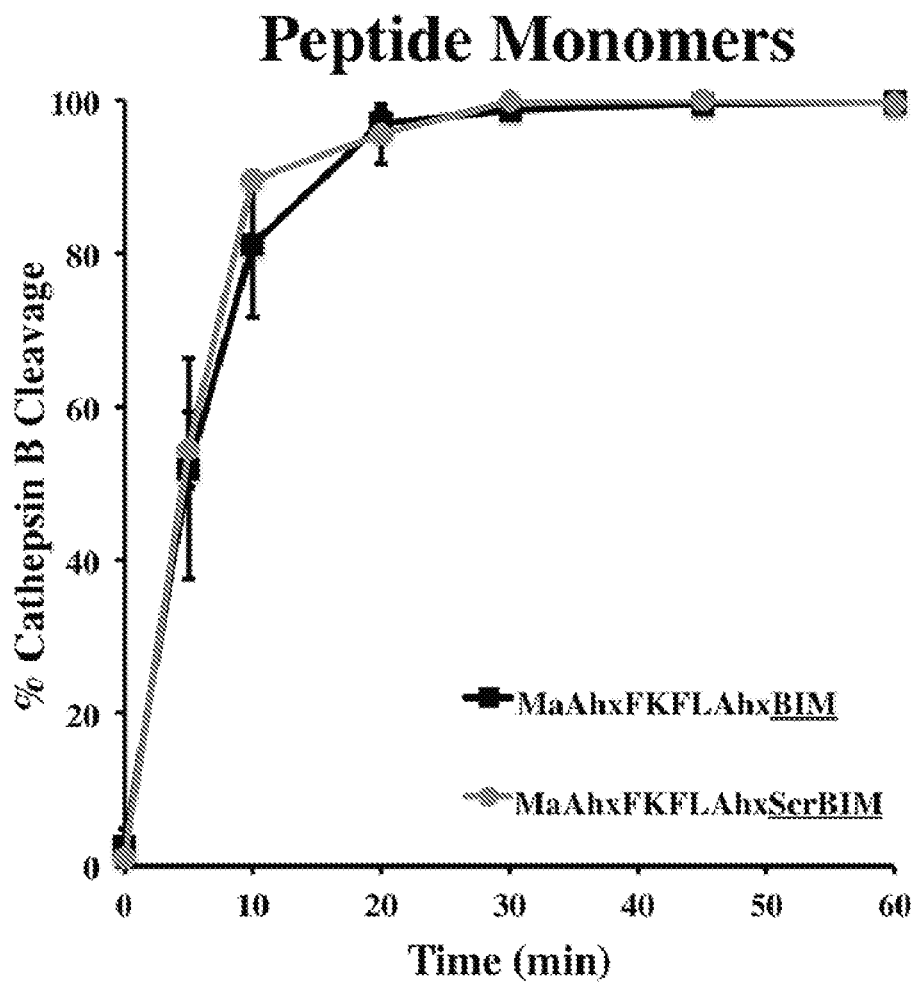
FIGS. 14A and 14B compare cathepsin B cleavage of the FKFL peptide linker to release BIM peptide for peptide monomers MaAhxFKFLAhxBIM and control (MaAhxFKFLAhxScrBIM) (14A) and a representative diblock copolymer of the invention (PolBIM) and control (PolScrBIM) (14B). At various time points of incubation with cathepsin B the reactions were stopped by addition of a thioprotease inhibitor (E-64) and reaction products were analyzed by RP-HPLC and MS. Peptide release from the backbone of the diblock copolymer PolBIM was visible by protein gel analysis, with a BIM peptide band appearing and increasing in intensity with incubation time.
Figure 14B:
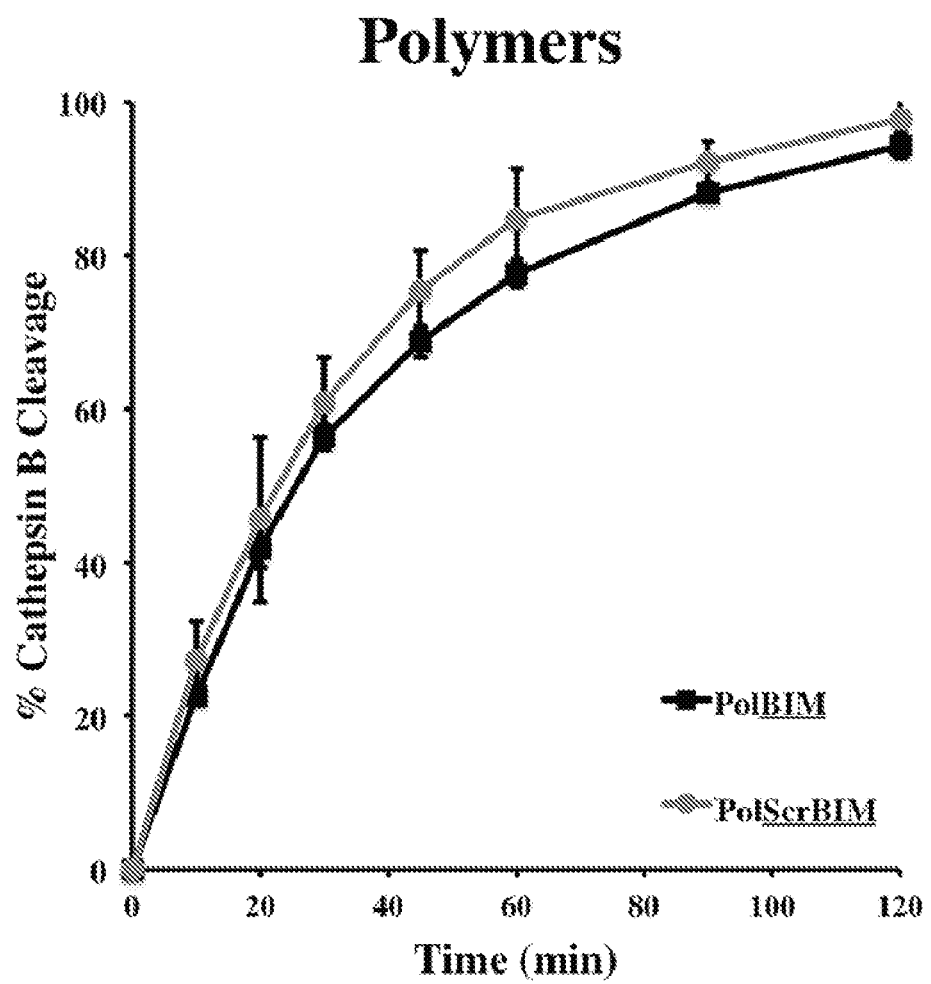

To confirm cathepsin B-mediated cleavage at the FKFL linker, peptide macromonomers and polymers were incubated with human liver cathepsin B enzyme and degradation products were analyzed overtime by RP-HPLC and MS. Cathepsin B rapidly and specifically cleaved MaAhxFK-FLAhxBIM and MaAhxFKFLAhxScrBIM at the FKFL linker, with 100% cleavage observed by 20 minutes (FIG. 14A). Likewise, Cathepsin B cleaved PolBIM and Pol ScrBIM at the FKFL linker to release the desired (2980 Da) peptide product (FIG. 14B), although the kinetics of polymer cleavage were significantly slower than for the peptide monomers alone. Cathepsin B-mediated release of peptide from PolBIM could also be visualized by protein gel analysis, with a peptide band appearing and intensifying with increased incubation time. In combination, these findings suggest cathepsin B will release active BIM peptide from its polymer carrier within the endosomes of cancer cells.

Stability of the FKFL Linker in Human Serum.

To investigate the susceptibility of the FKFL peptide linker to extracellular protease degradation, the peptide macromonomers (MaAhxFKFLAhxBIM and MaAhxFKFLAhxScrBIM) and their corresponding polymers (PolBIM and PolScrBIM) were incubated in human serum at 37° C. At time points ranging from 0 to 12 hours, peptide products were extracted from the serum into acetonitrile and analyzed by MALDI-TOF MS. For both MaAhxFKFLAhxBIM and MaAhxFKFLAhxscrBIM, intact peptide monomer (3437 Da) was detectable after 12 hours. However, low levels of cleavage at the FKFL linker did occur, with the slow appearance of a 2980 Da peak observed over time. The polymers were found to protect against degradation at the FKFL linker, as the 2980 Da peak was absent at all time points.

Micelle Sizing and pH-Responsive Membrane Destabilizing Activity.

To confirm pH-dependent micelle formation, dynamic light scattering (DLS) was employed to measure particle sizes in phosphate buffers of varying pH (5.8-7.4). At pH 7.4, PolBIM and PolScrBIM assembled into micelles with hydrodynamic diameters of 25 nm and 26 nm, respectively. As the pH was decreased step-wise to 5.8, the micelles disassembled into unimers with diameters of 6 nm.

The polymers' corresponding pH-responsive membrane destabilizing activity was evaluated using a red blood cell hemolysis assay. The polymers (60 μg/mL) were incubated with red blood cells at varying pH values, and the release of heme groups (hemolysis) was measured spectrophotometrically (abs 541 nm). At pH 7.4, no significant red blood cell lysis was observed. However, as the pH was lowered to the values found in early (6.6) and late endosomes (5.8), a sharp increase in hemolysis was observed, with >95% lysis observed at pH 6.6. These findings demonstrate the potential of these polymers as pH-responsive intracellular delivery vehicles.

Cancer Cell Viability.

To assess the biological activity of PolBIM, a cytotoxicity study was conducted in SKOV3 ovarian cancer cells using an MTS cell viability assay (FIG. 15). PolBIM was found to potently induce cell death in a dose dependent fashion. After 96 hours of treatment with 10 μM PolBIM, only 25% of cells remained viable. In contrast, PolScrBIM exhibited minimal toxicity with greater than 90% cell viability observed at all polymer concentrations.

Induction of Apoptotic Markers: Caspase 3/7 Activity and Annexin V Staining.

Activation of caspase-3 and caspase-7 is a critical step in the execution of apoptosis, which was measured using a profluorescent enzyme substrate. SKOV3 cells that were treated with polymer containing the active BIM sequence (PolBIM) exhibited a dose-dependent increase in caspase 3/7 activity (FIG. 16A), with 10 μM PolBIM resulting in more than 8-fold greater activity. In contrast, cells treated with PolScrBIM showed no change relative to untreated cultures.

Early in apoptosis, phosphatidylserine (PS) is translocated from the inner to outer plasma membrane, becoming exposed extracellularly. Consequently, apoptotic cells can be identified by staining with the human anti-coagulant annexin V, which binds to PS with high affinity. Treatment with PolBIM (10 μM) significantly increased annexin V staining of SKOV3s, with 87% of cells staining positive after 72 hours (FIG. 16B). In contrast, only 15% of cells treated with PolScrBIM stained positive. In combination, these findings indicate that PolBIM kills cancer cells by inducing apoptosis.

In certain embodiments, the copolymers and related diblock copolymers of the invention include enzyme labile peptide linkers, such as those cleaved by endo/lysosomal proteases. These linkers are chemically stable in the bloodstream and rapidly and specifically cleaved upon internalization into target cells. Cathepsin B, a ubiquitous cysteine protease in endo/lysosomes, is an ideal candidate for this application. Cathepsin B is only found extracellularly in rare pathological conditions.

A representative enzyme labile peptide linker useful in the practice of the present invention is a four amino acid cathepsin B substrate, FKFL, that is rapidly cleaved between the lysine and C-terminal phenylalanine residues. In copolymer embodiments, the substrate was flanked on each side by a six carbon spacer, 6-aminohexanoic acid (Ahx), to spatially separate the site of enzymatic cleavage from the peptide drug and polymer backbone. The N-terminus of the BIM peptide was capped with the linker. Consequently, cathepsin B cleavage released a BIM peptide product modified on its N-terminus with FLAhx. Using a cytochrome C release assay, this modification was found to have no impact on BIM's pro-apoptotic activity. The linker-peptide sequence was functionalized on its N-terminus with methacrylamide and polymerized directly into a diblock copolymer (PolBIM) designed to enhance BIM's pharmacokinetic and tumor delivery properties. The first polymer block contained a hydrophobic formulation to drive micelle formation at physiological pH and disrupt membranes at the decreased pH values found in endo/lysosomes. The second block was composed of peptide and long-chain polyethylene glycol monomers for stability and biocompatibility. A cathepsin-B cleavable control polymer was synthesized containing a scrambled BIM peptide sequence (PolScrBIM).

To investigate the susceptibility of the FKFL linker to cathepsin B cleavage, both peptide monomers and polymers were incubated with cathepsin B enzyme and the degradation products were analyzed over time by RP-HPLC and MS. Cathepsin B cleaved both the peptide monomers and peptide polymers at the FKFL linker (FIGS. 14A and 14B). Polymerization was found to slow the rate of enzymatic cleavage, but greater than 94% of polymer cleavage was still complete by 2 hours. To assess the susceptibility of the linker to cleavage within the bloodstream, the peptide monomers and polymers were incubated in human serum and at various time points the degradation products were analyzed by MALDI-TOF MS. The peptide monomers were found to cleave at the FKFL linker, but only at very low levels. Completely intact peptide monomer was still detectable at time points as late as 12 hours. Furthermore, extracellular degradation by serum proteases was abrogated by the polymer, with cleavage products undetectable even at later time points. In combination, these findings suggest that the polymer strikes an advantageous balance between protecting linker degradation in circulation and permitting cathepsin B access and peptide release upon internalization.

pH-responsive membrane destabilizing activity is known to be critical for the intracellular delivery of biologic drugs. After polymer micelles are endocytosed, the acidic environment triggers them to disassemble into unimers, destabilize the endosomal membrane, and release their cargo into the cell cytosol. The pH-dependent activity of PolBIM and Pol SrBIM was assessed by dynamic light scattering and a red blood cell hemolysis assay. At physiological pH, both polymers formed micelles with hydrodynamic diameters of approximately 25 nm. When the pH was decreased to endosomal values (6.6-5.8) the measured diameters dropped to 6 nm, indicating micelle disassembly. This decrease correlated strongly with an increase in the polymers' hemolytic activity suggesting the polymers will be endolytically active.

Figure 15:
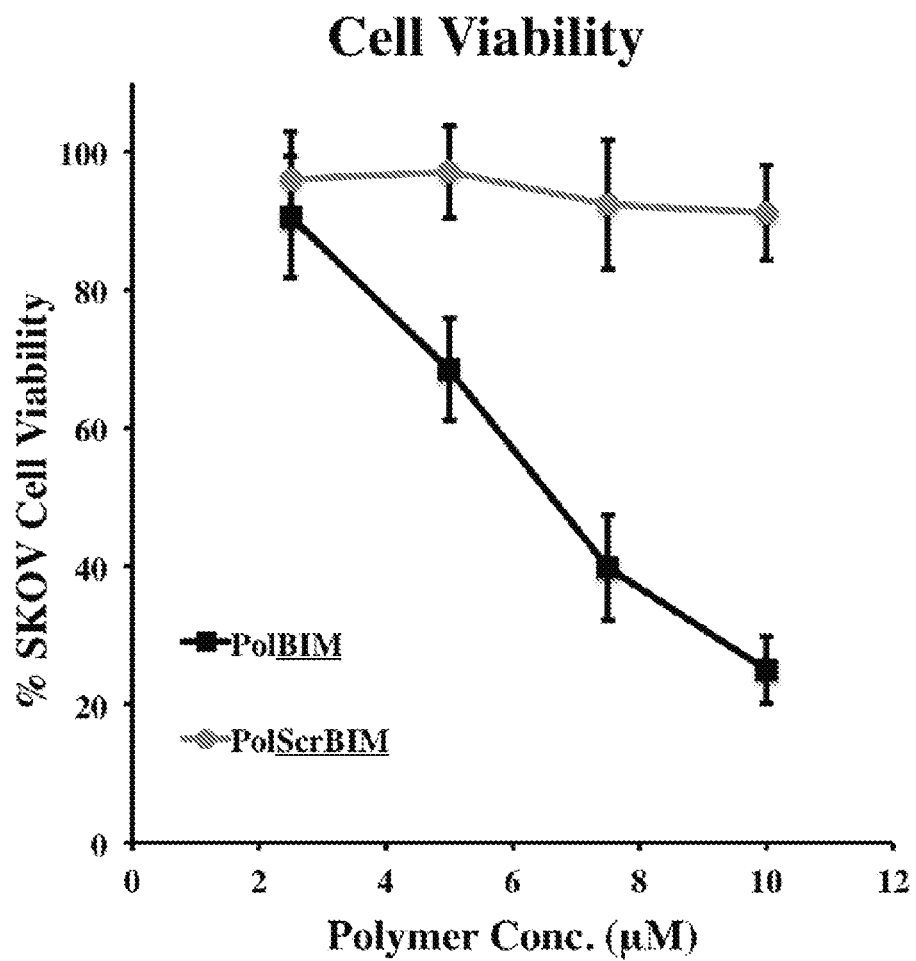
FIG. 15 compares SKOV3 ovarian cancer cell viability for a representative diblock copolymer of the invention (PolBIM) and control (PolScrBIM). PolBIM induces cell death in cultures of SKOV3 ovarian cancer cells. In a dose-responsive manner, PolBIM reduced the viability of SKOV3 cells at 96 hours as measured by MTS assay. In contrast, the PolScrBIM control exhibited negligible cytotoxicity.
Figure 16A:
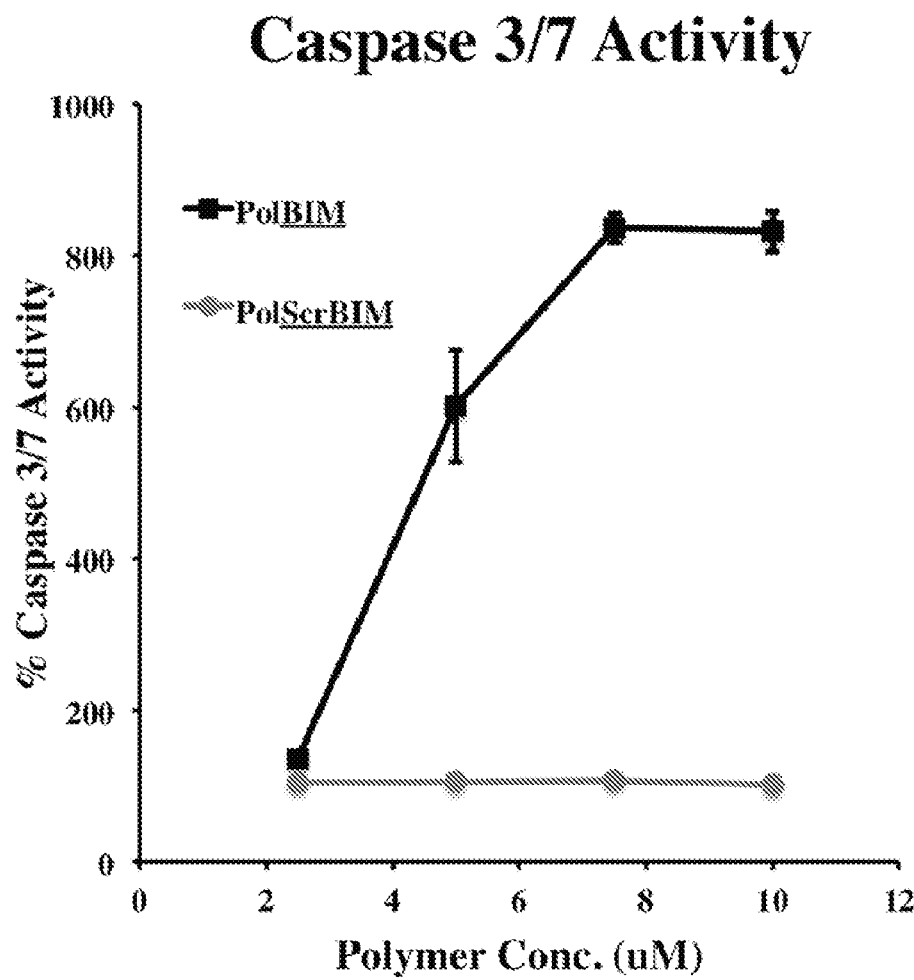
FIGS. 16A and 16B compare expression of apoptotic markers in SKOV3 ovarian cancer cells for a representative diblock copolymer of the invention (PolBIM) and control (PolScrBIM). After 72 hours of polymer treatment, activation of caspase signaling was measured by addition of a pro-fluorescent caspase 3/7 substrate to cell cultures. Percent caspase 3/7 activity is reported relative to untreated cells (16A). After 72 hours of treatment with polymer (10 μM), FITC-annexin V dye was added to SKOV3 cultures and flow cytometry was used to measure percent of cells stained positive (16B).
Figure 16B:
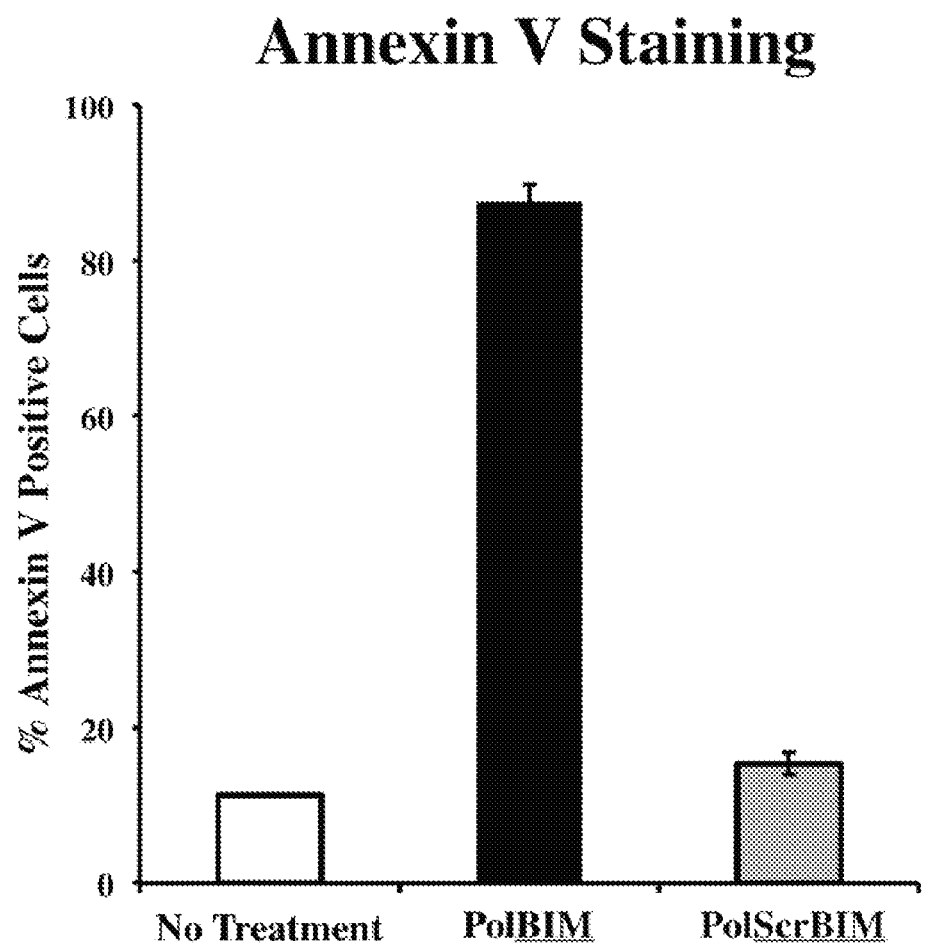
Figure 17E:
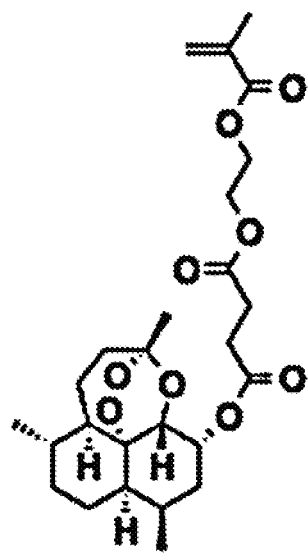
Figure 17F:
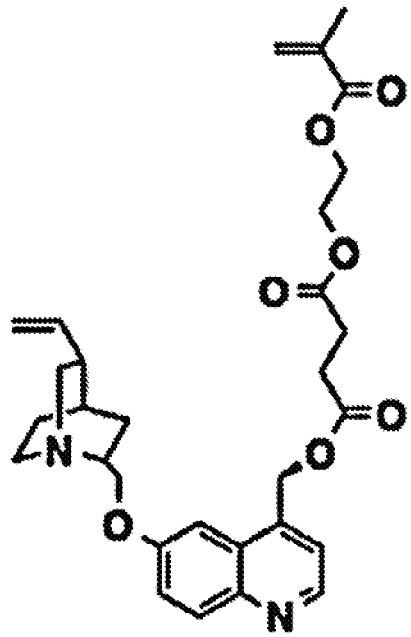
Figure 17G:
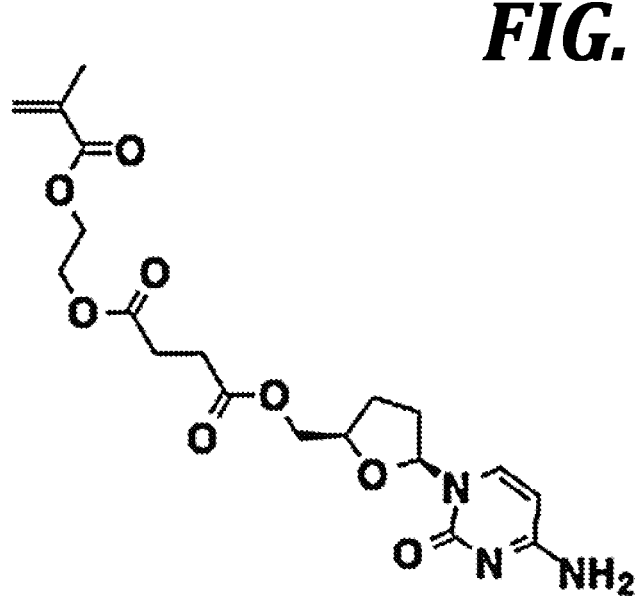

The peptide BIM is poised to make large impact in the field of cancer therapy if it can be effectively delivered into tumor cells. BIM functions by targeting the pro-survival Bcl-2 proteins, whose overexpression impairs apoptosis and plays a role in the development of a wide array of cancers. BIM is unique among Bcl-2 antagonists in it that it binds to and inhibits all six of the cancer-promoting Bcl-2 proteins, potently inducing apoptosis. In the diblock copolymers of the invention, BIM is directly integrated into diblock copolymers through a cathepsin B-cleavable linkage to validate this design for the intracellular delivery of therapeutic peptides. In the reported studies, polymer containing BIM (PolBIM) potently induced cell death in an SKOV3 ovarian cancer cell line, in comparison to a control polymer containing an inactive peptide sequence (PolScrBIM) (FIG. 15). Treatment with PolBIM lead to a corresponding increase in two apoptotic markers, caspase 3/7 activity and PS externalization (annexin V staining), indicating that the mechanism of cell death is BIM-mediated activation of the apoptotic cascade (FIGS. 16A and 16B).

Definitions

Unless otherwise indicated, all numbers expressing quantities of ingredients, properties such as molecular weight, reaction conditions, and so forth are to be understood as being modified in all instances by the term "about." Accordingly, unless indicated to the contrary, the numerical parameters set forth herein are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. When further clarity is required, the term "about" has the meaning reasonably ascribed to it by a person skilled in the art when used in conjunction with a stated numerical value or range (i.e., denoting somewhat more or somewhat less than the stated value or range, to within a range of ±20% of the stated value to ±1% of the stated value, inclusive). Notwithstanding that the numerical ranges and parameters setting forth the scope of the invention are approximations, the numerical values set forth in the specific examples are reported as precisely as possible. Any numerical value, however, inherently contains certain errors necessarily resulting from the standard deviation found in their respective testing measurements.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Unless otherwise defined, all technical and scientific terms used herein have the same meaning as commonly understood by one of ordinary skill in the art.

The terms "a," "an," "the" and similar referents used in the context of describing the invention (especially in the context of the following claims) are to be construed to cover both the singular and the plural, unless otherwise indicated herein or clearly contradicted by context.

Recitation of ranges of values herein is merely intended to serve as a shorthand method of referring individually to each separate value falling within the range. Unless otherwise indicated herein, each individual value is incorporated into the specification as if it were individually recited herein.

The use of any and all examples, or exemplary language (e.g., "such as") provided herein is intended merely to better illuminate the invention and does not pose a limitation on the scope of the invention otherwise claimed.

Unless the context clearly requires otherwise, throughout the description and the claims, the words "comprise," "comprising," and the like are to be construed in an inclusive sense as opposed to an exclusive or exhaustive sense; that is to say, in the sense of "including, but not limited to." Words using the singular or plural number also include the plural and singular number, respectively.

The following examples are provided for the purpose of illustrating, not limiting, the invention.

EXAMPLES

Example 1

The Preparation and Properties of Representative Prodrug Copolymers and Diblock Copolymers: Poly(Ethylene Oxide) Stabilizing Groups In this example, the preparations and properties of representative ciprofloxacin prodrug copolymers and diblock copolymers of the invention are described. These copolymers include poly(ethylene oxide) constitutional units.

Materials.

Chemicals and all materials were supplied by Sigma-Aldrich unless otherwise specified. Sodium trifluoroacetate was purchased from TCI America. Recombinant human butyrylcholinesterase (BChE) was obtained from R&D systems. PEGMA 950 (Aldrich) (30 g) was purified as described in Smith et al., Chem. Sci. 2015, 6, 264. Spectra/Por regenerated cellulose dialysis membranes (6-8 kDA cutoff) were obtained from Fisher Scientific. G-25 prepacked PD10 columns were obtained from GE Life Sciences. MTS cytotoxicity kits were obtained from Promega. Unless otherwise stated, RAW 264.7 cells, murine derived macrophages (ATCC), were maintained in Dulbecco's modified eagle medium (DMEM) containing L-glutamine (Gibco), 4.5 g/L glucose, 10% fetal bovine serum (FBS, Invitrogen), and 1% penicillin-steptomycin (Gibco) at 37° C. and 5% $CO_2$.

Synthesis of (hydroxyethyl)methacrylate-boc-ciprofloxacin (HBC)

Figure 7:
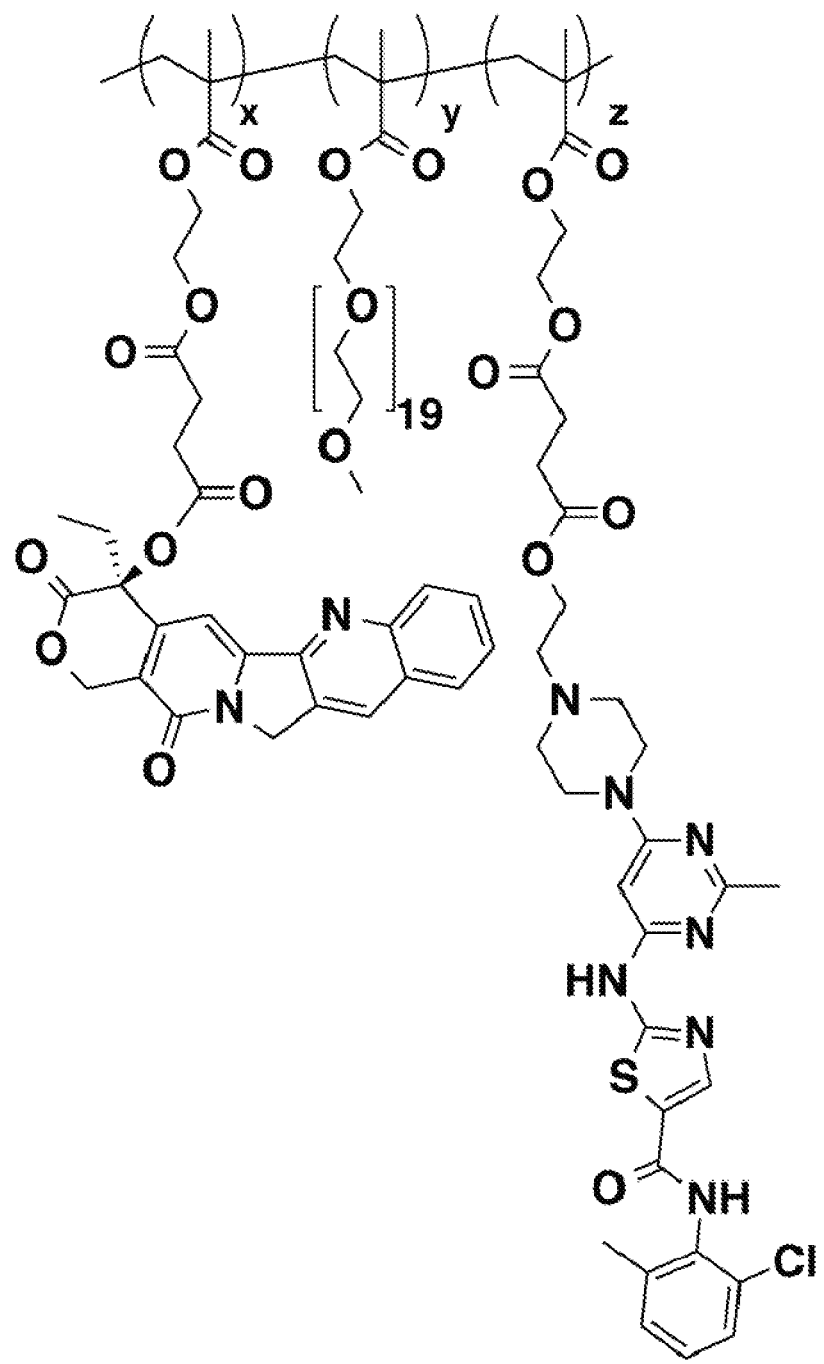
FIG. 7 is a schematic illustration of a representative combined dasatinib/camptothecin prodrug diblock copolymer of the invention, poly(O950-co-CamSMA)-b-(DtSMA).

To 20 g (60 mmol) of ciprofloxacin in 350 mL of dioxane:water (1:1) was added 90 mL of 1N NaOH, followed by 20 g (91.6 mmol) of di-tert-butyl dicarbonate. The reaction mixture was stirred at room temperature for 17 h. The white precipitate obtained was filtered, washed with water and then with acetone. The resulting product, as shown in FIG. 1B, 7-(4-(tert-Butoxycarbonyl)piperazin-1-yl)-1-cyclopropyl-6-fluoro-4-oxo-1,4-dihydroquinoline-3-carboxylic acid (Boc protected Cipro), was dried under high vacuum overnight. Yield=25.14 g (96.5%). $^1$H NMR (300 MHz, CDCl$_3$) δ 1.20 (m, 2H), 1.40 (m, 2H), 1.49 (s, 9H), 3.29 (t, J=5.0 Hz, 4H), 3.54 (m, 1H), 3.67 (t, J=5.0 Hz, 4H), 7.37 (d, J=7.1 Hz, 2H), 7.99 (d, J=12.9 Hz, 1H), 8.73 (s, 1H).

The resulting Boc protected Cipro 10.35 g (24 mmol), N,N,N',N'-tetramethyl-O-(1H-benzotriazol-1-yl)uronium hexafluorophosphate (HBTU) 22.8 g (0.16 mol) and N,N-dimethylpyridin-4-amine (DMAP) 292 mg (2.4 mmol) were taken in 500 mL of CH$_2$Cl$_2$ and cooled to 0° C. N,N-diisopropylethylamine 21 mL (0.12 mol) was added, followed by 2-hydroxylethyl methacrylate 11.7 g (90 mmol). After 10 min at 0° C., the solution was stirred at room temperature for 16 h. The reaction mixture was washed with brine (2×200 mL) and the organic phase was dried over anhydrous sodium sulfate. After evaporation of the solvent, the product HEMA-Boc-Cipro (HBC) was precipitated in ether, and then purified by column chromatography using 5% methanol in chloroform. Yield=10.85 g (83.1%). δ 1.13 (m, 2H), 1.30 (m, 2H), 1.48 (s, 9H), 1.94 (s, 3H), 3.20 (t, J=4.8 Hz, 4H), 3.42 (m, 1H), 3.64 (t, J=4.8 Hz, 4H), 4.50 (m, 4H), 5.58 (s, 1H), 6.15 (s, 1H), 7.29 (d, J=7.0 Hz, 1H), 8.0 (d, J=13.1 Hz, 1H), 8.47 (s, 1H). MS (ESI, m/z): calc. for C$_{28}$H$_{34}$FN$_3$O$_7$ (M): 543.6, found: 544.5 [M+1]$^+$, 566.4 [M+Na]$^+$ and 582.2 [M+K]$^+$.

Synthesis of ciprofloxacin-(phenol)methacrylate (CPM)

Mono-2-(methacryloyloxy)ethyl succinate 9.2 g (50 mmol) dissolved in 150 mL of CH$_2$Cl$_2$ was cooled to 0° C. To this solution, N-hydroxysuccinimide 4.72 g (41 mmol) and N—N'-dicyclohexylcarbodiimide 9.06 g (44 mmol) were added. After 15 min, the ice bath was removed and the reaction mixture was stirred at room temperature for 16 h. The byproduct dicyclohexylurea was filtered off, and the filtrate was concentrated to 40 mL by evaporating the solvent under reduced pressure. This solution containing the activated NHS ester was directly added to 6.15 g (50 mmol) of 4-(aminomethyl)phenol pre-dissolved in 30 mL N,N-dimethylformamide, followed by 13.94 mL (0.1 mol) of triethylamine. After stirring for 6 h at RT, the reaction mixture was diluted with 200 mL of CH$_2$Cl$_2$, and washed with water (2×100 mL). The organic layer was dried over anhydrous sodium sulfate and concentrated under reduced pressure. The thick residue obtained was treated with 100 mL ether, and vigorously stirred for 15 min. Then 75 mL hexane was added, and again stirred well for 10 min. The solvent was carefully decanted and the process was repeated one more time. The product butanoic acid, 4-[(4-hydroxyphenyl)methylamino]-4-oxo-1-(2-methacryloyloxy)ethyl ester (FIG. 1B) obtained was further purified by flash column chromatography using 5% methanol in chloroform. Overall yield for two steps: 10.16 g (76%). $^1$H NMR (300 MHz, CDCl$_3$) δ 1.93 (s, 3H), 2.50 (t, J=6.7 Hz, 2H), 2.72 (t, J=6.7 Hz, 2H), 4.30 (s, 4H), 4.34 (d, J=5.6 Hz, 2H), 5.59 (m, 1H), 6.08 (t, J=5.6 Hz, 1H), 6.12 (s, 1H), 6.30 (s, 1H), 6.75 (d, J=8.5 Hz, 2H), 7.09 (d, J=8.5 Hz, 2H). MS (ESI, m/z): calc. for C$_{17}$H$_{21}$NO$_6$ (M): 335.4, found: 358.8 [M+Na]$^+$ and 693.8 [2M+Na]$^+$.

Boc protected ciprofloxacin (FIG. 1B) 2.15 g (5 mmol) and N,N-dimethylpyridin-4-amine (DMAP) 610 mg (5 mmol) were taken in 250 mL of CH$_2$Cl$_2$ and cooled to 0° C. To this solution, N,N,N',N'-tetramethyl-O-(1H-benzotriazol-1-yl)uronium hexafluorophosphate (HBTU) 4.74 g (12.5 mmol) was added, followed by N,N-diisopropylethylamine 3.5 mL (20 mmol). After 10 min at 0° C., the reaction mixture was stirred at RT for 30 min, and then cooled back to 0° C. The phenolic monomer 1.68 g (5 mmol) was introduced and the reaction was continuously stirred at 0° C. for 20 min, and then at RT for 16 h. The reaction mixture was filtered and the filtrate was washed with water (100 mL) and brine (100 mL). The organic phase was dried over anhydrous sodium sulfate and the solvent was evaporated under reduced pressure. The residue was precipitated in ether, and then purified by column chromatography using 30% tetrahydrofuran in chloroform containing 0.1% triethylamine. Yield=2.45 g (65.4%). $^1$H NMR (300 MHz, CDCl$_3$) δ 1.18 (m, 2H), 1.35 (m, 2H), 1.5 (s, 9H), 1.94 (s, 3H), 2.52 (t, J=6.7 Hz, 2H), 2.73 (t, J=6.7 Hz, 2H), 3.33 (t, J=4.9 Hz, 4H), 3.45 (m, 1H), 3.65 (t, J=4.9 Hz, 4H), 4.32 (s, 4H), 4.44 (d, J=5.7 Hz, 2H), 5.58 (m, 1H), 6.12 (s, 1H), 6.18 (t, J=5.5 Hz, 1H), 7.15 (d, J=8.5, 2H), 7.29 (two doublets merged, 3H), 8.05 (d, J=13.1 Hz, 1H), 8.63 (s, 1H). MS (ESI, m/z): calc. for C$_{39}$H$_{45}$FN$_4$O$_{10}$ (M): 748.8, found: 750.1 [M+1]$^+$ and 771.8 [M+Na]$^+$.

Kinetic Evaluation of HBC.

Kinetic evaluation of HBC was conducted with 4-cyano-4-(phenylcarbonothioylthio)pentanoic acid (CTP) and 4,4'-Azobis(4-cyanovaleric acid) (ABCVA) as the RAFT chain transfer agent and initiator, respectively, in acetic acid at 70° C. The initial monomer to CTA to initiator ([M]$_o$:[CTA]$_o$:[I]$_o$) ratio was 25:1:0.2. In order to understand the influence of the degree of polymerization (DP) on the evolution of molecular weight, RAFT polymerizations of HBC were conducted under similar reaction conditions with [CTA]$_o$:[I]$_o$ ratio of 5:1 and [M]$_o$:[CTA]$_o$ ratios of 12.5, 25, 50, and 100. Individual polymerization solutions were transferred to a septa-sealed vial and purged with nitrogen for 20 minutes. After the allotted time, the polymerization vials were transferred to a preheated water bath at 70° C. and allowed to polymerize for 2.5 h. Following polymerization, the individual vials were quenched by exposure to oxygen by opening the septa seal and immersing the vials in ice. The polymerizations were evaluated for monomer conversion via $^1$H NMR in C$_2$D$_6$OS by comparing the HBC vinyl resonances at δ=6.1 and 5.7 ppm to ester resonances at δ=4.4 and 4.1 ppm.

RAFT Copolymerization of PEGMA 950 (O950) and HBC.

The RAFT copolymerization of poly(O950-co-HBC) was conducted in pyridine with CTP and ABCVA as the CTA and initiator, respectively, with [M]$_o$:[CTA]$_o$ and [CTA]$_o$:[I]$_o$, equal to 25:1 and 10:1. To a 100 mL round-bottom flask was added CTP (112.6 mg, 403 μmol), ABCVA (11.3 mg, 40.3 μmol), HBC (1.25 g, 2.62 mmol), O950 (7.08 g, 7.46 mmol), and pyridine (40.67 g). The solution was then septa sealed and purged with nitrogen for 60 minutes. The round-bottom flask was then transferred to a preheated water bath at 70° C. and allowed to polymerize for 18 hours. The polymerization solution was then precipitated in ether and the resultant polymer was dried in vacuo for 48 h. The final molecular weight and Đ, as measured by GPC, and molar composition of poly(O950-co-HBC) was 13.1 kDa, 1.08, and 72:28 O950:HBC (74:26 feed), respectively. This corresponded to a 16 wt. % Cipro incorporation. Copolymer compositions was determined by both $^1$H NMR and $^{19}$F NMR. Briefly, analysis by $^{19}$F NMR used sodium trifluoroacetate (C$_2$F$_3$NaO$_2$) as an internal standard where 1.5 uL of a 10 mg/mL solution of C$_2$F$_3$NaO$_2$ was added to 1 mL of a 20 mg/mL polymer solution in C$_2$D$_6$OS and molar composition was determined by comparing the three fluorine resonances from the internal standard at δ=−73.4 ppm against the single fluorine resonances from Cipro containing copolymer at δ=−124.5 ppm. Molar compositions were also analyzed by $^1$H NMR in CDCl$_3$ by comparing the HBC (9H) Boc resonances at δ=1.52 ppm to the O950 (3H) methoxy at δ=3.4 ppm. Both methods of drug quantification were in good agreement and resulted in similar drug composition.

RAFT Copolymerization of O950 and CPM.

The RAFT copolymerization of poly(O950-co-CPM) was conducted in THF with CTP and ABCVA as the CTA and initiator respectively with [M]$_o$:[CTA]$_o$, [CTA]$_o$:[I]$_o$, equal to 25:1 and 10:1, similar to the polymerization of poly (O950-co-HBC). To a 25 mL round-bottom flask was added CTP (38.8 mg, 139 μmol), ABCVA (3.89 mg, 13.9 μmol), CPM (1.00 g, 1.34 mmol), O950 (2.03 g, 2.14 mmol), and THF (14.15 g). The solution was then septa sealed and purged with nitrogen for 30 minutes. The round-bottom flask was then transferred to a preheated water bath at 65° C. and allowed to polymerize for 18 hours. The polymerization solution was then precipitated in ether and dried in vacuo for 48 h. The final molecular weight and Đ, as measured by GPC and molar composition of poly(O950-co-CPM) was 11.8 kDa, 1.09, and 64:36 O950:CPM (80:20 feed), respectively (16.7 wt. % Cipro in the final copolymer). Similar to poly(O950-co-HBC), the copolymer composition of poly (O950-co-CPM) was determined by both $^{19}$F NMR and, independently, by $^1$H NMR, as previously described above.

Synthesis of Poly(O950) Via RAFT.

The synthesis of a poly(O950) macroCTA was conducted in DMSO with CTP and ABCVA as the CTA and initiator respectively with [M]$_o$:[CTA]$_o$, [CTA]$_o$:[I]$_o$, equal to 25:1 and 10:1. To a 50 mL round-bottom flask was added CTP (82.34 mg, 2.95 μmol), ABCVA (8.26 mg, 29.5 μmol), O950 (7.00 g, 7.37 mmol), and DMSO (28 g). The solution was then septa sealed and purged with nitrogen for 60 minutes. The round-bottom flask was then transferred to a preheated water bath at 70° C. and allowed to polymerize for 18 hours. The transparent solution was then precipitated in ether six times, solvent decanted, and product collected and dried in vacuo. The resulting polymer had a molecular weight and Đ of 17.5 kDa and 1.12, respectively.

Synthesis of poly(O950)-b-(HBC) and poly(O950)-b-(CPM) via RAFT

The RAFT polymerization of poly(O950)-b-(HBC) from a poly(O950) macroCTA (17.5 Da, 1.12 Đ) was conducted in acetic acid with [M]$_o$:[mCTA]$_o$, [mCTA]$_o$:[I]$_o$ equal to 25:1 and 5:1. To a 25 mL round-bottom flask was added O950 mCTA (644 mg, 36.8 μmol), ABCVA (2.06 mg, 7.36 μmol), HBC (0.5 g, 0.92 mmol), and acetic acid (2.64 g). The solution was then septa sealed and purged with nitrogen for 30 minutes. The round-bottom flask was then transferred to a preheated water bath at 70° C. and allowed to polymerize for 2.5 hours. The solution was then precipitated in ether for six times, solvent decanted, and product collected, dried in vacuo, and lyophilized over 48 h. The final molecular weight, Đ, and composition of poly(O950)-b-(HBC) was 48 kDa and 1.27, respectively, corresponding to DPs for each blocks of 18 and 56 respectively (34 wt. % ciprofloxacin in the final copolymer). Similar to the copolymers, the diblock compositions were determined by both $^1$H NMR and $^{19}$F NMR. Briefly for $^{19}$F NMR analysis, 3 uL of a 10 mg/mL solution of $C_2F_3NaO_2$ was added to 1 mL of 20 mg/mL diblock polymer solution in $C_2D_6OS$ and molar composition was determined again by comparing the three fluorine resonances from the internal standard at δ=−73.4 ppm against the single fluorine resonances from Cipro diblock polymer at δ=−124.5 ppm. In addition, $^1$H NMR in CDCl$_3$ was used to again compare the HBC (9H) Boc resonances at δ=1.52 ppm to the O950 (3H) methoxy at δ=3.4 ppm. Analogous to the copolymers, values obtained from $^{19}$F NMR are being reported for both diblocks.

The RAFT polymerization of poly(O950)-b-(CPM) utilized the same O950 mCTA homopolymer (Mn=17.5 kDa, Đ=1.12) as the one used in the synthetic strategy for the polymerization of poly(O950)-b-(HBC), as noted above. This reaction was conducted in THF with [M]$_o$:[mCTA]$_o$, [mCTA]$_o$:[I]$_o$ equal to 25:1 and 10:1. To a 10 mL round-bottom flask was added O950 mCTA (455 mg, 26.7 μmol), ABCVA (0.75 mg, 2.67 μmol), CPM (0.5 g, 0.67 mmol), and THF (2.55 g). The solution was then septa sealed and purged with nitrogen for 30 minutes. The round-bottom flask was then transferred to a preheated water bath at 65° C. and allowed to polymerize for 18 hours. The final copolymer was subsequently isolated as detailed above. The final molecular weight, Đ, and composition of poly(O950)-b-(CPM) was 41.8 kDa and 1.35, respectively, corresponding to DPs for each blocks of 18 and 32 respectively (30 wt. % Cipro in the final copolymer).

Deprotection and Purification of Copolymer and Diblock Systems.

Post polymerization removal of the Boc protecting groups, present on HBC and CPM residues, was conducted in neat trifluoroacetic acid (TFA) and 1:1 CHCl$_3$:TFA, respectively at a polymer concentration of 50 mg/mL. The reaction was allowed to proceed at 25° C. for 2h after which time the solution was precipitated in ether. The product was collected and dried in vacuo for 48 h. In order to remove any TFA salts attached to the secondary amine group on Cipro after deprotection and precipitation, the polymers were redisolved in molecular grade water and dialyzed against first 250 mM and then 10 mM NaH$_2$PO$_4$ at pH 7.4 with repeated buffer changes (2-3×) over two days. The polymers were then frozen and lyophilized before further purification via PD-10 desalting column (GE Life Sciences) followed by lyophilization for an additional 48 h.

Gel Permeation Chromatography (GPC).

Absolute molecular weights and polydisperity indices were determined using Tosoh SEC TSK-GEL α-3000 and α-e4000 columns (Tosoh Bioscience, Montgomeryville, Pa.) connected in series to an Agilent 1200 Series Liquid Chromatography System (Santa Clara, Calif.) and Wyatt Technology miniDAWN TREOS, 3 angle MALS light scattering instrument and Optilab TrEX, refractive index detector (Santa Barbara, Calif.). HPLC-grade DMF containing 0.1 wt. % LiBr at 60° C. was used as the mobile phase at a flow rate of 1 ml/min.

Characterization of Copolymer and Diblock Micelles.

Dynamic light scattering (DLS) studies of the block copolymers were conducted using a Malvern Instruments Zetasizer Nano series instrument equipped with a 22 mW He—Ne laser operating at 632.8 nm. Solutions of the copolymer and diblock were prepared in the pH range capturing the endosomal trafficking pathway (7.4, 7.0, 6.6, 6.2, 5.8, 5.2, and 4.6) with either 100 mM sodium phosphate or acetate buffer with 150 mM NaCl at a polymer concentration of 0.5 mg/mL. The resulting solutions were filtered with 0.22 μm filters prior to measurement, and mean diameter was defined as the ±half peak width. All measurements were performed in triplicate comparing the copolymers to the diblocks. The polymer micelles were analysed for zeta potential, using a ZetaPALS detector, at 1 mg/mL polymer concentration as a function of pH (7.4, 7.0, 6.6, 6.2, 5.8, and 5.2) with either 10 mM sodium phosphate or acetate buffer.

Analysis of Cipro by High-Performance Liquid Chromatography (HPLC).

The HPLC analysis of Cipro was carried out with an Agilent 1260 Quaternary HPLC Pump, Agilent 1260 Infinity Standard Automatic Sampler, Agilent 1260 Infinity Programmable Absorbance Detector, and Agilent ChemStation software for LC system (Palo Alto, Calif.). Both ciprofloxacin hydrochloride and liquid Sera Human from AB blood donor were purchased and used as received. The analyte was separated at ambient temperature using a Zorbax RX-$C_{18}$ (4.6×150 mm; 5 µm) analytical column (Agilent Technologies, CA).

The UV detector was operated at 277 nm, and the mobile phase consisted of 2% aqueous acetic acid and acetonitrile (84:16) v/v. The flow rate was set at 1.0 mL/min and sample injection volume at 20 µL. A stock solution of Cipro was prepared in deionized water at 10 mg/mL. Working solutions of Cipro for standard curves were diluted from stock solution using the mobile phase to the listed concentrations of 200 µg/mL, 100 µg/mL, 50 µg/mL, 25 µg/mL, 12.5 µg/mL, 6.25 µg/mL, 3.12 µg/mL, and 1.56 µg/mL.

Each listed solution above was diluted with a 1:1 v/v ratio of either mobile phase:deionized water or mobile phase: human serum to create a final Cipro standards of 100 µg/mL, 50 µg/mL, 25 µg/mL, 12.5 µg/mL, 6.25 µg/mL, 3.12 µg/mL, 1.56 µg/mL, and 0.78 µg/mL for pharmaceutical and biological analysis, respectively. Both non-serum (mobile phase:deionized water) and serum standards were subsequently treated with 50% acetonitrile (v/v) to promote protein precipitation. Serum standards were centrifuged at 12,000 g for 15 minutes and supernatants were collected and filtered using a 0.45 µm low protein binding filter before HPLC analysis. Non-serum standards were analysed without the need for centrifugation. All standards were processed using a gradient HPLC elution profile, where the mobile phase transitioned to 100% acetonitrile over 15 minutes, followed by 10 minutes of column washing with acetonitrile and water and 5 minutes of equilibration with mobile phase.

Drug Release from Polymeric Prodrugs.

The drug release from polymer conjugates was carried out in serum at 37° C. at a polymer concentration of 6 mg/mL. Sample time points were collected on a regular basis. Quantification of total Cipro in the polymer conjugates was measured by taking 6 mg/mL of polymer and dissolving it in 10% aq. $H_2SO_4$ for 48 h at 25° C., denoted by Peak ($H_2SO_4$). The HPLC with a gradient elution profile was used to quantify amount of drug released using the same instrument parameters set forth for drug standards. A 1:1 dilution of serum sample to 2% aqueous acetic acid and acetonitrile (84:16) v/v was conducted, followed by another 1:1 dilution with acetonitrile. The resulting samples were vortexed and centrifuged at 12,000 g for 15 minutes. Supernatants were collected and filtered using a 0.45 nm low protein binding filter before running on the HPLC. Percent (%) drug released was subsequently quantified using the formula: % Drug Released=[Peak($t_x$)−Peak($t_0$)]/[Peak($H_2SO_4$)], where $t_x$ and $t_0$ are the peaks resolved by the HPLC at time x and zero, respectively.

In Vitro Cytotoxicity Measurements.

The cytotoxicity of the prodrug copolymers and diblock copolymers were evaluated in RAW 264.7 cells using the CellTiter 96AQueous One Solution Cell Proliferation Assay (MTS) (Promega Corp., Madison, Wis.). RAW cells were seeded in DMEM (Gibco, Life Technologies, Grand Island, N.Y.) containing 1% pen/strep and 10% fetal bovine serum (FBS) at a density of 50,000 cells/well in 96-well plates and allowed to adhere for 18 h at 37° C. with 5% $CO_2$. After incubation, polymers diluted in supplemented DMEM at a concentration of 40 mg/mL total polymer were added to cells in triplicate wells in a 1:1 dilution, then serially diluted down the plate (20 mg/mL-9.77 µg/mL), and cells were incubated for 24 hours. After the allotted time, cells were evaluated using the CellTiter MTS assay according to the manufacturer's instructions. The absorbance at 490 nm was evaluated using a Tecan Safire 2 microplate reader. MTS reagent alone was used as a negative control and all treatments were compared to untreated cells as a positive control to acquire percentage viability. All experiments were carried out in triplicate wells on duplicate days.

In Vitro Co-Culture Activity Using a *B. thailandensis* Infection Model.

To evaluate the in vitro efficacy of the polymer systems, RAW 264.7 murine macrophage cells were seeded into 48 well plates at a density of 500,000 cells/mL in 250 µL of antibiotic free DMEM (Gibco)+10% FBS and allowed to adhere for 18 h at 37° C. with 5% $CO_2$. After 18 hours, RAW cells were infected with *Burkholderia thailandensis* (E264) at early log phase ($OD_{600}$=0.2) at a MOI of 5, and incubated for 1 hour. Growth media was then replaced with fresh DMEM containing 10% FBS and 250 µg/mL kanamycin to remove extracellular bacteria and cells were incubated for another hour. Media was then replaced with unsupplemented DMEM containing varying concentrations of HBC copolymer (20-3000 µg/mL), CPM copolymer (1-2000 µg/mL), or free drug (0.01-100 µg/mL) into triplicate wells per treatment. Cells were incubated an additional 22 hours. After incubation, cell media was aspirated, cells were washed three times with 1×PBS, and lysed with 100 µL of PBS+ 0.1% Triton X-100 (Sigma Aldrich, St. Louis, Mo.). Lysates were pooled by treatment, serially diluted, and plated onto triplicate LB agar plates at multiple 10× dilutions, and incubated for 24 hours. After 24 hours colony forming units (CFU) were counted. Data represented as CFU/well vs. Cipro dose. All experiments were repeated on duplicate days.

Conclusions

Methacrylate-based prodrug monomers were synthesized from the antibiotic Cipro and then incorporated into copolymers and diblock copolymers using RAFT polymerization. Linear pseudo first order kinetics were observed for the homopolymerization of HBC and both monomers showed narrow and symmetric molecular weight distributions over a range of target DPs between 12 and 100. Prodrug monomers were then either copolymerized with polyethyleneglycol methacrylate (O950) to yield hydrophilic copolymers or chain extend from poly(O950) macroCTAs to yield diblock copolymers. The resultant copolymers and diblock copolymers contained 16 and 34% drug respectively. DLS and zeta potential measurements were employed to evaluate the pH-dependent aqueous solution properties of these constructs. At physiological pH values the diblock copolymer constructs yielded hydrodynamic diameters that are consistent with micelles, which disassembled upon a reduction in the solution pH to 6.6. In contrast, the copolymers formed molecular dissolved unimers with particle sizes that were largely independent of the solution pH. Moreover, copolymers containing Cipro linked via phenolic esters showed faster hydrolysis rates with 50% drug released at 120 h, whereas copolymers with the corresponding aliphatic ester linkages showed similar percent drug release over 22 d. Diblock copolymers with a discrete Cipro block showed greatly reduced hydrolysis rates for both ester linked drugs.

In addition, in vitro toxicity measurements in RAW 264.7 cells showed the copolymers to be nontoxic up to 20 mg/mL following a 24h incubation period. Co-culture efficacy was determined using *Burkholderia thailandensis* where an MIC of 6.0 and 0.6 mM of polymerized antibiotic were determined for the aliphatic ester and phenyl ester linked polymeric prodrugs respectively. In conclusion, polymer architecture and drug linkage chemistry can influence drug release kinetics and be tuned to yield a richly controllable delivery system.

Example 2

The Preparation and Properties of Representative Prodrug Copolymers and Diblock Copolymers: Poly(Ethylene Oxide) and Ampholyte Stabilizing Groups In this example, the preparations and properties of representative chemotherapeutic prodrug copolymers and diblock copolymers of the invention are described. As described below, in certain embodiments, these copolymers include poly(ethylene glycol) constitutional units (poly(Cam-SMA-co-O950) and poly(Dt-SMAcoO950)), and in other embodiments, these copolymers include ampholyte constitutional units (poly[(MA-co-DMAEMA)-b-(Dt-SMA)]).

Polymeric prodrugs were prepared from the chemotherapeutic agents camptothecin and dasatinib via the direct RAFT polymerization of polymerizable prodrug monomers without the need for post-polymerization conjugation reactions. The covalently linked drugs were dispersed within hydrophilic polyethylene glycol methacrylate brushes or homopolymerized from a hydrophilic macroCTA to form a discrete polydrug segment. In all cases the copolymers were shown to have narrow molecular weight distributions and compositions determined by initial monomer stoichiometry. The ester-linked prodrugs were shown to be release from the macromolecular scaffolds in human serum with rates dependent on both the physiochemical nature of the drug as well as the overall polymer morphology. Self-assembly of the diblock copolymers with a hydrophobic polydrug core was shown to significantly reduce drug release rate but also allowed for high drug loading densities. Live animal imaging in PC-3 (human prostate cancer cell line) tumor xenographs showed that the fluorescently labeled copolymer brushes were trafficked to the tumor 24 hours post injection. Ex vivo analysis of the harvested tissues showed that polymer accumulated preferentially in the tumor and kidneys. In vitro cytotoxicity measurements conducted in K562-S and K562-R cells demonstrated ability of the macromolecular conjugates to release the covalently linked drugs in an active form.

Materials.

Chemicals and all materials were supplied by Sigma-Aldrich unless otherwise specified. 4-Methacryloxyethyl trimellitic anhydride (TMA) was purchased from polysciences. Camptothecin and dasatinib were purchased from VWR. Spectra/Por regenerated cellulose dialysis membranes (6-8 kDA cutoff) where obtained from Fisher Scientific. G-25 prepacked PD10 columns were obtained from GE Life Sciences. MTS cytotoxicity kits were obtained from Promega. Alexa Fluor 647 cadaverine, disodium salt was purchased from ThermoFisher. Tertiary butyl methacrylate (tBMA) was passed through a short plug of aluminum oxide (activated basic) to remove the inhibitor. Dimethylaminoethyl methacrylate (DMAEMA) was distilled under reduced pressure. 4-Cyano-4-(thiobenzoylthio)pentanoic acid (CTP) was obtained from Strem Chemicals Inc. V40 and ABCVA were obtained from VWR and used as received.

Synthesis of N-(2-Chloro-6-methylphenyl)-2-[[6-[4-(2-methacryloxyethylsuccinylethyl)-1-piperazinyl)]-2-methyl-4-pyrimidinyl]amino)]-1,3-thiazole-5-carboxamide (Dt-SMA)

To a mixture of 2-(methacryloxyethyl) monosuccinate 920 mg (4 mmol) and N,N,N',N'-tetramethyl-O-(1H-benzotriazol-1-yl)uronium hexafluorophosphate (HBTU) 1.9 g (5 mmol) in 25 mL of anhydrous DMF was added N,N-diisopropylethylamine 1.4 mL (8 mmol) at 0° C. After 10 min. at 0° C., the solution was stirred at room temperature for 20 min. N-(2-Chloro-6-methylphenyl)-2-[[6-[4-(2-hydroxyethyl)-1-piperazinyl)]-2-methyl-4-pyrimidinyl] amino)]-1,3-thiazole-5-carboxamide 976 mg (2 mmol) was then introduced as solid, and stirring was continued at room temperature for 6 h. The reaction mixture was poured into ice cold water and stirred for 20 min. The off-white solid obtained was filtered, washed with water and dried under high vacuum. The crude ester was dissolved in 15 mL of 15% methanol in chloroform and purified by column chromatography using 10% methanol in chloroform containing 1% of 30% aqueous ammonia. Yield=990 mg (70.7%). $^1$H NMR (300 MHz, DMSO-$d_6$) δ 11.46 (s, 1H, H14), 9.87 (s, 1H, H16), 8.20 (s, 1H, H13), 7.38 (d, J=6.2 Hz, 1H, H20), 7.31-7.18 (m, 2H, H18 & H19), 6.08-5.97 (m, 2H, H2 & H15), 5.58 (s, 1H, H1), 4.27 (s, 4H, H4 & H5), 4.13 (t, J=5.7 Hz, 2H, H8), 3.49 (s, 4H, H11), 2.63-2.52 (m, 6H, H9 & H10), 2.48 (m, 4H, H6 & H7 merged with DMSO peak), 2.39 (s, 3H, H12), 2.22 (s, 3H, H17), 1.85 (s, 3H, H3). MS (ESI) m/z=701.0 (M+1).

Synthesis of (4S)-4-ethyl-3,4,12,14-tetrahydro-3,14-dioxo-1h-pyrano [3',4':6,7]indolizino[1,2-b]quinolin-4-yl ester (Cam-SMA)

To a 100 mL round bottom flask was added camptothecin (0.747 g, mmol), SMA (2.47 g, 10.73 mmol), DMAP (1.31 g, 10.73 mmol), and 74.7 mL anhydrous DMSO. After the reagents were dissolved with light sonication DCC (2.21 g, 10.73 mmol) was added. The solution was then allowed to react in the dark for 24 hours. After this time the solution was filtered through a plug of cotton and then precipitated in 1000 mL of 150 mM HEPES buffer pH 8.4 that had been precooled to 5° C. The precipitated was then filtered, washed with deionized water, and then dissolved in warm acetone. This solution was then filtered through a plug of cotton and then precipitated in petroleum ether. The precipitate was then dried under high vacuum for 24 hours. $^1$H NMR $^1$H NMR (499 MHz, DMSO-$d_6$) δ 0.9 (t, 3H $CH_3CH_2$), 1.8 (s, 3H $CCH_3CO$), 2.1 (Q, 2H, $CH_3CH_2$), 2.6 (m, 4H, $COCH_2CH_2CO$), 4.1-4.4 (m, 4H, $OCH_2CH_2O$), 5.2 (s, 2H, $NCH_2C$), 5.5 (s, 2H, $OCH_2C$), 5.6 (s, 1H, $CHHC(CH_3)CO$), 5.9 (s, 1H, $CHHC(CH_3)CO$), 7.1 (s, 1H, CCHCN), 7.8 (m, 1H, NCCHCHCHCO), 7.9 (m, 1H, NCCHCHCH), 8.1 (m, 2H, NCCHCHCHCHC), 8.7 (s, 2H, $CONCH_2CCHC$).

Synthesis of poly(Cam-SMA-co-O950)

Copolymerization of Cam-SMA and O950 was conducted in DMSO at 70° C. for 18 h in the presence of CTP and ABCVA. The initial molar feed percentages of the Cam-SMA and O950 monomers were both 50%. The $[M]_o$:$[CTA]_o$:$[I]_o$ was 25:1:0.1 at an initial monomer concentration of 20 wt. %. To a 10 mL round bottom flask was added Cam-SMA (0.433 g, 0.772 mmol), O950 (0.733 g, 0.772 mmol), CTP (17.2 mg, 0.062 mmol), ABCVA (1.73 mg, 0.0062 mmol), and DMSO (4.66 mL). The round bottom flask was then sealed with a rubber septa and purged with nitrogen for 1 hour. After this time the polymerization solution was transferred to a preheated water bath at 70° C. and allowed to react for 18 hours. After this time the solution was precipitated into a 50 times excess of diethyl ether. The precipitate was then redissolved in minimal acetone and then precipitated once more into diethyl ether. This process was repeated five additional times after which the copolymer was dried under high vacuum for 48 hours. The dry polymer was then further purified via Sephadex PD10 column according to the manufacturer's instructions. The final copolymer was subsequently isolated by lyophilization. Copolymer composition was determined to be 53% O950 and 47% Cam-SMA by integrating the combined ester resonances between 3.7 and 4.5 ppm (4H Cam-SMA+2H O950) (X) to the Cam-SMA resonances between 4.7 and 5.7 ppm (4H Cam-SMA) (Y) using the equation $^1$H Cam-SMA=Y/4 and $^1$H O950=(X−Y)/2. SEC analysis yielded an $M_n$ and Đ of 26 500 and 1.16, respectively.

Synthesis of poly(Dt-SMA-co-O950)

Copolymerization of Dt-SMA and O950 was conducted in DMSO at 70° C. for 18 h in the presence of CTP and ABCVA. The initial molar feed percentages of the Dt-SMA and O950 monomers were both 50%. The $[M]_o:[CTA]_o:[I]_o$ was 25:1:0.1 at an initial monomer concentration of 20 wt. %. To a 10 mL round bottom flask was added Dt-SMA (0.300 g, 0.428 mmol), O950 (0.407 g, 0.428 mmol), CTP (9.58 mg, 0.034 mmol), ABCVA (0.96 mg, 0.0034 mmol), and DMSO (2.83 mL). The round bottom flask was then sealed with a rubber septa and purged with nitrogen for 1 hour. After this time the polymerization solution was transferred to a preheated water bath at 70° C. and allowed to react for 18 hours. After this time the solution was precipitated into a 50 times excess of diethyl ether. The precipitate was then redissolved in minimal acetone and then precipitated once more into diethyl ether. This process was repeated five additional times after which the copolymer was dried under high vacuum for 48 hours. The dry polymer was then further purified via Sephadex PD10 column according to the manufacturer's instructions. The final copolymer was subsequently isolated by lyophilization. Copolymer composition was determined to be 46% O950 and 54% Dt-SMA by integrating the combined resonances between 3.7 and 4.5 ppm (6H Dt-SMA+2H O950) (X) to the Dt-SMA resonance between 5.9 and 6.1 ppm (1H Dt-SMA) (Y) using the equation $^1$H Dt-SMA=Y and $^1$H O950=(X−6Y)/2. SEC analysis yielded an $M_n$ and Đ of 28 000 and 1.10 respectively.

Synthesis of poly(Cam-SMA-co-Dt-SMA-co-O950)

Copolymerization of Dt-SMA, Cam-SMA, and O950 was conducted in DMSO at 70° C. for 18 h in the presence of CTP and ABCVA. The initial molar feed percentages of Cam-SMA, Dt-SMA and O950 were 25, 25 and 50 mol % respectively. The $[M]_o:[CTA]_o:[I]_o$ was 25:1:0.2 at an initial monomer concentration of 20 wt. %. To a 10 mL round bottom flask was added Cam-SMA (0.120 g, 0.214 mmol), Dt-SMA (0.150 g, 0.214 mmol), O950 (0.407 g, 0.428 mmol), CTP (9.57 mg, 0.034 mmol), ABCVA (1.92 mg, 0.0069 mmol), and DMSO (2.71 mL). The round bottom flask was then sealed with a rubber septa and purged with nitrogen for 1 hour. After this time the polymerization solution was transferred to a preheated water bath at 70° C. and allowed to react for 18 hours. After this time the solution was precipitated into a 50 times excess of diethyl ether. The precipitate was then redissolved in minimal acetone and then precipitated once more into diethyl ether. This process was repeated five additional times after which the copolymer was dried under high vacuum for 48 hours. The dry polymer was then further purified via Sephadex PD10 column according to the manufacturer's instructions. The final copolymer was subsequently isolated by lyophilization. Copolymer composition was determined to be 49 mol % O950, 24 mol % Cam-SMA, and 27 mol % Dt-SMA respectively by integrating the combined resonances ester between 3.8 and 4.5 ppm (4H Cam-SMA, 2H O950, 6H Dt-SMA) (X), the Dt-SMA resonances 5.9 between 6.1 ppm (1H Dt-SMA) (Y), and the Cam-SMA resonances between 4.7 and 5.7 ppm (4H Cam-SMA) (Z) using the equation: $^1$H Dt-SMA=X, $^1$H Cam-SMA=Z/4 and $^1$H O950=(Y−X*6−Y)/2. SEC analysis yielded an $M_n$ and Đ of 29 000 and 1.19, respectively.

Synthesis of poly(tBMA-co-DMAEMA)

The copolymerization of tBMA and DMAEMA was conducted in dioxane at 90° C. for 5 h in the presence of ECT and V40 as the RAFT agent and radical initiator respectively with an equimolar initial molar feed ratio of tBMA and DMAEMA. The $[M]_o:[CTA]_o:[I]_o$ was 60:1:0.05 at an initial monomer concentration of 50 wt. %. To a 100 mL round bottom flask was added DMAEMA (20 g, 0.127 mol), tBMA (18.09 g, 0.127 mol), ECT (1.11 g, 4.22 mmol), V40 (51.6 mg, 0.211 mmol), and dioxane (38 mL). The round bottom flask was then sealed with a rubber septa and purged with nitrogen for 1 hour. After this time the polymerization solution was transferred to a preheated water bath at 90° C. and allowed to react for 5 hours. After this time the solution transferred to a spectrapor regenerated cellulose dialysis membrane (6-8 kDa cutoff) and dialyzed against acetone at 5° C. After three changes of the acetone the copolymer was then furthered dialyzed against water at which point it precipitated. The resultant precipitate was collected and lyophilized under high vacuum. Copolymer composition was determined by comparing the combined backbone region to the DMAEMA ester resonance.

Synthesis of poly[(MA-co-DMAEMA)-b-(Dt-SMA)]

Polymerization of Dt-SMA from a poly(tBMA-co-DMAEMA) macroCTA was conducted in DMSO at 70° C. for 18 hours. The $[M]_o:[CTA]_o:[I]_o$ was 12.5:1:0.02 at an initial monomer concentration of 20 wt. %. To a 5 mL round bottom flask was added Dt-SMA (0.380 g, 0.542 mmol), poly(tBMA-co-DMAEMA) macroCTA (0.260 g, 0.0434 mmol) ABCVA (2.43 mg, 0.0087 mmol), and DMSO (1.78 mL). The round bottom flask was then sealed with a rubber septa and purged with nitrogen for 30 minutes. After this time the polymerization solution was transferred to a preheated water bath at 70° C. and allowed to react for 18 hours. After this time the solution was precipitated into a 20 times excess of diethyl ether from DMSO (×5). The tertiary butyl ester groups were subsequently removed by dissolving the polymer in neat TFA at a concentration of 5 wt % for 8 hours. The polymer was then isolated by precipitation into ether followed by neutralization by dialysis against PBS (0.20 M) at 5° C. followed by water. The diblock copolymer was then further purified using a PD10 desalting column according to the manufacturer's instructions.

Cell Culture and Cytotoxicity Measurements.

K562-S(Imatinib sensitive cells) and K562-R1 (Imatinib resistant cells) cells were cultured in RPMI 1640 (Gibco) supplemented with 10% fetal bovine serum (FBS), 100 U/ml penicillin, and 100 μg/ml streptomycin (Gibco) in a 37° C., 5% $CO_2$ incubator. Free drugs and campothecin/dasatinib polymers were preincubated with culture media containing 10% FBS for 0 day, 1 day, 3 days, and 5 days at a 37° C., 5% $CO_2$ incubator before cell seeding. K562-S and K562-R1 cells were suspended with culture media containing 10% FBS and $5\times10^3$ cells/well were seeded and treated with increasing concentrations of the preincubated drugs in a 96-well plate (Costar). After 3 days or 6 days, for measuring the results of cell viability, the MTS reagent (Promega) was added in a final concentration of 317 μg/ml in the assay wells. After incubation for 1 hr, the absorbance at 490 nm was measured by a 96-well plate reader. The cell viability of treated cells were determined upon normalizing to the cell viability of non-treatment.

GPC Chromatography.

Absolute molecular weights and molar mass dispersities were determined using Tosoh SEC TSK-GEL α-3000 and α-e4000 columns (Tosoh Bioscience, Montgomeryville, Pa.) connected in series to an Agilent 1200 Series Liquid Chromatography System (Santa Clara, Calif.) and Wyatt Technology miniDAWN TREOS, 3 angle MALS light scattering instrument and Optilab TrEX, refractive index detector (Santa Barbara, Calif.). HPLC-grade DMF containing 0.1 wt. % LiBr at 60° C. was used as the mobile phase at a flow rate of 1 mL/min.

Analysis of Drug Release by High-Performance Liquid Chromatography.

The HPLC analysis of drug release was carried out with an Agilent 1260 Quaternary HPLC Pump, Agilent 1260 Infinity Standard Automatic Sampler, Agilent 1260 Infinity Programmable Absorbance Detector, and Agilent ChemStation software for LC system (Palo Alto, Calif.). Dasatinib, camptothecin, and liquid human serum from AB blood donor were used as received. The analyte was separated at ambient temperature using a Zorbax RX-$C_{18}$ (4.6×150 mm; 5 μm) analytical column (Agilent Technologies, CA).

Analysis of dasatinib was conducted at 325 nm with a mobile phase consisting of 2% aqueous acetic acid and acetonitrile (84:16) v/v. The flow rate was set at 1.0 mL/min and sample injection volume at 20 μL. A stock solution of dasatinib was prepared in deionized water at 10 mg/mL. Working solutions of dasatinib for standard curves were diluted from stock solution using the mobile phase to the listed concentrations of 300 μg/mL, 200 μg/mL, 100 μg/mL, 50 μg/mL, 25 μg/mL, 12.5 μg/mL, 6.25 μg/mL, and 3.12 μg/mL. These solutions were then diluted with a 1:1 v/v ratio of either mobile phase:deionized water or mobile phase: human serum to create final dasatinib standards of 150 μg/mL, 100 μg/mL, 50 μg/mL, 25 μg/mL, 12.5 μg/mL, 6.25 μg/mL, and 3.12 μg/mL for pharmaceutical and biological analysis, respectively. Both non-serum (mobile phase:deionized water) and serum standards were subsequently treated with 50% acetonitrile (v/v) to promote protein precipitation. Serum standards were centrifuged at 12,000 g for 15 minutes and supernatants were collected and filtered using a 0.45 μm low protein-binding filter before running on the HPLC. Non-serum standards were run without the need for centrifugation. All standards were processed using a gradient HPLC elution profile for 15 minutes followed by 10 minutes of column washing with acetonitrile and water and 5 minutes of equilibration with mobile phase.

Camptothecin release from polymer conjugates was carried out in serum and buffer (150 mM pH 7.4 sodium phosphate, 150 mM pH 5.8 sodium acetate) at 37° C. at a polymer concentration of 6 mg/mL. Quantification of total Camptothecin in polymer conjugates was measured by taking 6 mg/mL of polymer in 10% aq. $H_2SO_4$ for 72 h at 25° C. The HPLC with a gradient elution profile was used to quantify amount of drug released using the same instrument parameters set forth for drug standards. A 1:1 dilution of serum or buffer samples with methanol:water (75:25) v/v was conducted, followed by another 1:1 dilution with acetonitrile. The resulting samples were vortexed and centrifuged at 12,000 g for 15 minutes. Supernatants were collected and filtered using a 0.45 μm low protein binding filter before HPLC analysis at 370 nm. Percent (%) drug released was subsequently quantified using the formula: % Drug Released=$[Peak(t_x)-Peak(t_0)]/[Peak(H_2SO_4)]$, where $t_x$ and $t_0$ are the peaks resolved by the HPLC at time x and zero, respectively, and Peak($H_2SO_4$) denotes total drug present in the polymer system.

Example 3

Figure 8:
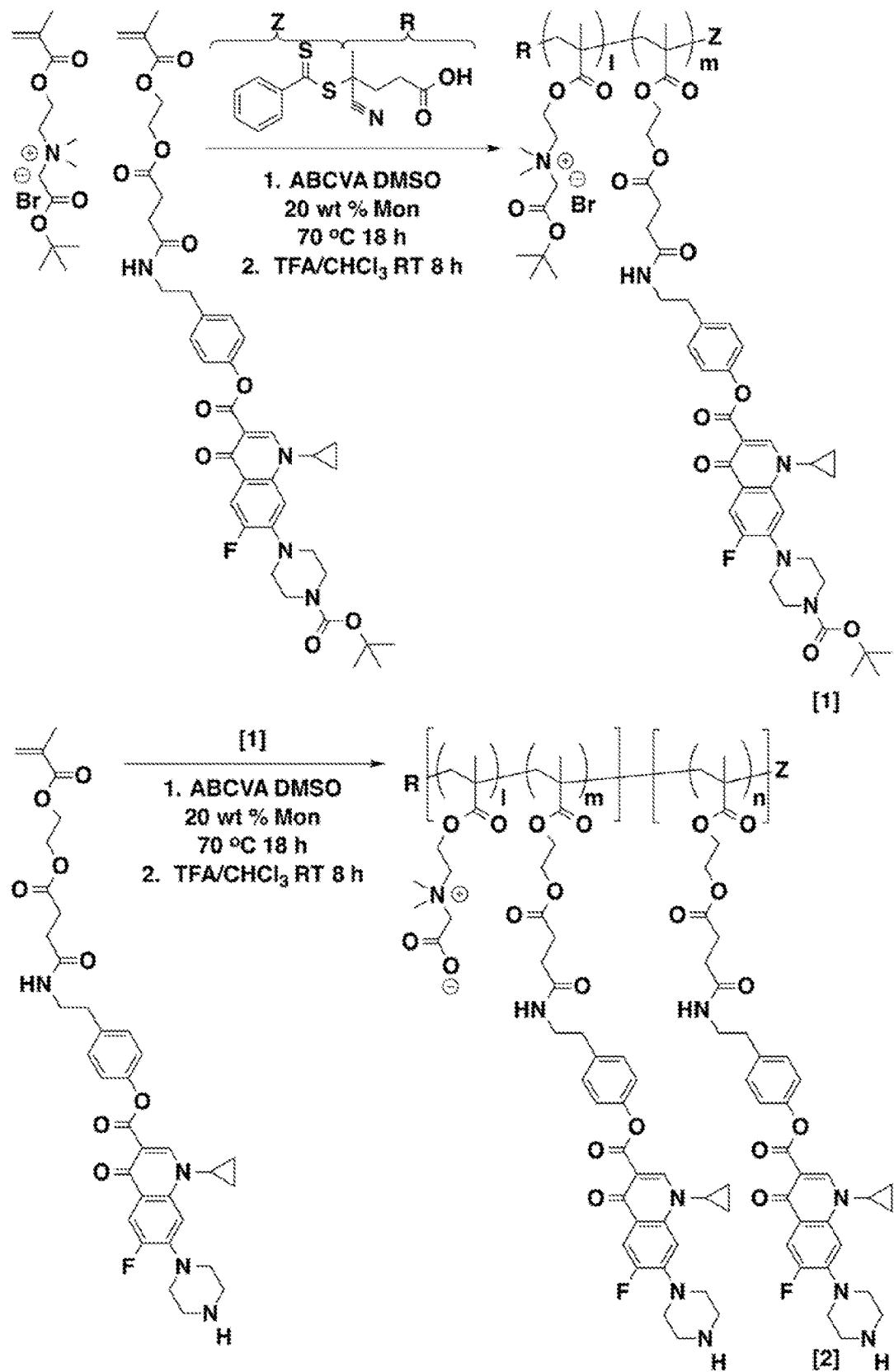
FIG. 8 presents schematic illustrations of the preparations of a representative copolymer of the invention [poly(CBM-co-CTM)] and a representative diblock copolymer of the invention [poly(CBM-co-CTM)-b-(CTM)].
Figure 9A:
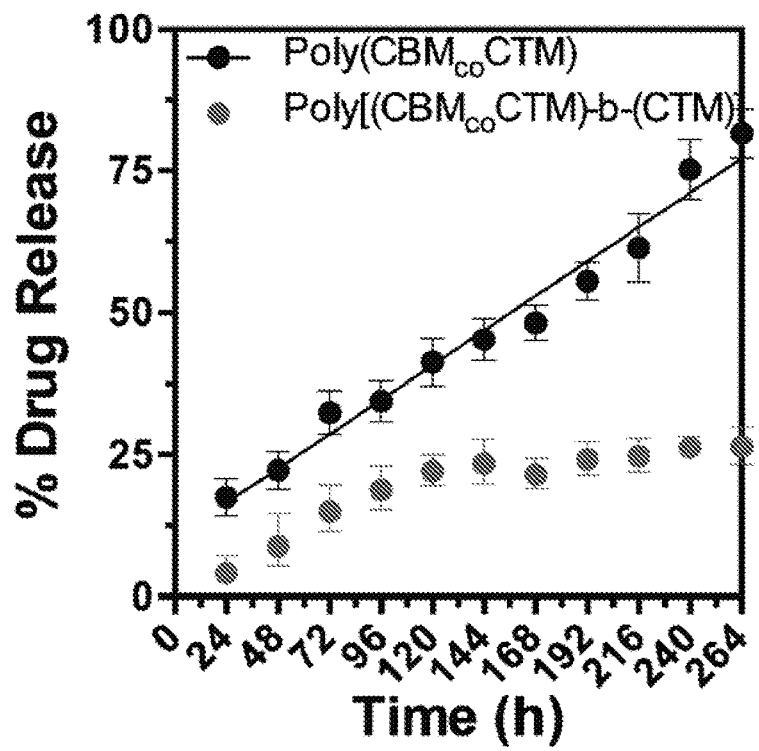
FIG. 9A compares drug release from a representative copolymer of the invention [poly(CBM-co-CTM)] and a representative diblock copolymer of the invention [poly(CBM-co-CTM)-b-(CTM)].
Figure 9B:
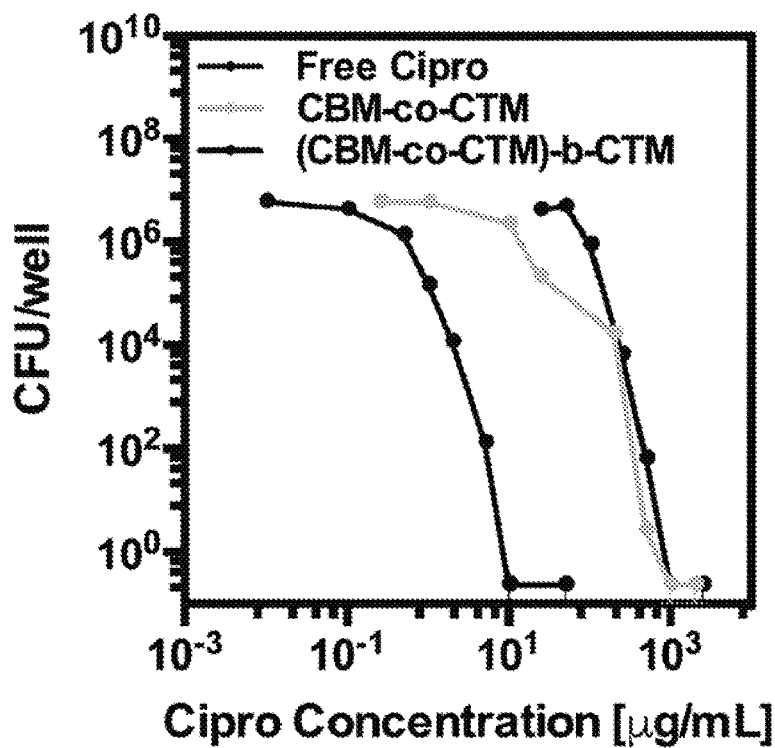
FIG. 9B compares co-culture data for a representative copolymer of the invention [poly(CBM-co-CTM)] and a representative diblock copolymer of the invention [poly(CBM-co-CTM)-b-(CTM)].
Figure 9C:
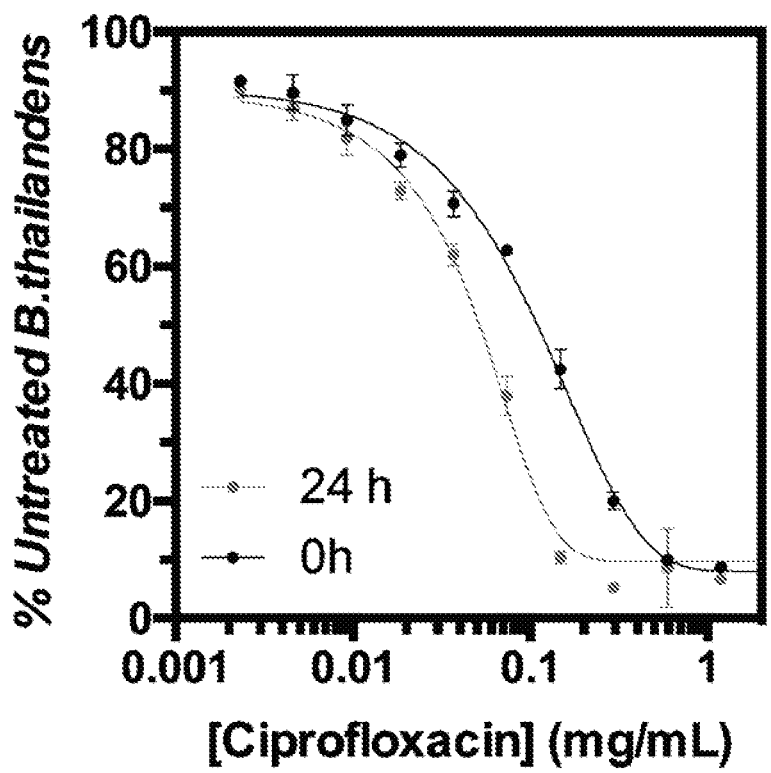
FIG. 9C shows that pre-incubation of a representative copolymer of the invention [poly(CBM-co-CTM)] in serum for 24 hours increases the antibiotic activity of the copolymer in planktonic cultures because it allows some of the ciprofloxacin to be released prior to infection.
Figure 10A:
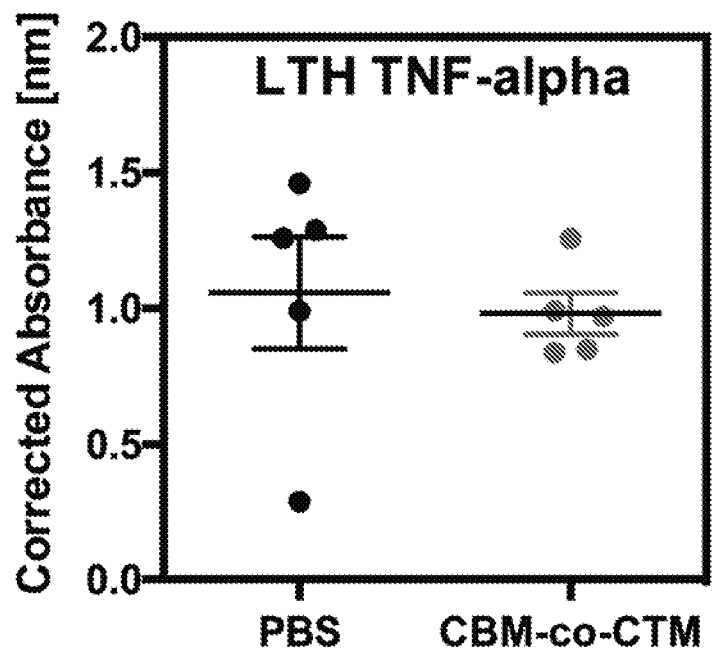
FIGS. 10A-10D illustrate in vivo biocompatibility for a representative copolymer of the invention [poly(CBM-co-CTM)] compared to phosphate buffered saline control (PBS): LTH TNF-alpha (10A); BALF TNF-alpha (10B); % Neutrophil (10C); and % Weight Change (10D).
Figure 10B:
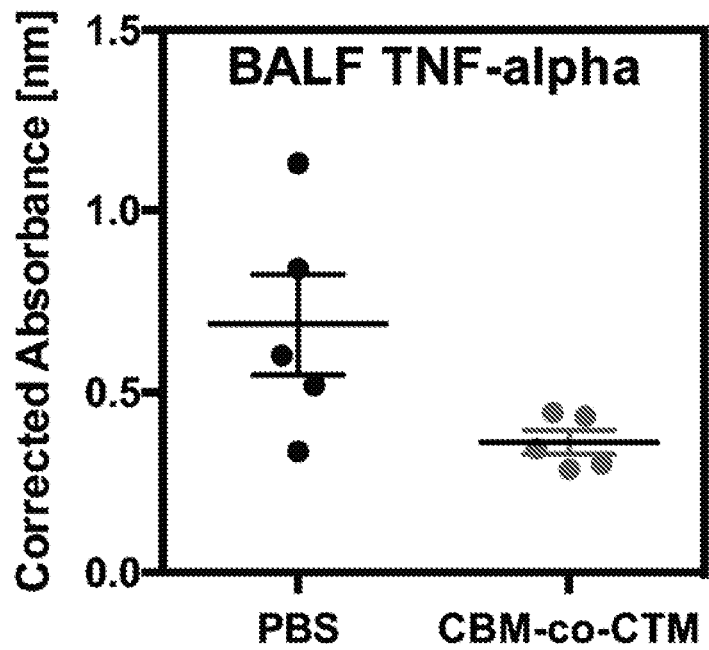
Figure 10C:
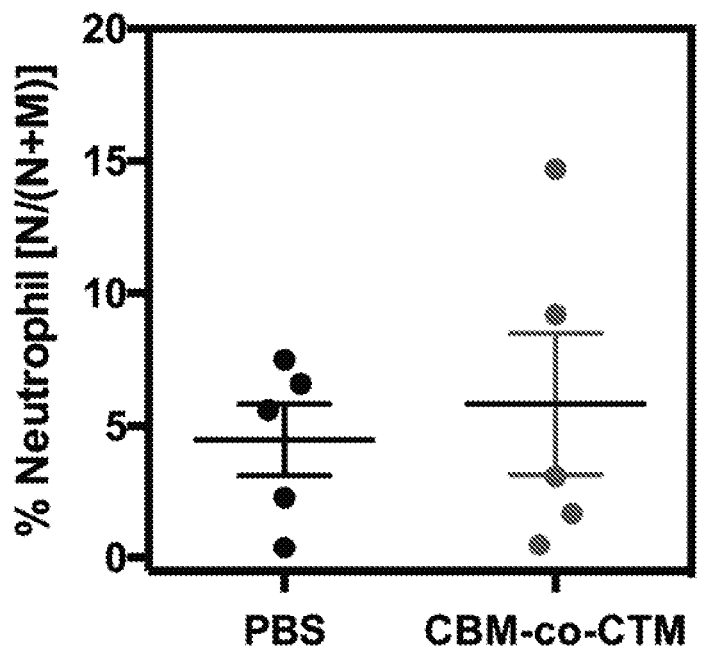
Figure 10D:
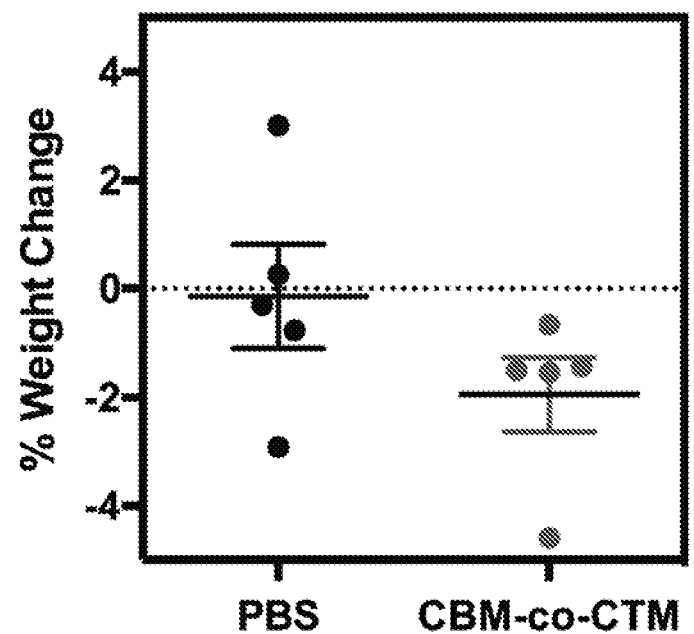
Figure 11:
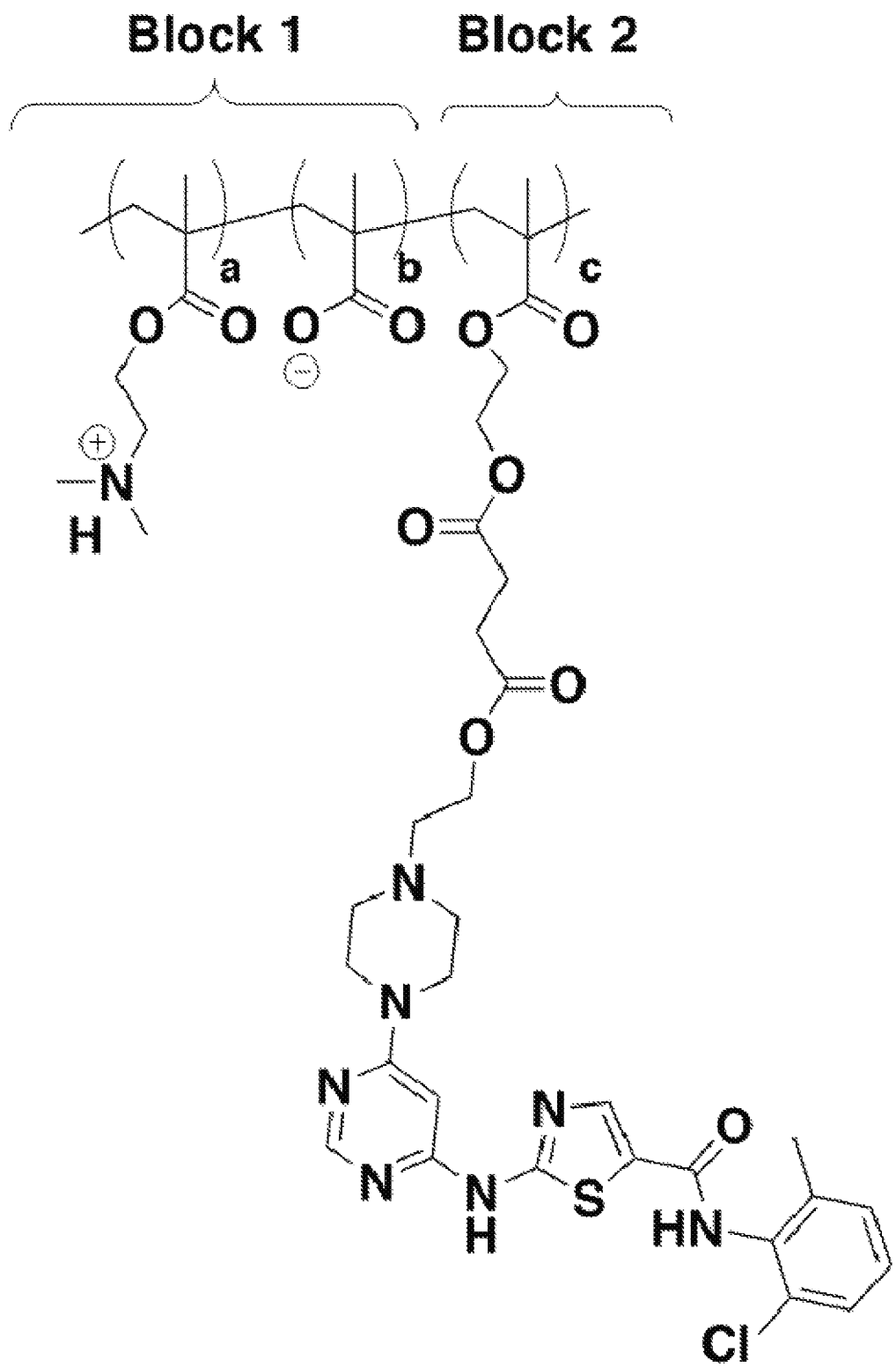
FIG. 11 is a schematic illustration of a representative diblock copolymer of the invention, poly(methacrylic acid-co-dimethylaminoethyl methacrylate)-b-(DtSMA) [poly(MAA-co-DMAEMA)-b-(DtSMA)], useful for the delivery of dasatinib.

The Preparation and Properties of Representative Prodrug Copolymers and Diblock Copolymers: Zwitterionic Stabilizing Groups In this example, the preparations and properties of representative ciprofloxacin prodrug copolymers and diblock copolymers of the invention are described. These copolymers include zwitterionic constitutional units. The preparation is illustrated schematically in FIG. 8, ciprofloxacin release is shown in FIG. 9, and therapeutic effectiveness is shown in FIGS. 9A and 9B.

Materials.

CTP and ABCVA are the RAFT agent and radical initiator that we used in these studies (Aldrich). CTM is a phenyl ester linked cipro monomer. tQuat is the tertiary butyl ester protected betaine monomer.

Synthesis of poly(tQuat-co-CTM)

Copolymerization of tQuat and CTM was conducted in DMSO at 70° C. for 18 h in the presence of CTP and ABCVA. The initial molar feed composition by mole was 17.8% CTM and 82.2% tQuat (33.33 wt % CTM, 66.66 wt % tQuat). The $[M]_o:[CTA]_o:[I]_o$ was 25:1:0.2 at an initial monomer concentration of 20 wt. %. To a 10 mL round bottom flask was added tQuat (2.00 g, 5.91 mmol), CTM (1.00 g, 1.29 mmol), CTP (80.5 mg, 0.288 mmol), ABCVA (16.1 mg, 0.0567 mmol), and DMSO (12 mL). The round bottom flask was then sealed with a rubber septa and purged with nitrogen for 1 hour. After this time the polymerization solution was transferred to a preheated water bath at 70° C. and allowed to react for 18 hours. After this time the solution was precipitated into a 50 times excess of diethyl ether. The precipitate was then redissolved in minimal methanol and then precipitated once more into diethyl ether. This process was repeated five additional times after which the copolymer was dried under high vacuum for 48 hours. The dry polymer was then dissolved in trifluoracetic acid at a polymer concentration of 50 mg/mL for 8 hours. After this time the polymer was precipitated into diethyl ether and dried overnight under high vacuum. The copolymer was then dissolved in phosphate buffer (pH 7.4, 200 mM) at a concentration of Synthesis of poly[(tQuat-co-CTM)-b-(CTM)]

The preparation of poly[(tQuat-co-CTM)-b-(CTM)] was conducted from a poly[(tQuat-co-CTM)] macro chain transfer agent (macroCTA) in DMSO. To a 5 mL round bottom flask was added poly(tQuat-co-CTM)] macroCTA (0.426 g, 0.039 mmol), CTM (0.387 g, 0.498 mmol), ABCVA (2.23 mg, 0.008 mmol), and DMSO 1.55 mL. The round bottom flask was then sealed with a rubber septa and purged with nitrogen for 1 hour. After this time the polymerization solution was transferred to a preheated water bath at 70° C. and allowed to react for 18 hours. After this time the solution was precipitated into a 50 times excess of diethyl ether. The precipitate was then redissolved in minimal methanol and then precipitated once more into diethyl ether. This process was repeated five additional times after which the copolymer was dried under high vacuum for 48 hours. The dry polymer was then dissolved in trifluoroacetic acid at a polymer concentration of 50 mg/mL for 8 hours. After this time the polymer was precipitated into diethyl ether and dried overnight under high vacuum. The copolymer was then dissolved in phosphate buffer (pH 7.4, 200 mM) at a concentration of 50 mg/ML and dialyszed against 20 mM phosphate buffer pH 7.4 at 5° C. The copolymer was then further purified via Sephadex PD10 column followed by lyophilization. Complete removal of the tBoc protect group was confirmed by $^1$H NMR.

Example 4

The Preparation and Properties of Representative Therapeutic Peptide Prodrug Copolymers and Diblock Copolymers: Enzyme Cleavable Linkage In this example, the preparations and properties of representative therapeutic peptide (pro-apoptotic peptide BIM) prodrug copolymers and diblock copolymers of the invention are described.

Synthesis and Characterization of Peptide Macromonomers.

FMOC protected (L) amino acids (EMD Millipore) and an FMOC protected 6-aminohexanoic acid (Ahx) spacer (AnaSpec) were used to synthesize two peptides macromonomers. The first contained the BIM peptide sequence capped on its N-terminus with a four amino acid cathepsin B substrate (FKFL) flanked on each side by Ahx: AhxFKFLAhxMRPEIWIAQELRRIGDEFNAY. The second control peptide monomer substituted BIM for a scrambled peptide sequence: AhxFKFLAhxLRMREIIDAYERQFGEPNIWA. An automaticed PS3 peptide synthesizer (Protein Technologies) and standard FMOC chemistry were used to synthesize the peptides on a solid support (rink amide MBHA resin (100-200 mesh), EMD Millipore). While still linked to the resin, the amino termini of the peptides were deprotected and functionalized with N-succinimidyl methacrylate (TCI America): MaAhxFKFLAhx<u>BIM</u> and MaAhxFKFLAhx<u>ScrBIM</u>. The peptide monomers were deprotected/cleaved from the resin by treatment with trifluoroacetic acid/triisopropylsilane/H$_2$O (9.5:2.5:2.5, v/v/v) for 4 hours and precipitated in cold ether. Crude peptide monomers were purified by reverse phase high performance liquid chromatography (RP-HPLC) on a Jupiter 5 μm C18 300A column (Phenomenx) with an Agilent 1260 HPLC. Ion trap mass spectrometry with electrospray (Bruker Esquire) was used to confirm the molecular weights of the purified peptide monomers.

RAFT Synthesis of Diblock Copolymers.

RAFT copolymerization of N,N-diethylaminoethyl methacrylate (DEAEMA) and butyl methacrylate (BMA) was conducted under nitrogen atmosphere in dioxane (50 wt % monomer) at 70° C. for 6 hours using 4-cyanopentanoic acid dithiobenzoate (CTP) as the chain transfer agent (CTA) and azobis(4-cyanopentanoic acid) (ABCVA) as the radical initiator. The molar composition of the reaction feed was 60% DEAEMA and 40% BMA, and the initial monomer ([M]$_o$) to CTA ([CTA]$_o$) to initiator ([I]$_o$) ratio was 200:1:0.1. The resulting macroCTA, poly[(DEAEMA)-co-(BMA)], was purified by dialysis in acetone for 48 hours, followed by dialysis in water for 24 hours, and dried by lyophilization. The macroCTA was then employed for block copolymerization of poly(ethylene glycol) methyl ether methacrylate (MW=300 Da, PEGMA$_{300}$) and peptide macromonomer. Two different polymers were synthesized by varying the identity of the peptide monomer: poly[(DEAEMA)-co-(BMA)]-b-[(PEGMA$_{300}$)-c-(MaAhxFKFLAhx<u>BIM</u>)] (Pol<u>BIM</u>) and poly[(DEAEMA)-co-(BMA)]-b-[(PEGMA$_{300}$)-c-(MaAhxFKFLAhx<u>ScrBIM</u>)] (Pol<u>ScrBIM</u>). The block copolymerizations were conducted for 18 hours at 70° C. under nitrogen atmosphere in an equal by volume mixture of dimethyl sulfoxide (DMSO) and dioxane (20 wt % monomer and macroCTA). The molar composition of the monomer feed was 96% PEGMA$_{300}$ and 4% peptide, and the [M]$_o$:[mCTA]$_o$:[I]$_o$ ratio was 45:1:0.1. The resulting diblock copolymers were precipitated 4× in a mixture of petroleum ether and diethyl ether (9:1, v/v) to remove unreacted PEGMA$_{300}$ and solvents. To remove unreacted peptide, the polymers were redissolved in acetone, the peptide monomer was removed by centrifugation, and polymers were reprecipitated in petroleum ether. This two-step precipitation scheme was repeated 3× and the purified diblock copolymers were lyophilized.

Polymer Characterization by Gel Permeation Chromatography (GPC), $^1$H-NMR and RP-HPLC.

To measure the number average molecular weights (M$_n$) and polydispersities (PDIs) of the polymers, GPC was conducted using Tosoh SEC TSK GEL α-3000 and α-4000 columns (Tosoh Bioscience), a 1200 Series liquid chromatography system (Agilent), and a miniDAWN TREOS three-angle light scattering instrument with an Optilab TrEX refractive index detector (Wyatt Technology). The mobile phase was 0.1 wt % lithium bromide in HPLC-grade N,N-dimethylformamide at 60° C. and a flow rate of 1 mL/min. The compositions of the macroCTA and diblock copolymers were determined by $^1$H-NMR spectroscopy (Bruker avance DRX 499) in CDCL$_3$ and C$_2$D$_6$OS, respectively. For quantification of peptide content, reaction aliquots were collected at T$_o$ and T$_x$ and monomer depletion was measured by RP-HPLC (abs 280 nm).

Formulation of Polymer Micelles.

Aqueous polymer solutions were prepared in DMSO at 100 mg/mL and diluted into phosphate buffer saline (PBS) at 10 mg/mL. Serial dilutions were made and absorbance at 282 nm was measured to determine extinction coefficients. DMSO was removed by centrifugal dialysis in PBS (Amicon Ultra, 5 mL, 3K MWCO, Millipore), and final polymer concentrations were determined by UV spectrometry.

Cathepsin B Cleavage Assay.

Human liver cathepsin B (Enzo Life Sciences) was activated for 15 minutes in a solution of 0.158 mg/mL cathepsin B, 20 mM DTT, and 10 mM EDTA at 37° C. Peptide or polymer was then solubilized in reaction buffer (10 mM phosphate, 1 mM EDTA, pH 6.6, 37° C.) and added to the enzyme solution for a final concentration of 1.28 µg/mL cathepsin B and 65 04 peptide/polymer. At various time points, reaction aliquots were removed, enzymatic activity was halted by addition of a thioprotease inhibitor (E-64 (Thermo Scientific), 26 µg/mL), and RP-HPLC and mass spectrometry were used to quantify cathepsin B cleavage of the FKFL linker. Cleavage of the polymers was also visualized by SDS-PAGE on 8-16% Tris-Glycine Gels (Bio-Rad). For protein gel analyses, reactions were conducted at 3× concentration and 160 µg of polymer was loaded per well.

Serum Stability of Peptide Macromonomers and Polymers.

The stability of the peptide (FKFL) linker in the presence of serum proteases was evaluated by incubating the peptide monomers and polymers in human serum and analyzing the degradation products over time. Peptide (40 mM, DMSO) or polymer (4 mM, PBS) was added to human serum to a final peptide/polymer concentration of 400 µM and incubated at 37° C. At various time points, 40 µL aliquots of the mixture were withdraw and 40 µL of acetonitrile was added to precipitate serum proteins and halt protease degradation. Precipitated solutions were centrifuged at 13,000 rpm for 10 min and supernatants were analyzed by MALDI-TOF MS using a Bruker Autoflex II.

Sizing of Micelles by Dynamic Light Scattering.

The hydrodynamic diameters of the polymer micelles were determined by dynamic light scattering (DLS) using a Nanoseries Zetasizer (Malvern). Measurements were taken of 0.25 mg/mL polymer solutions in 100 mM phosphate buffer (supplemented with 150 mM NaCl) at pH values ranging from 5.8 to 7.4. Mean particle diameter is reported as the number average±the half width of three independently prepared formulations.

pH-Responsive Hemolysis Assay.

The ability of the polymers to induce pH-dependent membrane destabilization was assessed via a red blood cell hemolysis. Briefly, polymers (60 µg/mL) were incubated for 1 hour at 37° C. with human red blood cells in a 100 mM phosphate buffer (supplemented with 150 mM NaCl) at pH values ranging from 5.8 to 7.4. Percent red blood cell lysis (hemolysis) was quantified by measuring hemoglobin release (abs 541 nm) relative to a 100% lysis control (0.1% Triton X-100).

Cell Culture.

SKOV3 human ovarian cancer cells (ATCC) were maintained in RPMI 1640 Medium with L-glutamine and HEPES supplemented with 10% FBS (GIBCO) and 1% penicillin/streptomycin (GIBCO). Cells were maintained in log-phase growth at 37° C. and 5% $CO_2$.

Cell Viability Assay.

The cell killing activity of the polymers was initially evaluated using the CellTiter 96 Aqueous One Solution Cell Proliferation Assay (MTS) (Promega). SKOV3 cells were plated in a 96-well plate at a density of 7,000 cells per well and allowed to adhere for 24 hours. Cells were then incubated with 100 µL of polymer solution at concentrations ranging from 0-10 µM for 96 hours. At 96 hours, cell viability was quantified by adding 20 µL of [3-(4,5-dimethylthiazol-2-yl)-5-(3-carboxymethoxyphenyl)-2-(4-sulfophenyl)-2H-tetrazolium (MTS) reagent to each well, incubating for 30 minutes, and measuring the absorbance at 490 nm using a plate reader. All experimental groups were run in triplicate and the results from three independent experiments were averaged.

Caspase-3/7 Activity Assay.

Caspase 3/7 activity was measured using a SensoLyte Homogenous AMC Caspase-3/7 Assay Kit (AnaSpec). SKOV3 cells were plated in a black 96-well plate with a clear bottom at a density of 7,000 per well and then treated with polymer (0-10 µM) for 72 hours. Assay reagents were mixed with cell culture medium as per the manufacturer's instructions, incubated for 24 hours, and fluorescence (ex/em=380 nm/500 nm) was measured using a plate reader. Percent caspase 3/7 activity was calculated relative to untreated cell cultures.

Annexin V Apoptosis Assay.

Induction of apoptosis was measured with a FITC Annexin V/Dead Cell Apoptosis Kit (Invitrogen) as per the manufacturer's instructions. SKOV3s cells were plated in 6-well plates at a density of 120,000 cells per well and treated with 10 µM polymer solutions for 72 hours. After 72 hours, cells were trypsinized, rinsed in PBS, centrifuged, stained with FITC-annexin V, and analyzed on a BD LSRII flow cytometer.

While illustrative embodiments have been illustrated and described, it will be appreciated that various changes can be made therein without departing from the spirit and scope of the invention.

The invention claimed is:

1. A copolymer having the formula:

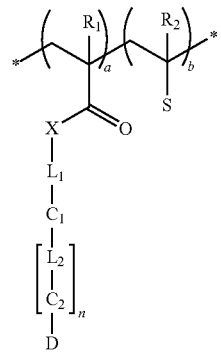

wherein $R_1$ and $R_2$ are independently selected from hydrogen and methyl,

S is a poly(ethylene oxide) group,

X is O or NH,

D is a therapeutic agent, $C_1$ is a cleavable linkage, $L_1$ is a linker that covalently couples $C_1$ to X, $C_2$ at each occurrence is an independent cleavable linkage, $L_2$ is a linker that covalently couples $C_1$ to $C_2$, n is 0 or 1, a is an integer from about 5 to about 500, b is an integer from about 5 to about 500, and each * represents the copolymer terminus, wherein $C_1$ and $C_2$ are independently selected from the group consisting of a phenyl ester, an acetal, a hemiacetal, a hemiacetal ester, a hydrazine, and an amino acid sequence cleavable by enzymatic action.

2. The copolymer of claim 1, wherein $L_1$ is —$(CH_2)_n$— where n is 2-10.

3. The copolymer claim 1, wherein $L_1$ is —$(CH_2CH_2O)_n$— where n is 2-4.

4. The copolymer of claim 1, wherein $L_2$ is —$(CH_2)_n$— where n is 2-10.

5. The copolymer of claim 1, wherein $L_2$ is —$(CH_2CH_2O)_n$— where n is 2-4.

6. The copolymer of claim 1, wherein S is a poly(ethylene oxide) group having at least five ethylene oxide repeating units.

7. The copolymer of claim 1, wherein S is a poly(ethylene oxide) group having from five (5) to thirty (30) ethylene oxide repeating units.

8. A method for administering a therapeutic agent to a subject, comprising administering a therapeutically effective amount of a copolymer of claim 1 to a subject in need thereof.

9. A method for treating a disease or condition treatable by a therapeutic agent, comprising administering a therapeutically effective amount of a copolymer of claim 1 to a subject in need thereof, wherein the therapeutic agent covalently coupled to the copolymer is effective to treat the disease or condition.

10. A copolymer having the formula:

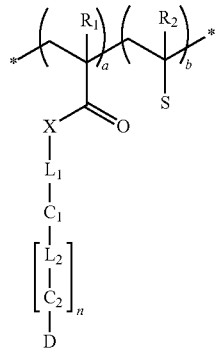

wherein $R_1$ and $R_2$ are independently selected from hydrogen and methyl,

S is a copolymer-stabilizing group,

X is O or NH,

D is a therapeutic agent, $C_1$ is a cleavable linkage, $L_1$ is a linker that covalently couples $C_1$ to X, $C_2$ at each occurrence is an independent cleavable linkage, $L_2$ is—a linker that covalently couples $C_1$ to $C_2$—, wherein n1 is 2-10, n is 1, a is an integer from about 5 to about 500, b is an integer from about 5 to about 500, and each * represents the copolymer terminus, wherein $C_1$ and $C_2$ are independently selected from the group consisting of a phenyl ester, an acetal, a hemiacetal, a hemiacetal ester, a hydrazine, and an amino acid sequence cleavable by enzymatic action.

11. The copolymer of claim 10, wherein $L_1$ is —$(CH_2)_n$— where n is 2-10.

12. The copolymer claim 10, wherein $L_1$ is —$(CH_2CH_2O)_n$— where n is 2-4.

13. The copolymer of claim 10, wherein S comprises a poly(ethylene oxide) group.

14. The copolymer of claim 10, wherein S comprises a poly(ethylene oxide) group having at least five ethylene oxide repeating units.

15. The copolymer of claim 10, wherein S comprises a poly(ethylene oxide) group having from five (5) to thirty (30) ethylene oxide repeating units.

16. The copolymer of claim 10, wherein S comprises a zwitterionic group.

17. The copolymer of claim 10, wherein S comprises a zwitterionic group selected from the group consisting of a carboxybetaine group, a sulfobetaine group, and a phosphobetaine group.

18. A method for administering a therapeutic agent to a subject, comprising administering a therapeutically effective amount of a copolymer of claim 10 to a subject in need thereof.

19. A method for treating a disease or condition treatable by a therapeutic agent, comprising administering a therapeutically effective amount of a copolymer of claim 10 to a subject in need thereof, wherein the therapeutic agent covalently coupled to the copolymer is effective to treat the disease or condition.

* * * * *